US008932249B2

(12) United States Patent
Parihar et al.

(10) Patent No.: US 8,932,249 B2
(45) Date of Patent: Jan. 13, 2015

(54) TROCAR ASSEMBLY

(75) Inventors: Shailendra K. Parihar, Mason, OH (US); Haresh Patil, Maharashtra (IN); Carl J. Shurtleff, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 865 days.

(21) Appl. No.: 12/575,574

(22) Filed: Oct. 8, 2009

(65) Prior Publication Data
US 2011/0087168 A1 Apr. 14, 2011

(51) Int. Cl.
*A61M 37/00* (2006.01)
*A61M 5/178* (2006.01)
*A61B 17/34* (2006.01)
*A61M 13/00* (2006.01)
*A61M 5/32* (2006.01)

(52) U.S. Cl.
CPC .............. *A61B 17/3498* (2013.01); *A61B 17/34* (2013.01); *A61M 13/003* (2013.01)
USPC .......................... 604/26; 604/272; 604/167.03

(58) Field of Classification Search
USPC ........................... 604/23, 26, 164.01–164.12, 604/167.01–167.06, 93.01, 264, 272; 606/185
See application file for complete search history.

(56) References Cited

U.S. PATENT DOCUMENTS

| | | | |
|---|---|---|---|
| 448,702 A | 3/1891 | Wilson | |
| 3,504,699 A | 4/1970 | Grise | |
| 3,773,233 A | 11/1973 | Souza | |
| 4,233,982 A * | 11/1980 | Bauer et al. ................... | 604/256 |
| 4,436,519 A | 3/1984 | O'Neill | |
| 4,601,710 A | 7/1986 | Moll | |
| 4,610,665 A | 9/1986 | Matsumoto et al. | |
| 4,654,030 A | 3/1987 | Moll et al. | |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,073,169 A | 12/1991 | Raiken | |

(Continued)

FOREIGN PATENT DOCUMENTS

| | | |
|---|---|---|
| CA | 2056543 | 6/1992 |
| DE | 10100756 | 8/2002 |

(Continued)

OTHER PUBLICATIONS

PCT, International Search Report, International Application No. PCT/US2010/051465 (Mar. 4, 2011).

(Continued)

*Primary Examiner* — Nicholas Lucchesi
*Assistant Examiner* — Weng Lee

(57) ABSTRACT

A trocar assembly including a sleeve assembly defining a working channel extending axially therethrough and including an insufflation port in fluid communication with the working channel, and an insufflation valve assembly fluidly coupled to the insufflation port, the insufflation valve assembly including a valve member and a housing, wherein the valve member defines an inlet channel and is biased relative to the housing to a first position in which the inlet channel is in fluid communication with the working channel, and wherein the valve member is moveable relative to the housing from the first position to a second position in which the inlet channel is fluidly decoupled from the working channel.

19 Claims, 49 Drawing Sheets

(56) References Cited

U.S. PATENT DOCUMENTS

| | | |
|---|---|---|
| 5,098,388 A | 3/1992 | Kulkashi et al. |
| 5,104,383 A | 4/1992 | Schichman |
| 5,147,316 A | 9/1992 | Castillenti |
| 5,203,773 A | 4/1993 | Green |
| 5,209,737 A | 5/1993 | Ritchart et al. |
| 5,211,634 A | 5/1993 | Vaillancourt |
| 5,246,425 A | 9/1993 | Hunsberger et al. |
| 5,257,975 A | 11/1993 | Foshee |
| 5,263,939 A | 11/1993 | Wortrich |
| 5,290,243 A | 3/1994 | Chodorow et al. |
| 5,300,033 A | 4/1994 | Miller |
| 5,308,336 A | 5/1994 | Hart et al. |
| 5,324,270 A | 6/1994 | Kayan et al. |
| 5,330,497 A | 7/1994 | Freitas et al. |
| 5,343,775 A | 9/1994 | Easton et al. |
| 5,354,280 A * | 10/1994 | Haber et al. ............ 604/167.03 |
| 5,356,394 A * | 10/1994 | Farley et al. ............... 604/256 |
| 5,364,372 A | 11/1994 | Danks et al. |
| 5,366,445 A | 11/1994 | Haber et al. |
| 5,385,552 A | 1/1995 | Haber et al. |
| 5,385,553 A | 1/1995 | Hart et al. |
| 5,389,077 A | 2/1995 | Melinyshyn et al. |
| 5,441,041 A | 8/1995 | Sauer et al. |
| 5,453,094 A | 9/1995 | Metcalf et al. |
| 5,456,284 A | 10/1995 | Ryan et al. |
| 5,456,673 A | 10/1995 | Ziegler et al. |
| 5,467,762 A | 11/1995 | Sauer et al. |
| 5,472,427 A | 12/1995 | Rammler |
| 5,514,087 A * | 5/1996 | Jones ............................... 604/26 |
| 5,534,009 A | 7/1996 | Lander |
| 5,542,931 A | 8/1996 | Gravener et al. |
| 5,549,565 A | 8/1996 | Ryan et al. |
| 5,554,097 A | 9/1996 | Guy |
| 5,569,160 A | 10/1996 | Sauer et al. |
| 5,578,016 A | 11/1996 | Zinger |
| 5,584,850 A | 12/1996 | Hart et al. |
| 5,603,702 A | 2/1997 | Smith et al. |
| 5,613,954 A * | 3/1997 | Nelson et al. ............ 604/167.03 |
| 5,643,301 A | 7/1997 | Mollenauer |
| 5,662,613 A | 9/1997 | Astarita |
| 5,720,730 A | 2/1998 | Blake, III |
| 5,722,962 A | 3/1998 | Garcia |
| 5,725,504 A | 3/1998 | Collins |
| 5,743,884 A | 4/1998 | Hasson et al. |
| 5,800,451 A | 9/1998 | Buess |
| 5,807,338 A | 9/1998 | Smith et al. |
| 5,817,061 A | 10/1998 | Goodwin et al. |
| 5,839,436 A * | 11/1998 | Fangrow et al. .......... 128/205.24 |
| 5,843,113 A | 12/1998 | High |
| 5,865,812 A * | 2/1999 | Correia ......................... 604/248 |
| 5,871,471 A | 2/1999 | Ryan et al. |
| 5,882,344 A | 3/1999 | Stouder, Jr. |
| 5,895,377 A | 4/1999 | Smith et al. |
| 5,980,493 A | 11/1999 | Smith et al. |
| 6,024,729 A | 2/2000 | Dehdashtian et al. |
| 6,039,725 A | 3/2000 | Moenning et al. |
| 6,080,134 A | 6/2000 | Lotti et al. |
| 6,086,603 A | 7/2000 | Termin et al. |
| 6,093,176 A | 7/2000 | Dennis |
| 6,197,002 B1 | 3/2001 | Peterson |
| 6,254,529 B1 | 7/2001 | Ouchi |
| 6,270,484 B1 | 8/2001 | Yoon |
| 6,277,100 B1 | 8/2001 | Raulerson et al. |
| 6,283,948 B1 | 9/2001 | McKernan et al. |
| 6,302,852 B1 | 10/2001 | Fleming, III et al. |
| 6,352,520 B1 | 3/2002 | Miyazaki |
| 6,494,896 B1 | 12/2002 | D'Alessio et al. |
| 6,569,119 B1 | 5/2003 | Haberland et al. |
| 6,569,120 B1 | 5/2003 | Green et al. |
| 6,613,063 B1 | 9/2003 | Hunsberger |
| 6,656,198 B2 | 12/2003 | Tsonton et al. |
| 6,685,630 B2 | 2/2004 | Sauer et al. |
| 6,685,665 B2 | 2/2004 | Booth et al. |
| 6,692,467 B2 | 2/2004 | McFarlane |
| 6,702,787 B2 | 3/2004 | Racenet et al. |
| 7,150,753 B2 | 12/2006 | Rehil |
| 7,163,525 B2 | 1/2007 | Franer |
| 7,165,568 B2 | 1/2007 | Kessell et al. |
| 7,285,112 B2 | 10/2007 | Stubbs et al. |
| 7,329,242 B2 | 2/2008 | Peery |
| 7,344,519 B2 | 3/2008 | Wing et al. |
| 7,367,960 B2 | 5/2008 | Stellon et al. |
| 7,371,227 B2 | 5/2008 | Zeiner |
| 7,413,559 B2 | 8/2008 | Stubbs et al. |
| 7,481,795 B2 | 1/2009 | Thompson et al. |
| 2002/0007152 A1 | 1/2002 | Hermann et al. |
| 2002/0007153 A1 | 1/2002 | Wells et al. |
| 2002/0010425 A1 | 1/2002 | Guo et al. |
| 2003/0060770 A1 | 3/2003 | Wing et al. |
| 2004/0049173 A1 | 3/2004 | White et al. |
| 2004/0064100 A1 | 4/2004 | Smith |
| 2004/0147949 A1 | 7/2004 | Stellon et al. |
| 2004/0171990 A1 | 9/2004 | Dennis et al. |
| 2005/0040065 A1 | 2/2005 | O'Heeron |
| 2005/0067308 A1 | 3/2005 | Thompson et al. |
| 2005/0070850 A1 | 3/2005 | Albrecht |
| 2005/0070851 A1 | 3/2005 | Thompson et al. |
| 2005/0070943 A1 | 3/2005 | Hueil et al. |
| 2005/0171465 A1 * | 8/2005 | Smith .............................. 604/26 |
| 2005/0261661 A1 | 11/2005 | McFarlane |
| 2006/0021891 A1 | 2/2006 | Franer et al. |
| 2006/0155247 A1 | 7/2006 | Lampropoulos et al. |
| 2006/0229655 A1 | 10/2006 | Voegele et al. |
| 2006/0264992 A1 | 11/2006 | Franer et al. |
| 2007/0088275 A1 | 4/2007 | Stearns et al. |
| 2007/0088277 A1 | 4/2007 | McGinley et al. |
| 2007/0106319 A1 | 5/2007 | Au et al. |
| 2007/0260184 A1 | 11/2007 | Justis et al. |
| 2008/0092337 A1 | 4/2008 | Gross |
| 2008/0132827 A1 | 6/2008 | Gresham |
| 2008/0132847 A1 | 6/2008 | Wing et al. |
| 2008/0171987 A1 | 7/2008 | Franer et al. |
| 2008/0177239 A1 | 7/2008 | Li et al. |
| 2009/0005799 A1 | 1/2009 | Franer et al. |
| 2009/0030375 A1 | 1/2009 | Franer et al. |
| 2009/0076456 A1 | 3/2009 | Armstrong et al. |
| 2009/0076464 A1 | 3/2009 | Gresham |
| 2009/0137943 A1 * | 5/2009 | Stearns et al. .................. 604/26 |
| 2009/0157006 A1 | 6/2009 | Nardeo et al. |

FOREIGN PATENT DOCUMENTS

| | | |
|---|---|---|
| DE | 20209525 | 11/2002 |
| DE | 202006017791 | 1/2007 |
| EP | 0339945 | 11/1989 |
| EP | 0567142 | 10/1993 |
| EP | 0568383 | 11/1993 |
| EP | 0696459 | 2/1996 |
| EP | 2000099 | 12/2008 |
| FR | 2667780 | 4/1992 |
| WO | 94/03232 | 2/1994 |
| WO | 00/35529 | 6/2000 |
| WO | 03/020140 | 3/2003 |
| WO | 03/091608 | 11/2003 |
| WO | 2004/033004 | 4/2004 |

OTHER PUBLICATIONS

PCT, International Search Report and Written Opinion, International Application No. PCT/US2010/051473 (Dec. 16, 2010).

PCT, International Search Report and Written Opinion, International Application No. PCT/US2010/051477 (Dec. 8, 2010).

PCT, International Search Report and Written Opinion, International Application No. PCT/US2010/051465 (Mar. 4, 2011).

Office Action, U.S. Appl. No. 12/575,537 (Feb. 6, 2012).

Office Action, U.S. Appl. No. 12/575,537 (Sep. 5, 2012).

Office Action, U.S. Appl. No. 12/575,598 (Dec. 27, 2011).

Notice of Allowance, U.S. Appl. No. 12/575,598 (Mar. 20, 2013).

* cited by examiner

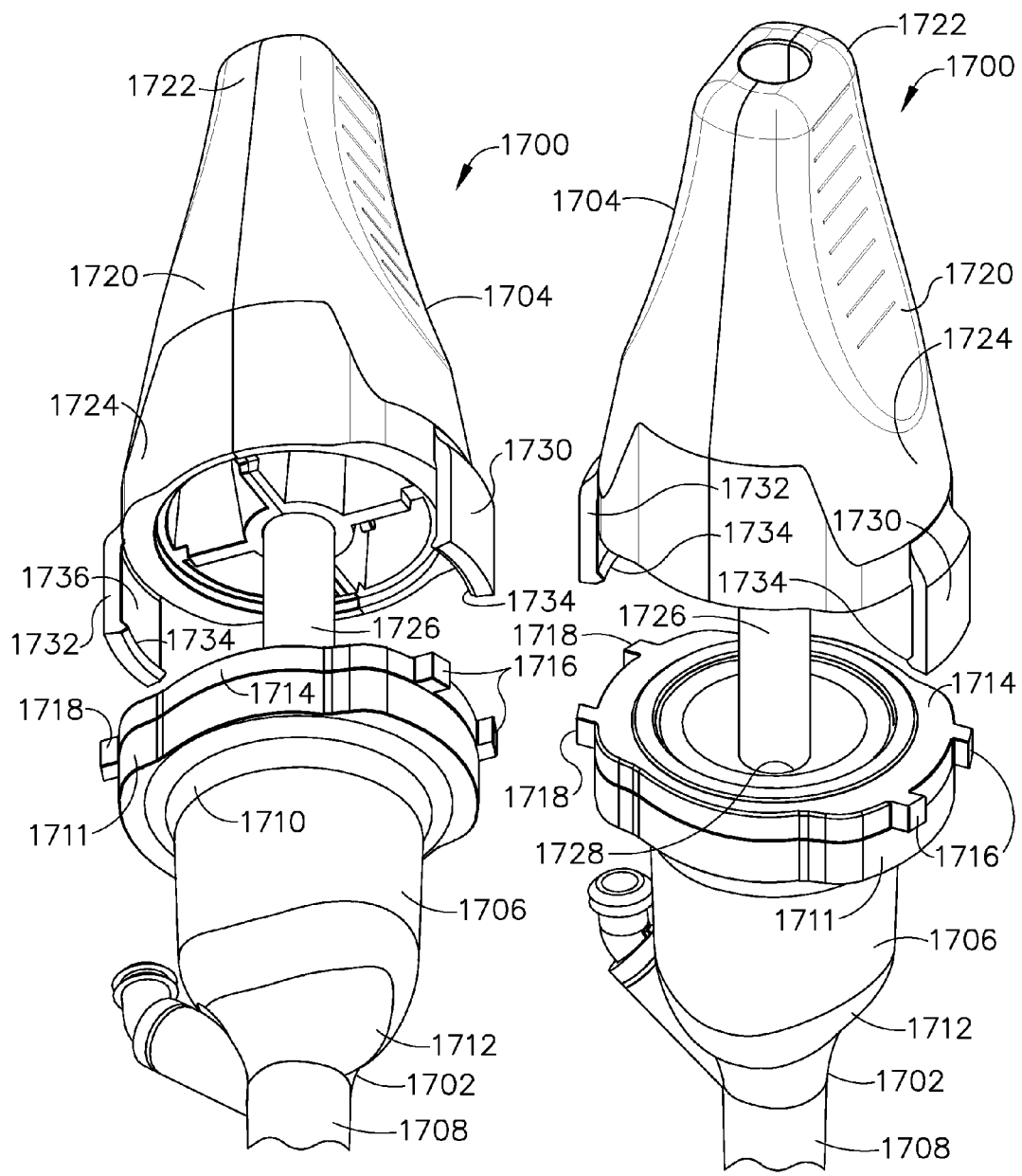

TROCAR ASSEMBLY

FIELD

The present patent application relates generally to surgical devices and procedures and, more particularly, to trocar assemblies for use in surgical procedures.

BACKGROUND

A trocar assembly typically includes an obturator extending through the elongated working channel of a sleeve such that the penetrating tip of the obturator extends beyond the distal end of the sleeve. During surgery (e.g., laparoscopic surgery), the penetrating tip of the obturator is advanced through the abdominal wall of the patient until the trocar assembly extends into the abdominal cavity. A scoping device may be used to provide visual feedback during the insertion step. Once the trocar has been positioned as desired, the obturator is removed from the sleeve, thereby providing the practitioner with a small channel into the patient's abdominal cavity.

Typically, an insufflation fluid, such as carbon dioxide gas, is fed through the sleeve of the trocar assembly and into the abdominal cavity to elevate the abdominal wall and expose the underlying organs. Then, with the abdomen insufflated, the practitioner may introduce various medical instruments, such as scoping devices, graspers, scissors and the like, into the abdominal cavity via the working channel of the sleeve to view and manipulate tissue.

During laparoscopic surgery, more than one trocar assembly may be used such that multiple instruments can be inserted into the abdominal cavity at the same time. However, the more trocar assemblies used during a procedure, the more likely it becomes that the crowded surgical space will interfere with the practitioner's techniques. For example, in single site laparoscopy, a single incision is made through the skin, such as around the umbilicus, and then multiple trocar assemblies are inserted through the abdominal wall at the single skin incision, thereby minimizing patient trauma, but also crowding multiple trocar assemblies in close proximity.

SUMMARY

In one aspect, the disclosed trocar assembly may include a sleeve assembly defining a working channel extending axially therethrough and including an insufflation port in fluid communication with the working channel, and an insufflation valve assembly fluidly coupled to the insufflation port, the insufflation valve assembly including a valve member and a housing, wherein the valve member defines an inlet channel and is biased relative to the housing to a first position in which the inlet channel is in fluid communication with the working channel, and wherein the valve member is moveable relative to the housing from the first position to a second position in which the inlet channel is fluidly decoupled from the working channel.

In another aspect, the disclosed trocar assembly may include a sleeve assembly having a cannula connected to a housing and an obturator assembly including a handle connected to an obturator, wherein the obturator assembly is receivable in the sleeve assembly to define a gripping portion that includes the housing and the handle, the gripping portion having an axial length and a maximum width, and wherein a ratio of the axial length to the maximum width ranges from about 2.5 to about 3.5

In another aspect, the disclosed trocar assembly may include a sleeve assembly defining a longitudinal axis and including a housing, a channel seal received in the housing, and a cannula connected to the housing to define a working channel extending axially through the sleeve assembly, wherein the channel seal includes a deformable body having a plurality of slits extending axially therethrough to define a plurality of segments, and an obturator assembly including a handle connected to an elongated obturator, wherein the elongated obturator is sized to pass through the working channel of the sleeve assembly.

In another aspect, the disclosed trocar assembly may include a sleeve assembly defining a longitudinal axis and including a housing, a channel seal having a duckbill portion received in the housing, and a cannula connected to the housing to define a working channel extending axially through the sleeve assembly, wherein the sleeve assembly further includes a push tab extending through an opening in the housing and radially aligned with the duckbill portion, and wherein the push tab is biased outward through the opening and out of engagement with the duckbill portion, and an obturator assembly including a handle connected to an elongated obturator, wherein the elongated obturator is sized to pass through the working channel of the sleeve assembly.

In another aspect, the disclosed trocar assembly may include a sleeve assembly defining a longitudinal axis and including a cannula connected to a housing to define a working channel extending axially therethrough, and an insufflation port in fluid communication with the working channel, wherein the insufflation port defines a longitudinal axis, and wherein the longitudinal axis of the insufflation port is parallel with the longitudinal axis of the sleeve assembly, and an obturator assembly including a handle connected to an elongated obturator, wherein the elongated obturator is sized to pass through the working channel of the sleeve assembly.

In another aspect, the disclosed trocar assembly may include a sleeve assembly defining a longitudinal axis and including a housing, a channel seal, and a cannula connected to the housing to define a working channel extending axially through the sleeve assembly, wherein the housing and the channel seal are formed as a single, monolithic body, and an obturator assembly including a handle connected to an elongated obturator, wherein the elongated obturator is sized to pass through the working channel of the sleeve assembly.

In another aspect, the disclosed trocar assembly may include a sleeve assembly defining a longitudinal axis and including a housing and a cannula, the cannula having a proximal end and a distal end, wherein the proximal end is connected to the housing to define a working channel extending axially through the sleeve assembly, and wherein the distal end includes a beveled portion that terminates at a tip, an obturator assembly connectable to the sleeve assembly and including a handle connected to an elongated obturator, wherein the elongated obturator is sized to be received in the working channel and includes a penetrating tip having at least one blade extending outward therefrom, wherein the blade is disposed at a predetermined angle relative to the tip of the sleeve assembly when the obturator assembly is connected to the sleeve assembly.

In another aspect, the disclosed trocar assembly may include an obturator assembly including a handle connected to an elongated obturator and a first portion of an engagement mechanism and a sleeve assembly defining a longitudinal axis and including a second portion of an engagement mechanism and a cannula connected to a housing to define a working channel extending axially through the sleeve assembly, wherein the first portion of the engagement mechanism is configured to engage the second portion of the engagement mechanism to connect the obturator assembly to the sleeve assembly and to circumferentially align the obturator assembly relative to the sleeve assembly.

In another aspect, a surgical kit may include a first sleeve assembly defining a longitudinal axis and including a cannula connected to a housing to define a working channel extending axially therethrough, the cannula having a first axial length, a second sleeve assembly defining a longitudinal axis and including a cannula connected to a housing to define a working channel extending axially therethrough, the cannula having a second axial length, wherein the second axial length is less than the first axial length, and an obturator assembly including a handle connected to an elongated obturator, wherein the elongated obturator is sized to pass through the working channel of the first sleeve assembly and the working channel of the second sleeve assembly.

In another aspect, the disclosed trocar assembly may include a sleeve assembly defining a longitudinal axis and including a cannula connected to a housing to define a working channel extending axially therethrough, and an insufflation port in fluid communication with the working channel, an obturator assembly including a handle connected to an elongated obturator, wherein the elongated obturator is sized to pass through the working channel of the sleeve assembly, and an insufflation valve assembly connected to the insufflation port, wherein the insufflation valve assembly includes a valve member received in a housing and a biasing element that biases the valve member relative to the housing.

In another aspect, the disclosed trocar assembly may include a sleeve assembly defining a longitudinal axis and including a cannula connected to a housing to define a working channel extending axially therethrough, and an insufflation port connected to the housing and in fluid communication with the working channel, wherein the insufflation port is moveable relative to the housing between a first configuration, wherein the insufflation port is in fluid communication with the working channel, and a second configuration, wherein the insufflation port is fluidly decoupled from the working channel, and an obturator assembly including a handle connected to an elongated obturator, wherein the elongated obturator is sized to pass through the working channel of the sleeve assembly.

In another aspect, the disclosed trocar assembly may include a sleeve assembly defining a longitudinal axis and including a cannula connected to a housing to define a working channel extending axially therethrough, and an insufflation port in fluid communication with the working channel, an obturator assembly including a handle connected to an elongated obturator, wherein the elongated obturator is sized to pass through the working channel of the sleeve assembly, and a one-way check valve connected to the insufflation port, wherein the check valve is configured to allow fluid flow from the insufflation port to the working channel, while inhibiting fluid flow from the working channel to the insufflation port.

In another aspect, the disclosed trocar sleeve assembly may include a cannula, a housing assembly connected to the cannula to define a working channel extending axially through the trocar sleeve assembly, wherein the housing assembly comprises a housing that defines at least one opening therethrough, the opening being in fluid communication with the working channel, a sleeve slidably received over the housing to define an annular region between the sleeve and the housing, a first sealing member forming a first seal between the sleeve and the housing, and a second sealing member forming a second seal between the sleeve and the housing, the second sealing member being axially spaced from the first sealing member to define a chamber in a portion of the annular region, and an insufflation port in fluid communication with the chamber, wherein the sleeve is slidable relative to the housing between at least a first position, wherein the chamber is in fluid communication with the opening, and a second position, wherein the chamber is fluidly decoupled from the opening.

In another aspect, the disclosed trocar obturator assembly may include an obturator having a open proximal end, a distal end and a penetrating tip disposed at the distal end, wherein the obturator defines a first channel extending from the open proximal end to the penetrating tip, a handle having an open proximal end, an open distal end and defining a second channel extending between the open proximal end and the open distal end, the second channel defining an annular groove, wherein the open distal end of the handle is connected to the open proximal end of the obturator to couple the first channel with the second channel and define an elongated working channel extending therethrough, and a support mechanism received in the annular groove.

In another aspect, the disclosed trocar obturator assembly may include an obturator having a open proximal end, a distal end and a penetrating tip disposed at the distal end, wherein the obturator defines a first channel extending from the open proximal end to the penetrating tip, a handle having an open proximal end, an open distal end and defining a second channel extending between the open proximal end and the open distal end, wherein the open distal end of the handle is connected to the open proximal end of the obturator to couple the first channel with the second channel and define an elongated working channel extending therethrough, and a band having a first end defining a first opening herein and a second end defining a second opening therein, wherein the second end of the band is connected to the open proximal end of the handle such that the first and second openings are coaxially aligned with the working channel.

In another aspect, the disclosed trocar obturator assembly may include an obturator having a open proximal end, a distal end and a penetrating tip disposed at the distal end, wherein the obturator defines a first channel extending from the open proximal end to the penetrating tip, a handle having an open proximal end, an open distal end and defining a second channel extending between the open proximal end and the open distal end, wherein the open distal end of the handle is connected to the open proximal end of the obturator to couple the first channel with the second channel and define an elongated working channel extending therethrough, and a plate pivotally connected to the open proximal end of the handle, the plate defining an opening therein, the opening having a wide end portion and a narrow end portion, wherein the plate is moveable between a first position, wherein the wide end portion of the opening is aligned with the working channel, and a second position, wherein the narrow end portion is aligned with the working channel.

In another aspect, the disclosed trocar obturator assembly may include a sleeve assembly that defines a first working channel, an obturator assembly having a handle connected to an obturator and defining a second working channel extending through the handle and the obturator, wherein the handle defines an opening to the second working channel, and a flexible strap having a first end and a second end, wherein the first end is connected to the sleeve assembly, and wherein the second end defines an opening and is connectable to the obturator assembly such that the opening in the strap is aligned with the opening in the handle.

In another aspect, the disclosed trocar obturator assembly may include an obturator having a open proximal end, a distal end and a penetrating tip disposed at the distal end, wherein the obturator defines a first channel extending from the open proximal end to the penetrating tip, a handle having an open proximal end, an open distal end and defining a second channel extending between the open proximal end and the open distal end, the handle defining a bore that opens into the channel, wherein the open distal end of the handle is connected to the open proximal end of the obturator to couple the first channel with the second channel and define an elongated working channel extending therethrough, and an engagement member received in the bore, wherein the engagement member is biased out of the bore and into the second channel.

In another aspect, the disclosed trocar obturator assembly may include an obturator having a open proximal end, a distal end and a penetrating tip disposed at the distal end, wherein the obturator defines a first channel extending from the open proximal end to the penetrating tip, a handle having an open proximal end, an open distal end and defining a second channel extending between the open proximal end and the open distal end, wherein the open distal end of the handle is connected to the open proximal end of the obturator to couple the first channel with the second channel and define an elongated working channel extending therethrough, an engagement member pivotally connected to the handle and including a first end and a second end, and a biasing element positioned to bias the first end of the engagement member into the second channel.

In another aspect, the disclosed trocar assembly may include an obturator assembly including a handle connected to an elongated obturator, the handle including a radially inward extending projection, and a sleeve assembly defining a longitudinal axis and a working channel extending axially through the sleeve assembly, the sleeve assembly further including a radially outward extending projection, wherein the inward extending projection is snap fit over the outward extending projection when the elongated obturator is fully received in the working channel.

In another aspect, the disclosed trocar assembly may include an obturator assembly including a handle connected to an elongated obturator, the handle including an L-shaped projection having an axial portion and a radial portion, and a sleeve assembly defining a longitudinal axis and a working channel extending axially through the sleeve assembly, the sleeve assembly further defining a locking groove having an opening and an undercut groove extending partially circumferentially from the opening, wherein, when the L-shaped projection is received in the undercut groove, the obturator assembly is releasably connected to the sleeve assembly and circumferentially aligned with the sleeve assembly.

In another aspect, the disclosed trocar assembly may include an obturator assembly including a handle connected to an elongated obturator, a distal end of the handle further including hook-shaped projection extending therefrom, and a sleeve assembly defining a longitudinal axis and a working channel extending axially through the sleeve assembly, a proximal end of the sleeve assembly further including a radial projection, wherein the hook-shaped projection is configured to releasably engage the radial projection to connect the obturator assembly to the sleeve assembly and to circumferentially align the obturator assembly with the sleeve assembly.

Other aspects of the disclosed trocar assembly will become apparent from the following description, the accompanying drawings and the appended claims.

BRIEF DESCRIPTION OF THE DRAWINGS

FIG. 49 is an upward looking, partially exploded, perspective view of the trocar assembly of FIG. 48;

FIG. 50 is a downward looking, partially exploded, perspective view of the trocar assembly of FIG. 48;

DETAILED DESCRIPTION

Figure 1A:
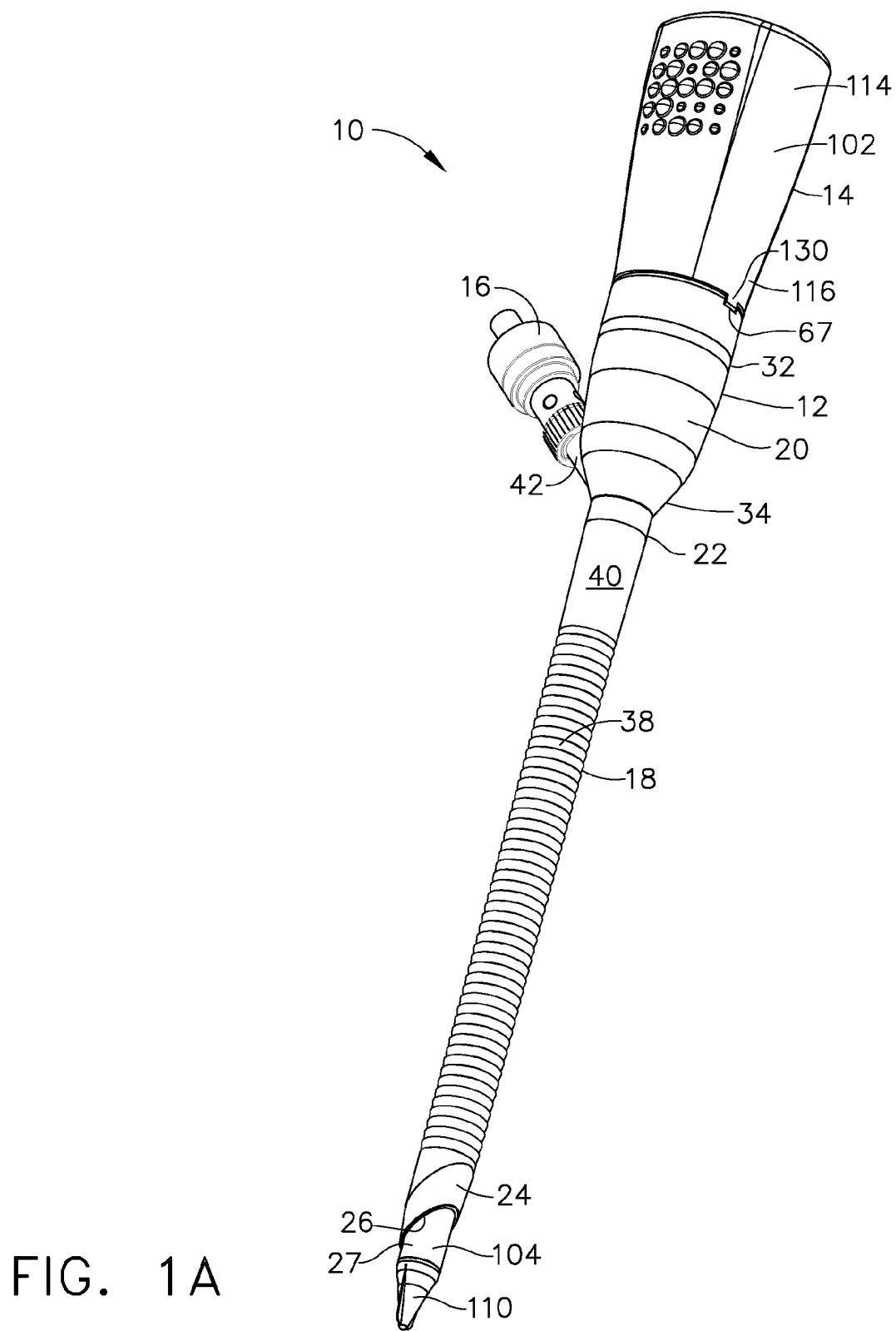
FIG. 1A is a front perspective view of one embodiment of the disclosed trocar assembly, wherein the trocar assembly includes an insufflation valve assembly in accordance with a first aspect of the disclosure.
Figure 1B:
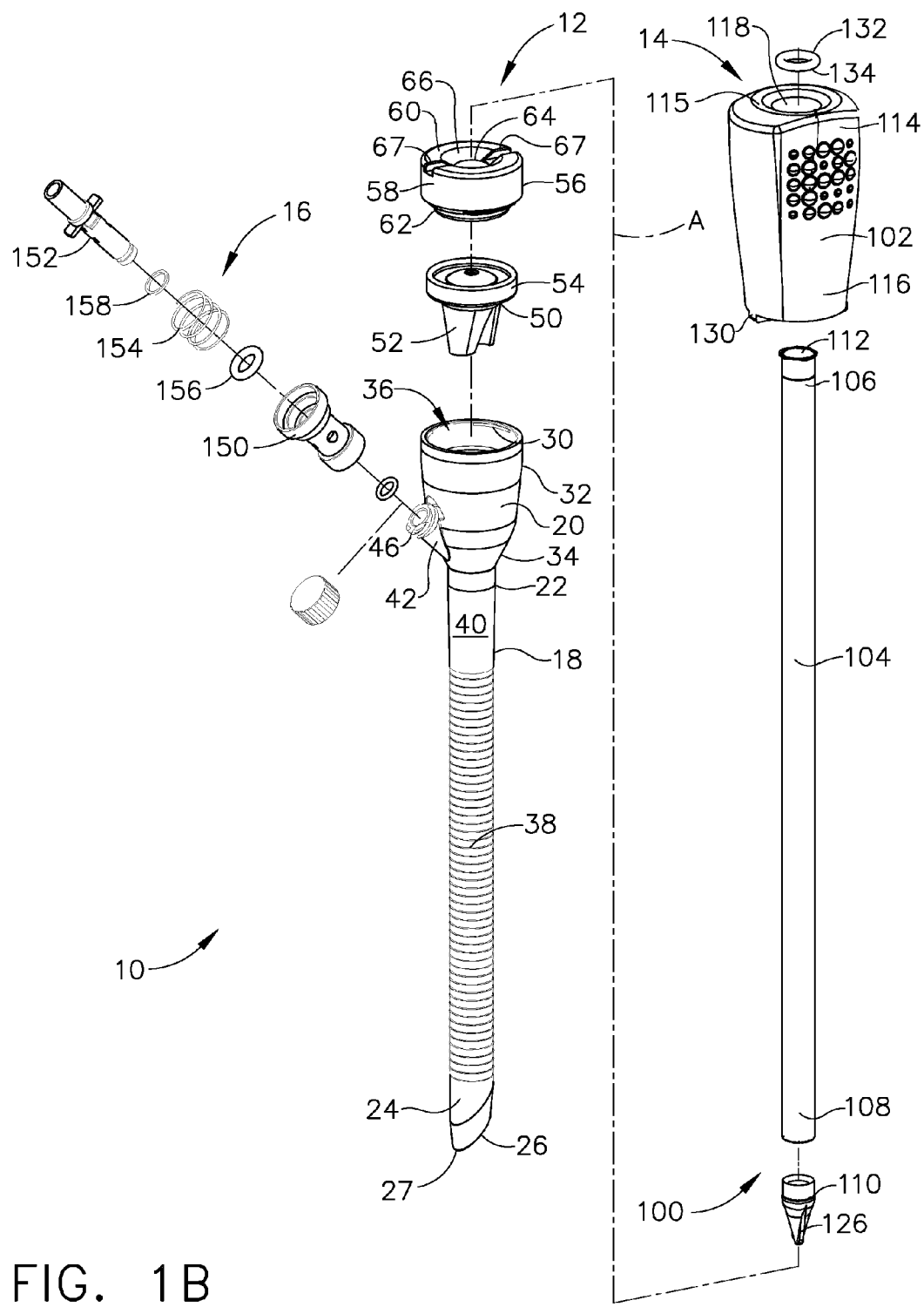
FIG. 1B is an exploded perspective view of the trocar assembly of FIG. 1A.
Figure 1C:
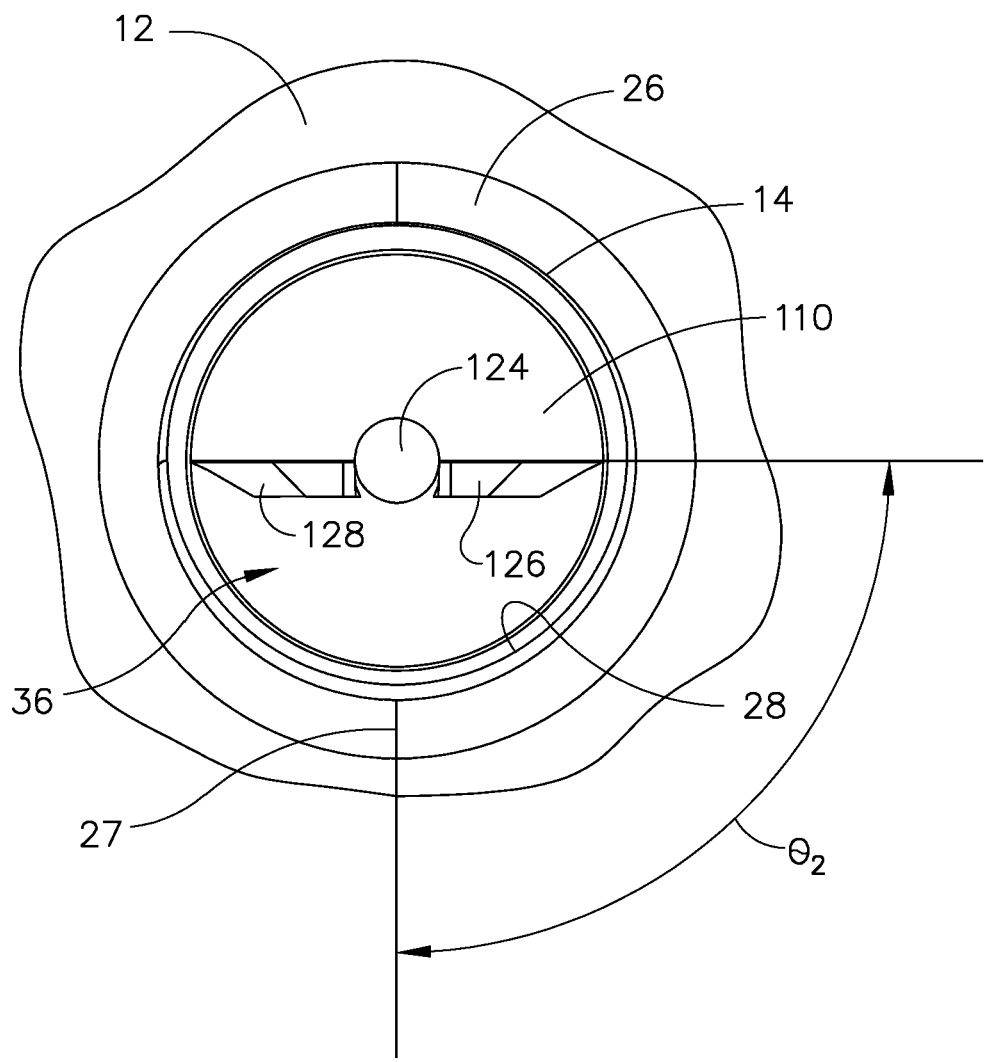
FIG. 1C is an end elevational view of the trocar assembly of FIG. 1A.

Referring to FIGS. 1A, 1B and 1C, one embodiment of the disclosed trocar assembly, generally designated 10, may include a sleeve assembly 12 and an obturator assembly 14. Optionally, as will be discussed in greater detail below, the trocar assembly 10 may additionally include an insufflation valve assembly 16 coupled to the sleeve assembly 12.

The sleeve assembly 12 may include a generally cylindrical or tubular cannula 18, a generally annular housing 20, a channel seal 50 received in the housing 20 and a cap 56 attached to the housing 20. The cannula 18 may be elongated along a longitudinal axis A, and may include an open proximal end 22 and an open distal end 24. The open distal end 24 may included a bevel 26 that terminates in a pointed tip 27. A lumen 28 (FIG. 1C) may extend along the axial length of the cannula 18 between the open proximal end 22 and the open distal end 24. The housing 20 may define an internal volume 30 and may include an open proximal end 32 and an open distal end 34. The open distal end 34 of the housing 20 may be connected to the open proximal end 22 of the cannula 18 to couple the internal volume 30 of the housing 20 with the lumen 28 of the cannula 18, thereby defining an elongated working channel 36 that extends axially through the sleeve assembly 12.

Optionally, the sleeve assembly 12 may include a plurality of stability grooves 38 formed in or connected to an outer surface 40 of the cannula 18. The stability grooves 38 may be configured to engage the abdominal wall 148 (FIG. 58) of a patient to resist undesired axial movement (e.g., withdrawal) of the sleeve assembly 12 relative to the abdominal wall. For example, the stability grooves 38 may be axially consecutive, circumferential, distally tapered ridges extending along a portion of the outer surface 40 of the cannula 18.

Figure 2:
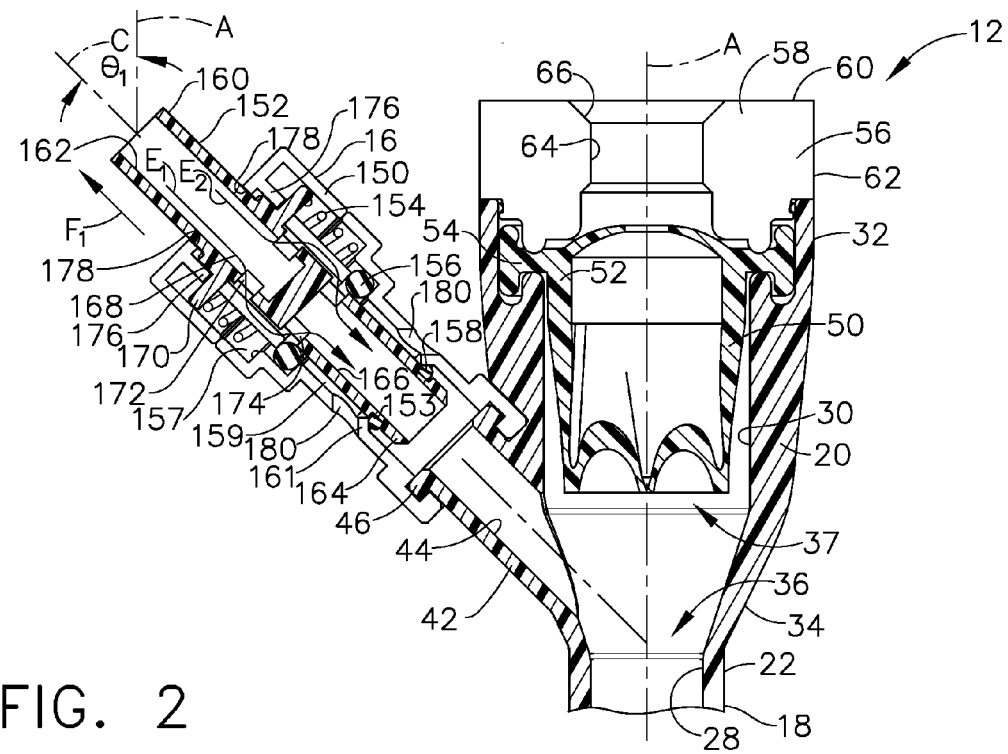
FIG. 2 is a front elevational view, in section, of a portion of the sleeve assembly of the trocar assembly of FIG. 1A, wherein the insufflation valve assembly is shown in an insufflating configuration.

Referring to FIG. 2, an insufflation port 42 may extend outwardly from the housing 20 of the sleeve assembly 12 and may define a channel 44 that is in fluid communication with the working channel 36 of the sleeve assembly 12. The insufflation port 42 may extend proximally and at an angle $\theta_1$ (e.g., 45 degrees) to the longitudinal axis A of the sleeve assembly 12. While the insufflation port 42 is shown in FIG. 2 as extending from the housing 20, those skilled in the art will appreciate that the insufflation port 42 may alternatively extend from the cannula 18 or other portions of the sleeve assembly 12, such as the cap 56.

Figure 3:
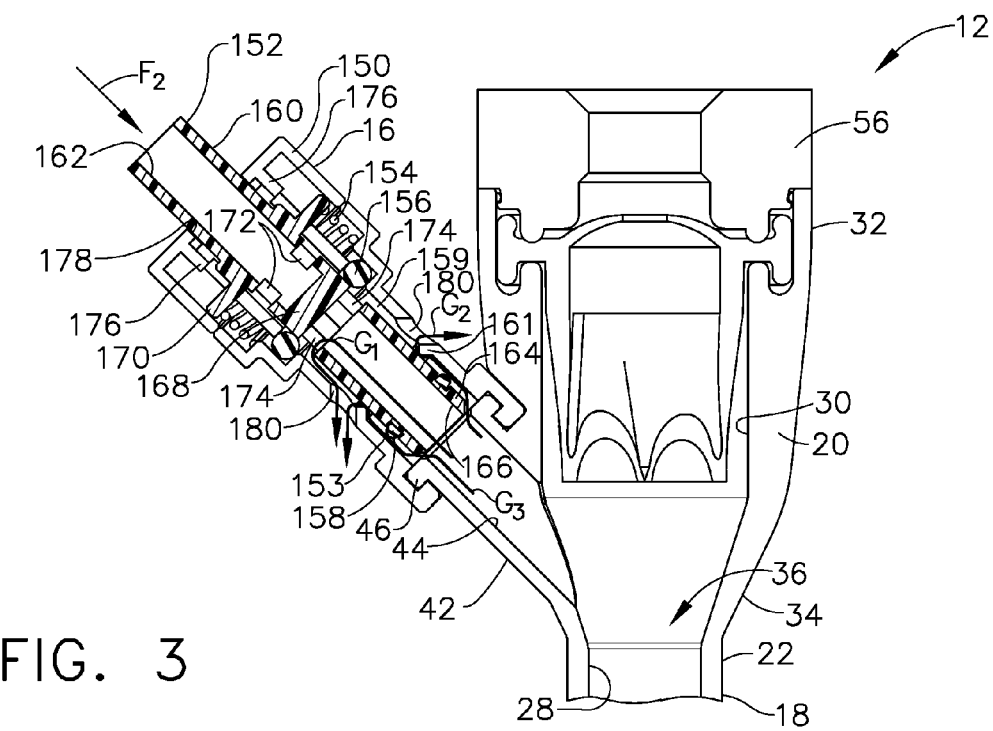
FIG. 3 is a front elevational view, in section, of the sleeve assembly of FIG. 2, wherein the insufflation valve assembly is shown in a venting configuration.
Figure 4:
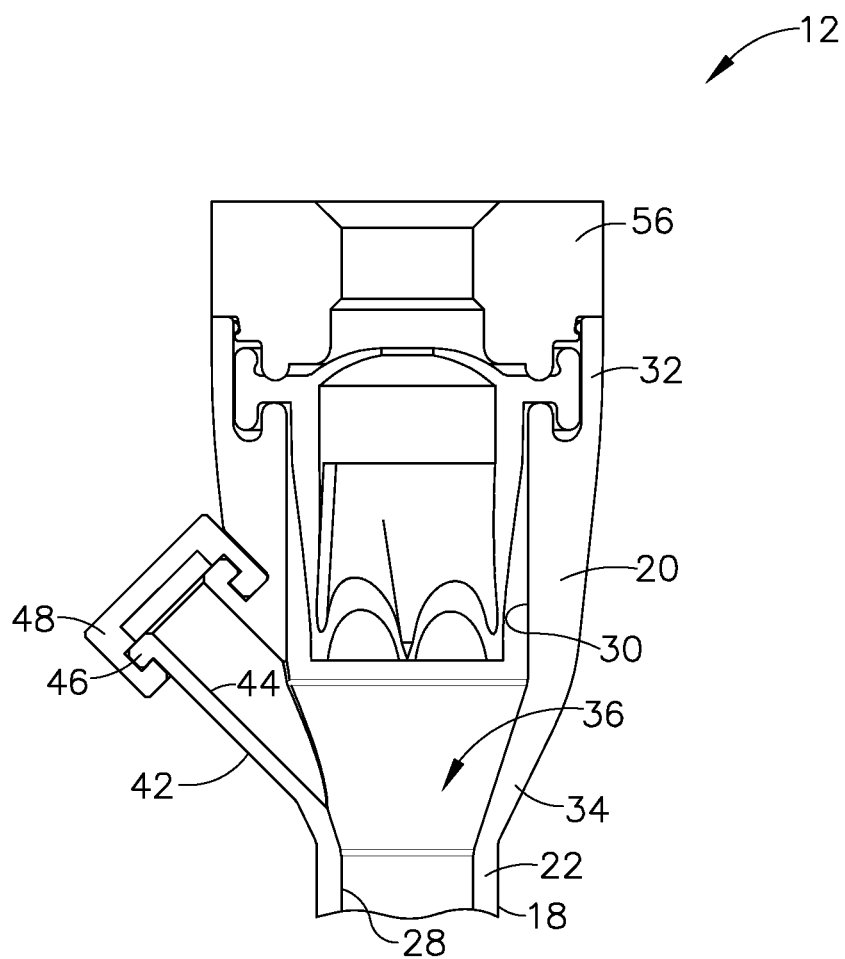
FIG. 4 is a front elevational view, in section, of the trocar assembly of FIG. 1, wherein the insufflation valve assembly has been removed and replaced with a cap to seal the insufflation port in accordance with a second aspect of the disclosure.

The insufflation port 42 may include an optional lip 46 to facilitate coupling the insufflation valve assembly 16 (or a tube or hose) thereto, as shown in FIGS. 2 and 3, to facilitate the flow of an insufflation fluid (e.g., carbon dioxide gas) to insufflate the abdomen via the sleeve assembly 12. Alternatively, threads or the like may be used in place of, or in addition to, the lip 46. As shown in FIG. 4, when the insufflation port 42 is not in use, a sealing member 48, such as a cap or a plug may be coupled to the insufflation port 42 to seal the channel 44.

Figure 23:
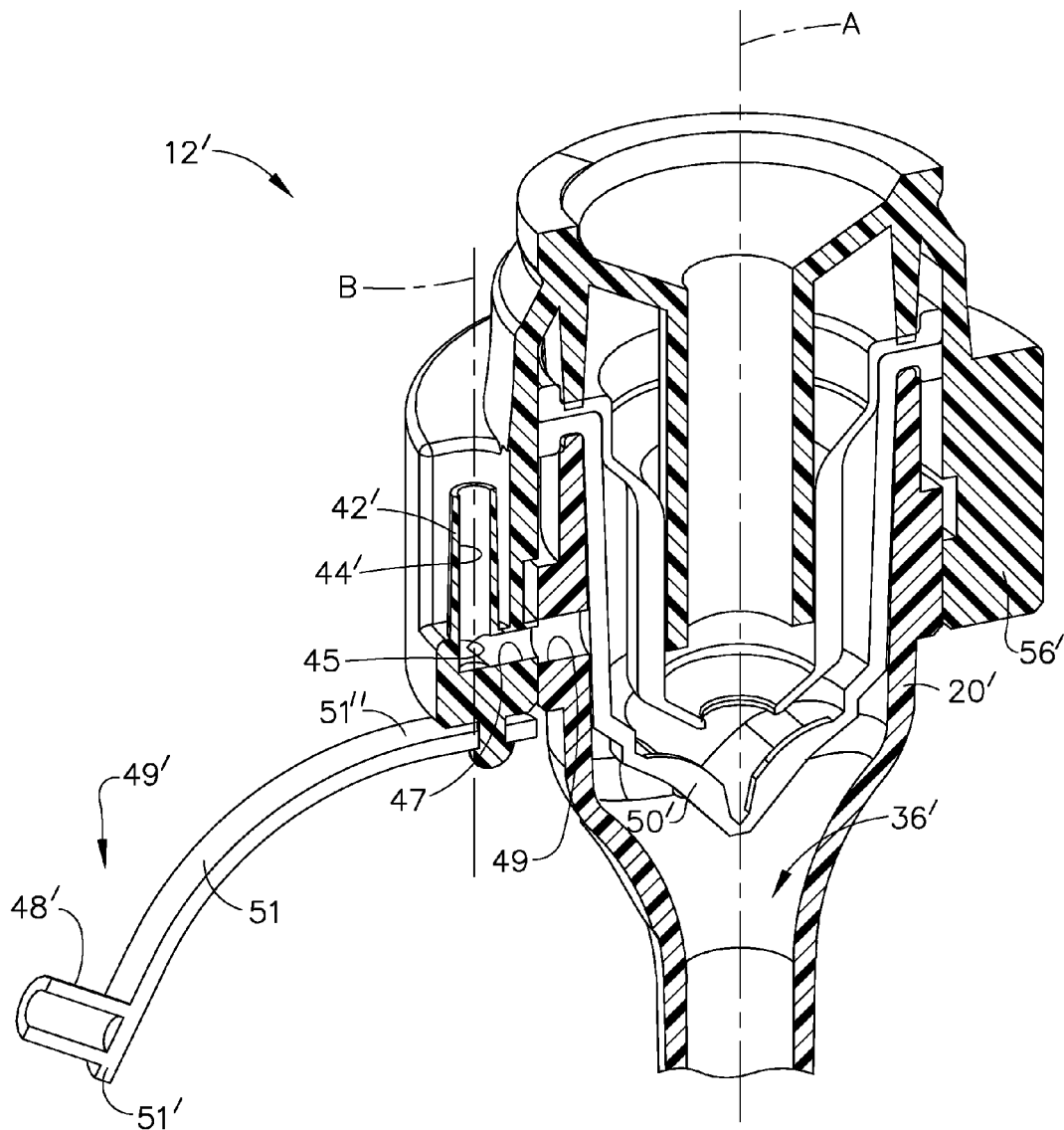
FIG. 23 is a front perspective view, in section, of a portion of a trocar sleeve assembly having an insufflation port configured in accordance with a first aspect of the disclosure.

Referring to FIG. 23, in a first alternative aspect, the sleeve assembly 12' may include an insufflation port 42' having an axial portion 45 that has a longitudinal axis B that is generally parallel with the longitudinal axis A of the sleeve assembly 12'. Those skilled in the art will appreciate that a generally parallel insufflation port 42' may reduce the overall profile and size of the sleeve assembly 12' when the sleeve assembly 12' is connected to an insufflation fluid supply since the insufflation fluid supply may be connected at or near the top of the sleeve assembly 12', thereby eliminating any obstruction on the side of the sleeve assembly 12'.

A sealing member 49' may be provided to seal the insufflation port 42'. The sealing member 49' may include a plug 48' disposed at a first end 51' of a band 51, while the second end 51" of the band 51 may be connected to the cap 56'. The plug 48' may seal the insufflation port 42' may sliding over the insufflation port.

Still referring to FIG. 23, in one particular implementation of the first alternative aspect, the sleeve assembly 12' may include a housing 20' and a cap 56' coupled to the housing 20' to enclose a channel seal 50' therein. The insufflation port 42' may include a channel 44' that includes an axial portion 45 and a radial portion 47 defined by the cap 56', which may be in fluid communication with a radial channel 49 defined by the housing 20', thereby coupling the insufflation port 42' with the working channel 36' of the sleeve assembly 12'. The insufflation source (e.g., a rubber tube) may slide coaxially over the insufflation port 42'.

Figure 24:
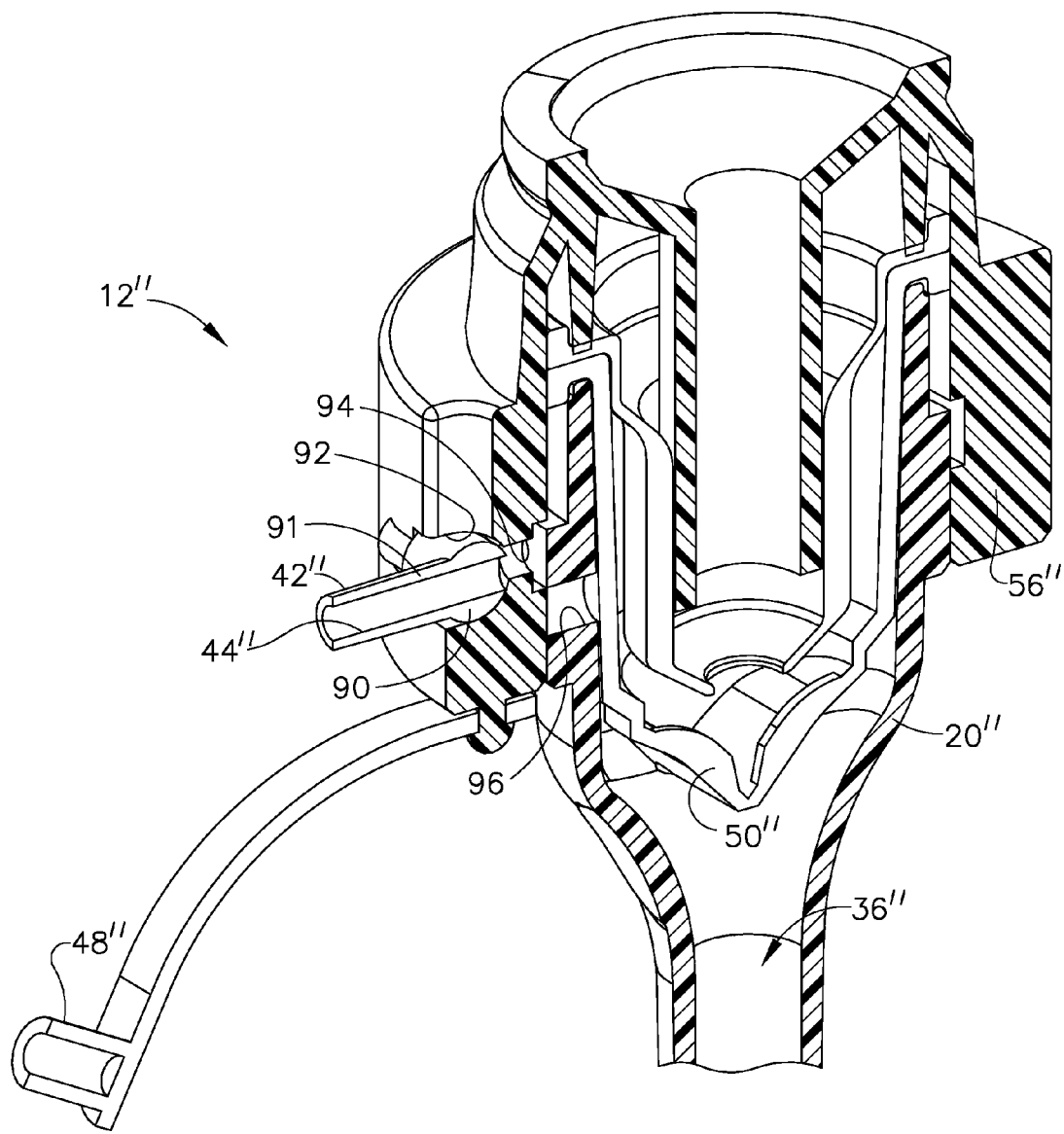
FIG. 24 is a front perspective view, in section, of a portion of a trocar sleeve assembly having a pivoting insufflation port in accordance with a second aspect of the disclosure, wherein the insufflation port is shown in a first, radial configuration.
Figure 25:
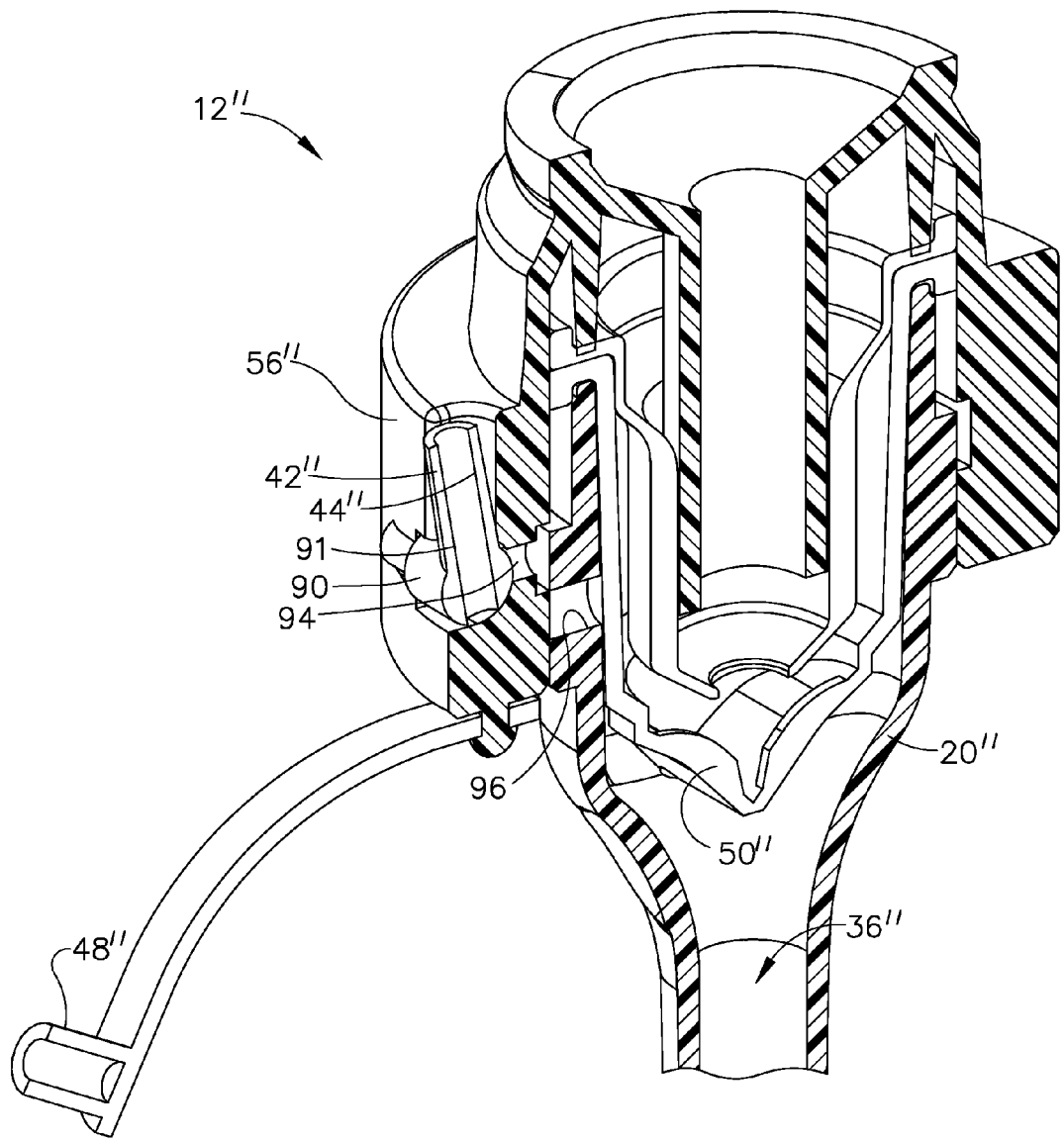
FIG. 25 is a front perspective view, in section, of the sleeve assembly of FIG. 24, wherein the insufflation port is shown in a second, axial configuration.

Referring to FIGS. 24 and 25, in a second alternative aspect, the sleeve assembly 12" may include a insufflation port 42" configured to pivot between a first configuration (FIG. 24) and a second configuration (FIG. 25). As one example, the insufflation port 42" may pivot between a first, open radial configuration and a second, closed axial configuration. As another example, the insufflation port 42" may pivot between a first, open radial configuration and a second, open axial configuration. In this case, the socket 92 (described below) would have to be modified such that the channel 44" of the insufflation port 42" is always in fluid communication with the channel working channel 36" of the sleeve assembly 12". A sealing member 48" may be provided to seal the insufflation port 42".

Still referring to FIGS. 24 and 25, in one particular implementation of the second alternative aspect, the sleeve assembly 12" may include a housing 20" and a cap 56" coupled to the housing 20" to enclose a channel seal 50" therein. The insufflation port 42" may define a channel 44" and may include a ball portion 90 disposed at a distal end 91 thereof. The cap 56" may define a socket 92 and a channel 94 extending from the socket 92. The housing 20" may define a channel 96 that fluidly couples the channel 94 of the cap 56" with the working channel 36" of the sleeve assembly 12".

In the assembled configuration, the ball portion 90 of the insufflation port 42" may be received in the socket 92 of the cap 56". Therefore, in the open configuration shown in FIG. 24, the channel 44" of the insufflation port 42" may be in communication with the channel 94 defined by the cap 56" and, ultimately the working channel 36" of the sleeve assembly 12". However, as shown in FIG. 25, when the insufflation port 42" is pivoted away from the radial configuration shown in FIG. 24, the channel 44" of the insufflation port 42" may be fluidly isolated from the channel 44" defined by the cap 56" and, therefore, may be fluidly decoupled from the working channel 36" of the sleeve assembly 12".

Figure 26:
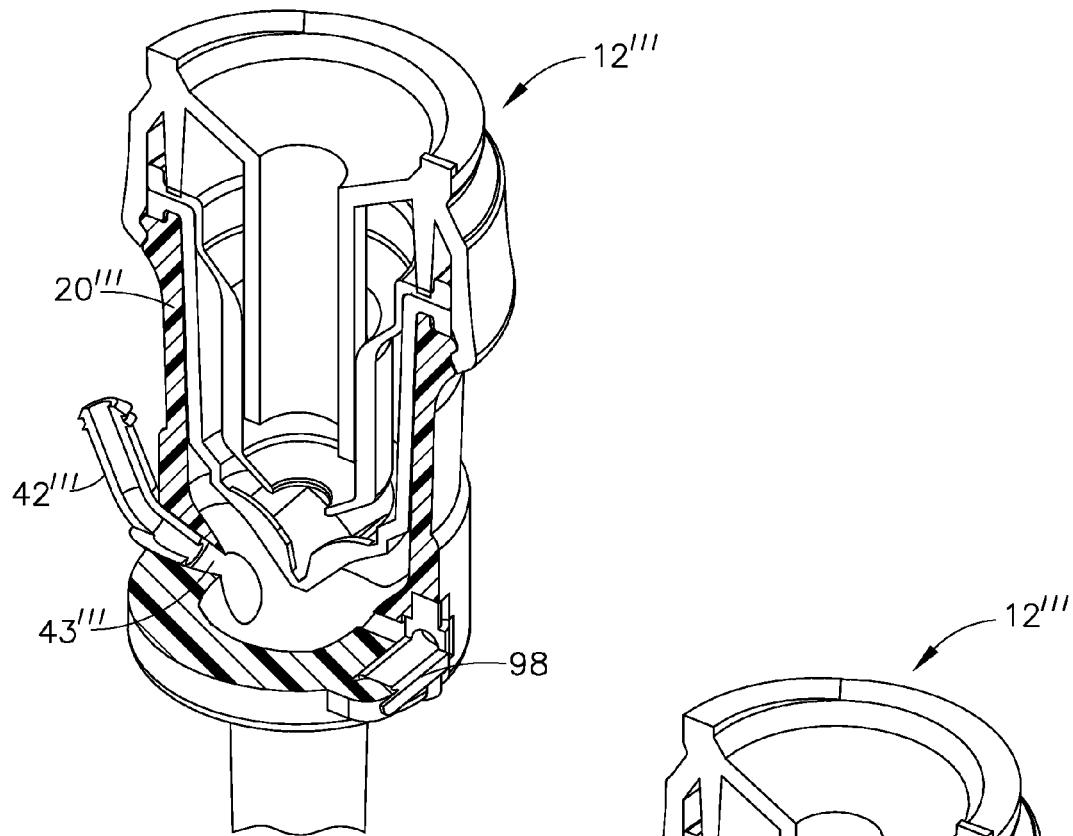
FIG. 26 is a front perspective view, in section, of a portion of a trocar sleeve assembly having a second insufflation port in accordance with a third aspect of the disclosure, wherein the second insufflation port is shown in a first, stowed configuration.
Figure 27:
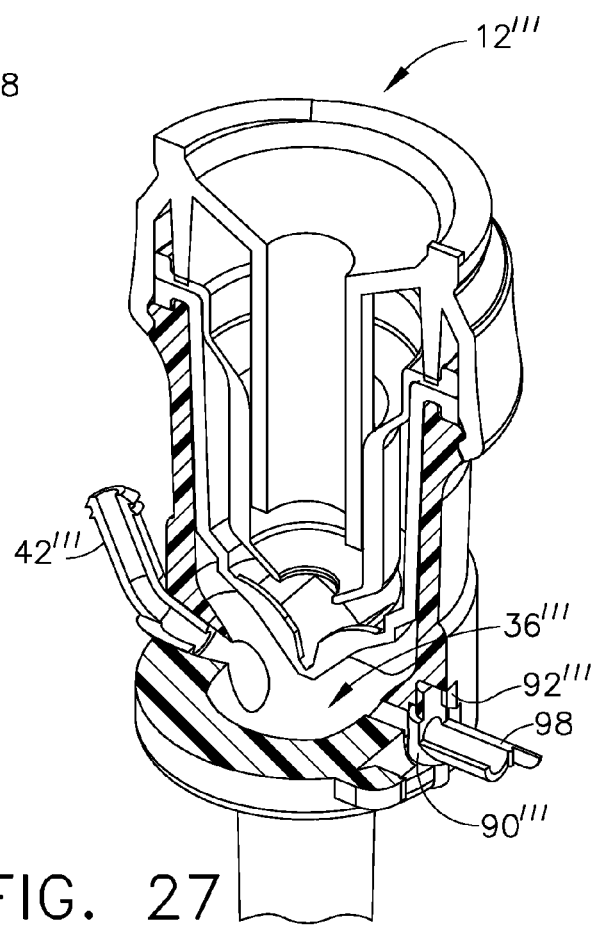
FIG. 27 is a front perspective view, in section, of the sleeve assembly of FIG. 26, wherein the second insufflation port is shown in a second, deployed configuration.

Referring to FIGS. 26 and 27, in a third alternative aspect, the sleeve assembly 12''' may include two or more insufflation ports 42''', 98. The first insufflation port 42''' may be configured as shown in FIG. 2. Alternatively, as shown in FIGS. 26 and 27, the first insufflation port 42''' may be press fit into a bore 43''' defined by the housing 20'''. The second insufflation port 98 may be a pivoting insufflation port as shown in FIGS. 24 and 25. Alternatively, as shown in FIGS. 26 and 27, the second insufflation port 42''' may include a generally cylindrical ball portion 90''' and a generally cylindrical socket 92''', wherein the insufflation port 42''' is in fluid communication with the working channel 36''' only when the cylindrical ball portion 90''' is at a particular position relative to the cylindrical socket 92'''.

Figure 59:
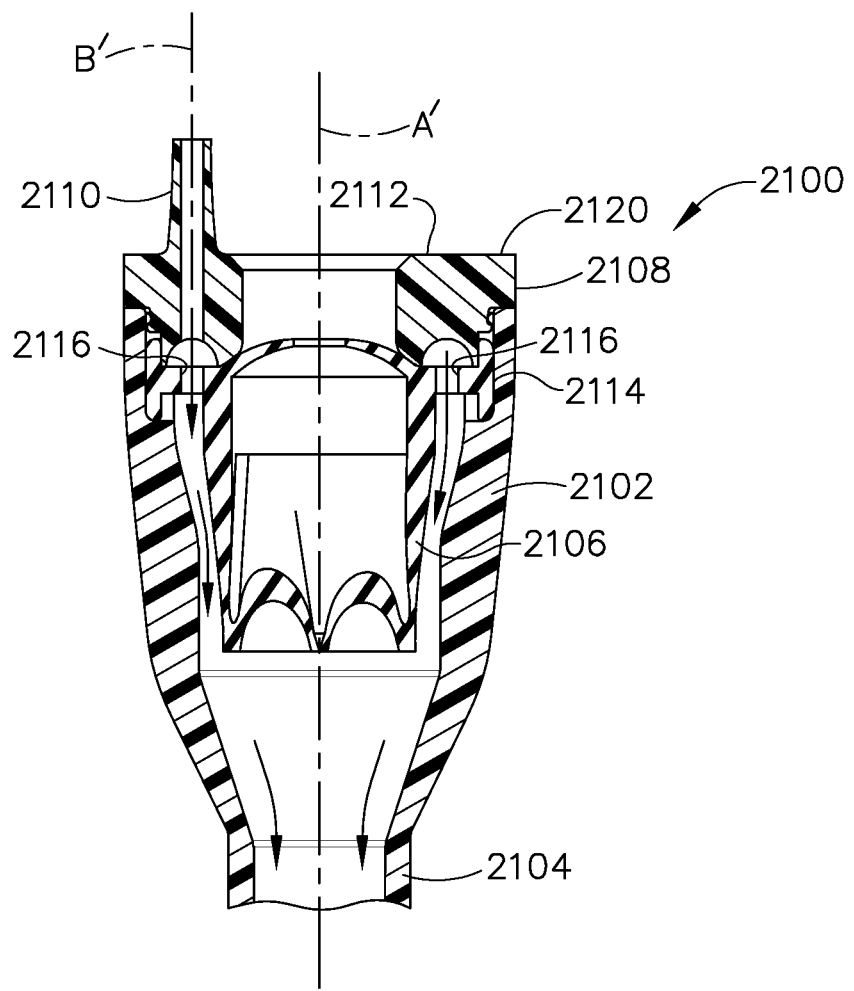
FIG. 59 is a front elevational view, in section, of a portion of a trocar sleeve assembly having an insufflation port configured in accordance with a another aspect of the disclosure.

Referring to FIG. 59, in a fourth alternative aspect, the sleeve assembly 2100 may include a housing 2102, a cannula 2104, a channel seal 2106, a cap 2108 and an insufflation port 2110. The insufflation port 2110 may extend from the proximal end 2112 of the cap 2108 and may have a longitudinal axis B' that is generally parallel with the longitudinal axis A' of the sleeve assembly 2100. The channel seal 2106 may include a flange 2114 positioned between the housing 2102 and the cap 2108 to seal the proximal end 2120 of the sleeve assembly 2100. The flange 2114 of the channel seal 2106 may define openings 2116 that fluidly couple the insufflation port 2110 with the internal volume 2118 of the housing 2102.

To this point, the various insufflation ports have been described as being in fluid communication with the working channel of the sleeve assembly, such that the sleeve assembly defines the insufflation fluid pathway into the abdominal cavity. However, those skilled in the art will appreciate that a designated insufflation fluid channel may be used, wherein the designated insufflation fluid channel may be separate from the working channel. For example, while not shown, the designated insufflation fluid channel may extend through the walls of the housing and cannula.

Referring to FIGS. 1B and 2, the channel seal 50 of the sleeve assembly 12 may be received in the internal volume 30 of the housing 20 to seal the proximal end 37 of the working channel 36, while permitting medical instruments to be inserted through the channel seal 50 and into the working channel 36. The channel seal 50 may include a body 52 and a flange 54 extending outward from the body 52. Therefore, in one particular aspect, the channel seal 50 may be secured in the internal volume 30 of the housing 20 by compressing the flange 54 between the housing 20 and the cap 56 and securing the cap 56 relative to the housing 20.

The cap 56 may include a body 58 having an open proximal end 60 and an open distal end 62. An opening 64 may extend from the open proximal end 60 of the body to the open distal end 62, and may be in communication with the proximal end 37 of the working channel 36. The proximal end 60 of the body 58 may define a beveled guide surface 66 configured to direct medical instruments (not shown) to the opening 64 in the cap 56 and, ultimately, to the working channel 36 of the sleeve assembly 12. Additionally, the proximal end 60 of the body 58 may define an axial groove 67 that extends radially outward from the opening 64.

The cap 56 may be secured to the housing 20 with adhesives, ultrasonic welding, snap fit or the like, thereby securing the channel seal 50 within the internal volume 30 of the housing 20. Alternatively, the cap 56 may be integral with the housing 20.

Figure 28:
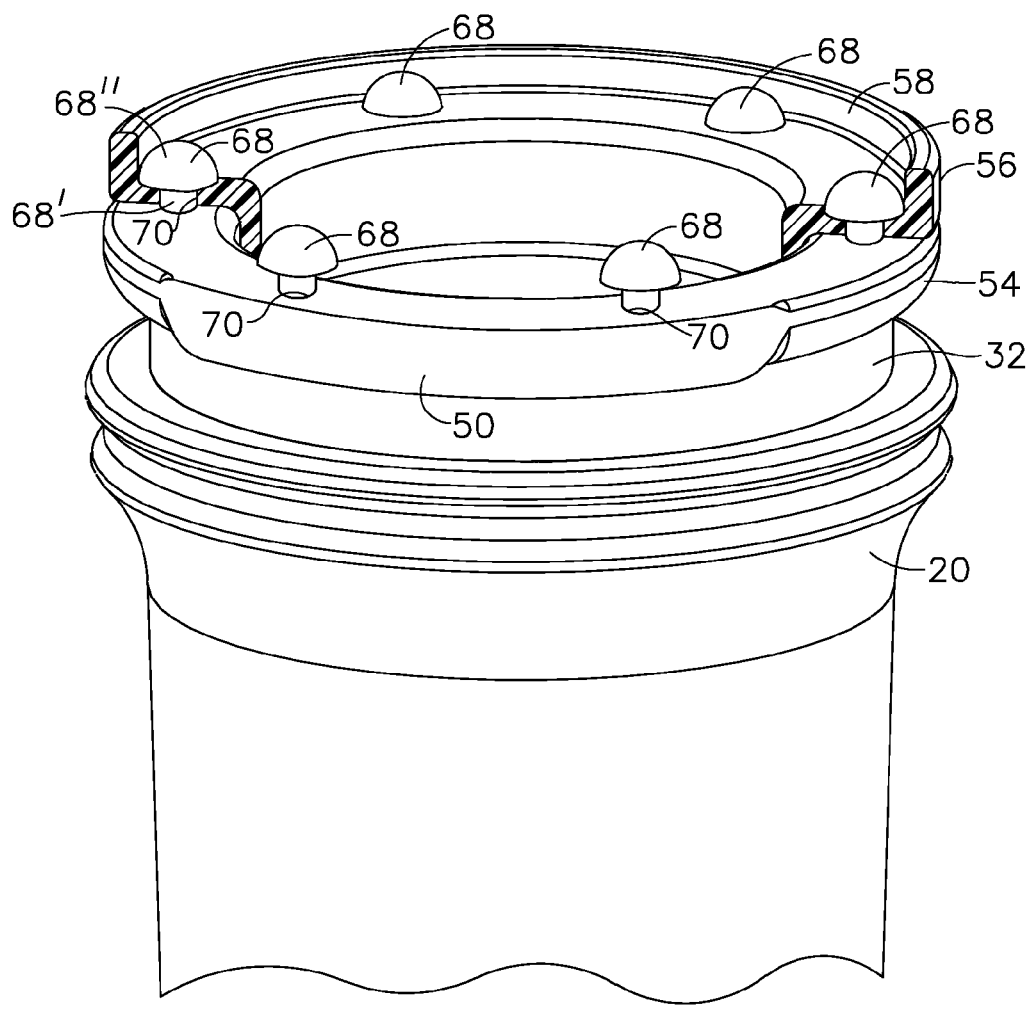
FIG. 28 is a front perspective view of a cap connected to the sleeve assembly of the trocar assembly in accordance with one alternative aspect of the disclosure.

In one alternative aspect, shown in FIG. 28, the housing 20 may include a plurality of mushroom-shaped projections 68 extending proximally from the proximal end 32 of the housing 20. Each mushroom-shaped projection 68 may include a stem 68' and a head 68" disposed at the end of the stem 68'. The body 58 of the cap 56 may include a plurality of openings 70 aligned with the projections 68 extending from the housing 20 such that the cap 56 may be snapped onto the housing 20 to secure the flange 54 of the channel seal 50 therebetween. The heads 68" of the projections 68 may be larger than the openings 70 in the cap 56. The projections 68 and/or the cap 56 may be constructed from a pliable material such that the heads 68" of the projections may be urged through the smaller openings 70 and may then spring back to shape to lock the cap 56 onto the housing 20.

Figure 57:
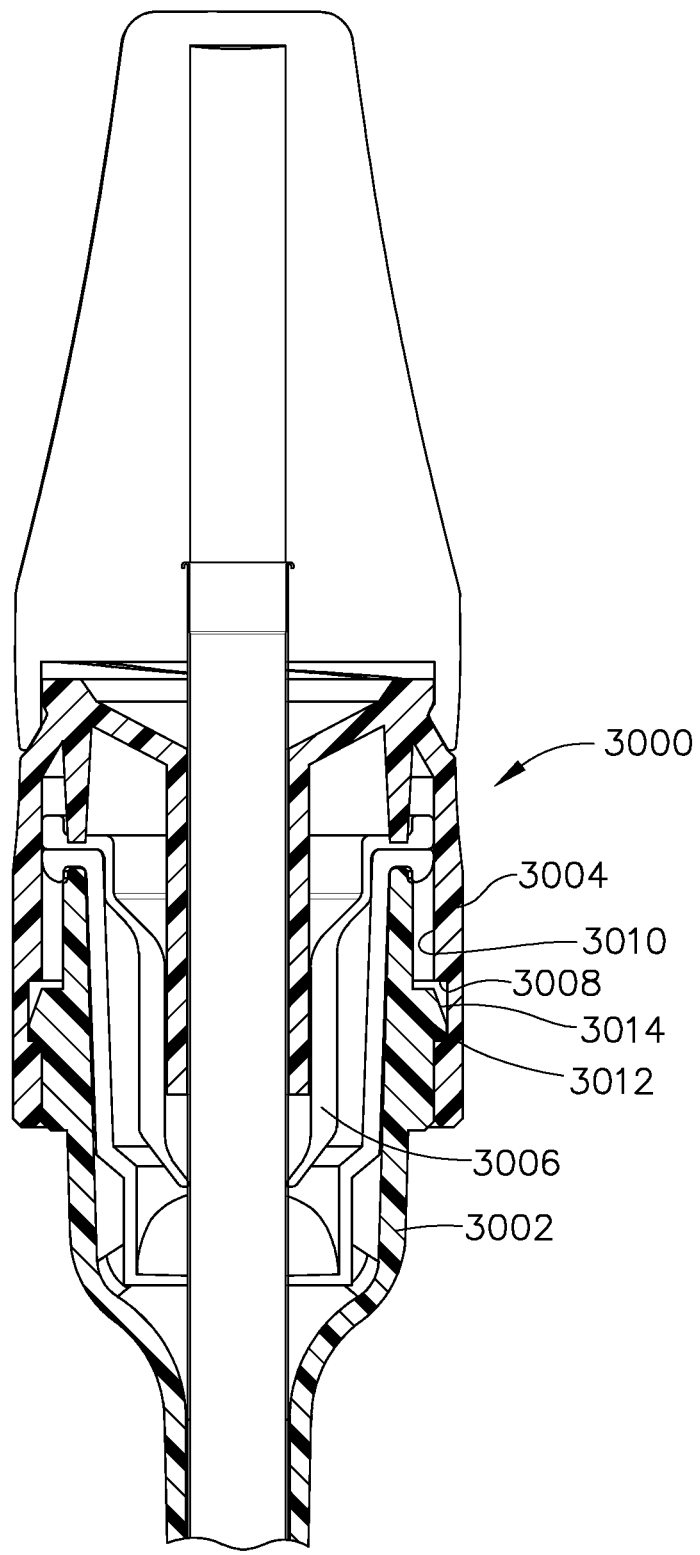
FIG. 57 is a front elevational view, in section, of a cap connected to the sleeve assembly of the trocar assembly in accordance with another alternative aspect of the disclosure.

In another alternative aspect for attaching the cap to the housing, shown in FIG. 57, a sleeve assembly 3000 may include a housing 3002, a cap 3004 and a channel seal 3006. The cap 3004 may define a groove 3008 in an inner surface 3010 thereof. The housing 3002 may include a circumferentially extending projection 3012 having a proximally tapering surface 3014. The cap 3004 may be coaxially received over the housing 3002 and urged in the distal direction (i.e., axially downward) relative to the housing 3002 until the circumferentially extending projection 3012 is received in the groove 3008, thereby securing the cap 3004 to the housing 3002 and enclosing the channel seal 3006 within the housing 3002 with a snap action.

Figure 60:
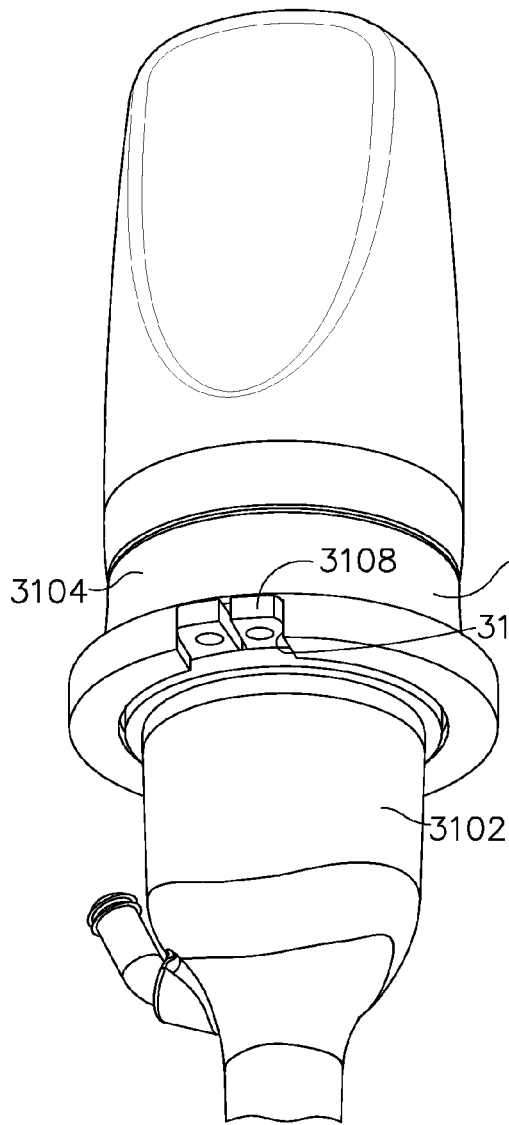
FIG. 60 is a front perspective view of a cap connected to a sleeve assembly of a trocar assembly in accordance with yet another aspect of the disclosure.
Figure 61:
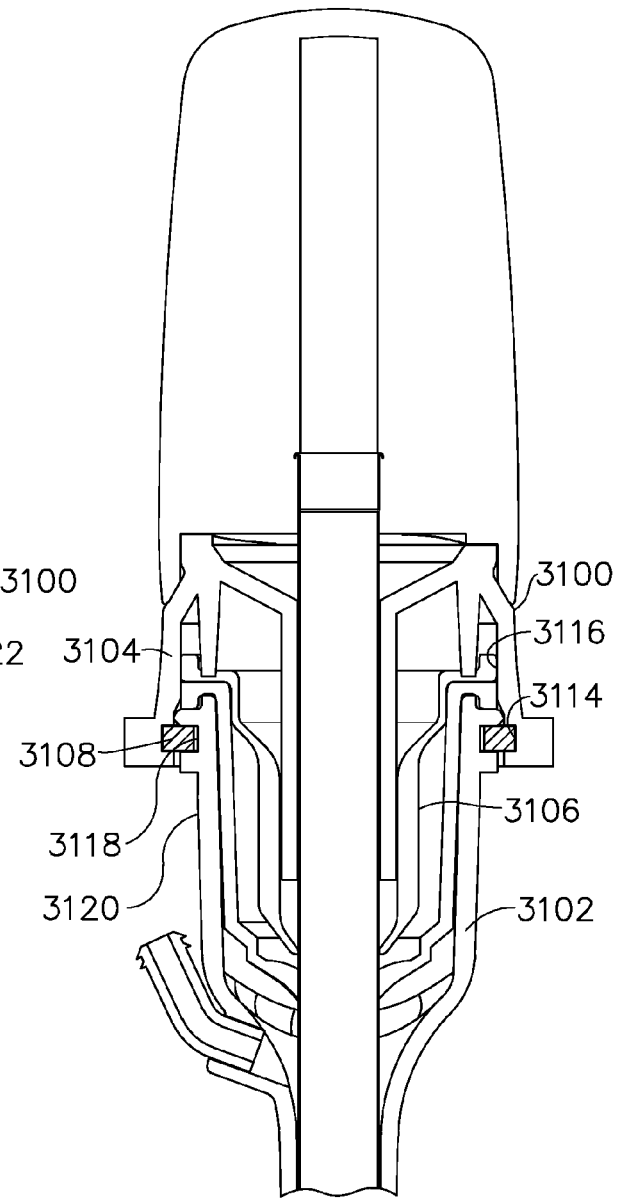
FIG. 61 is front elevational view, in section, of the trocar assembly of FIG. 60.
Figure 62:
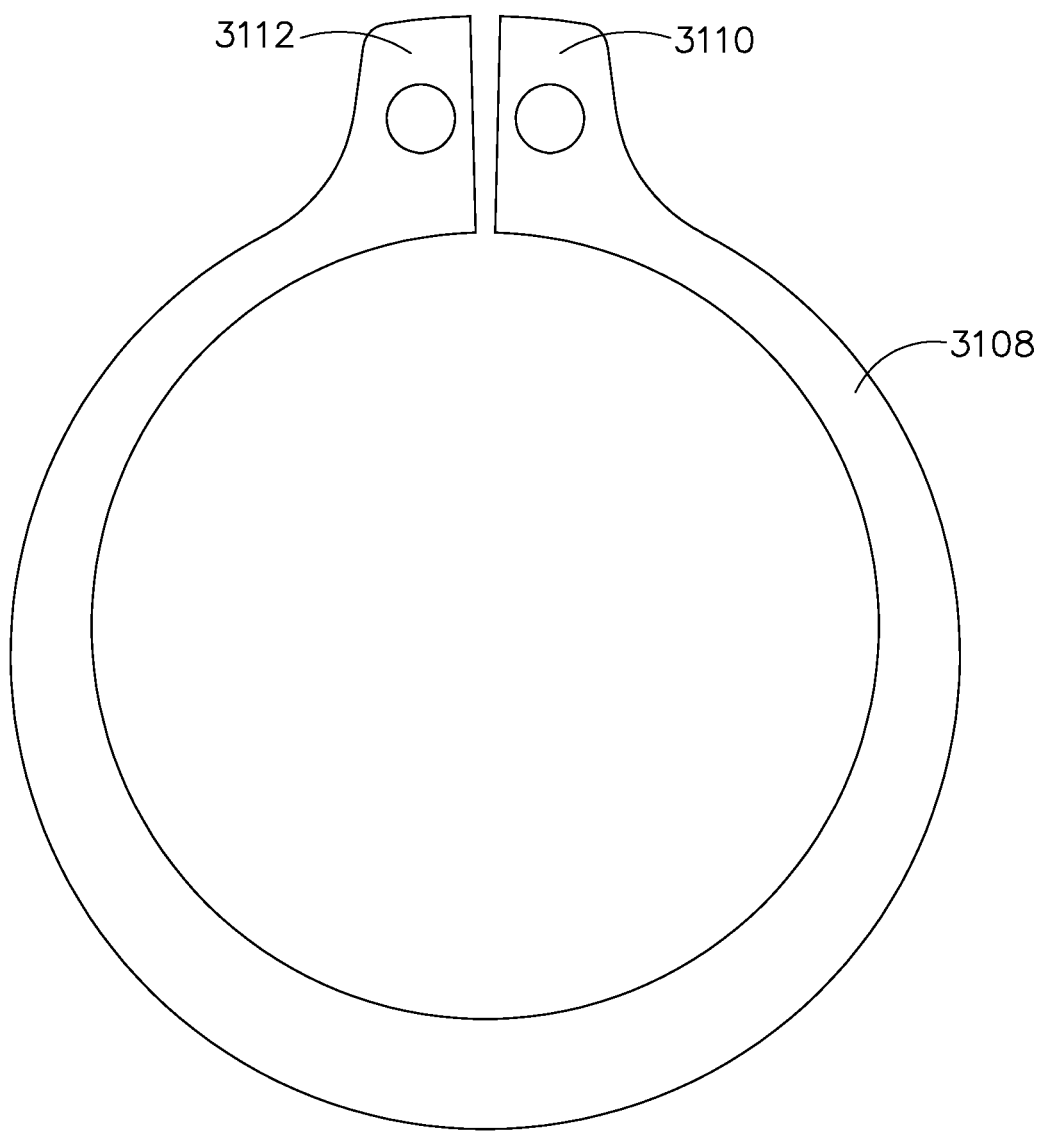
FIG. 62 is a top plan view of a retaining ring of the trocar assembly of FIG. 61.

Referring to FIGS. 60-62, in yet another alternative aspect for attaching the cap to the housing, a sleeve assembly 3100 may include a housing 3102, a cap 3104, a channel seal 3106 and a retaining ring 3108. The retaining ring 3108 may be biased to a particular internal diameter, but may be compressed to a smaller internal diameter by, for example, applying a squeezing force to optional tabs 3110, 3112 positioned at opposite ends of the retaining ring 3108.

The cap 3104 may define a circumferential groove 3114 in an inner surface 3116 thereof. The housing 3102 may define a circumferential groove 3118 in an outer surface 3120 thereof. The retaining ring 3108 may be received within both the groove 3114 in the cap 3104 and the groove 3118 in the housing 3102 to secure the cap 3104 to the housing 3102. A opening 3122 in the cap 3104 may provide access to the tabs 3110, 3112 of the retaining ring 3108.

Figure 21:
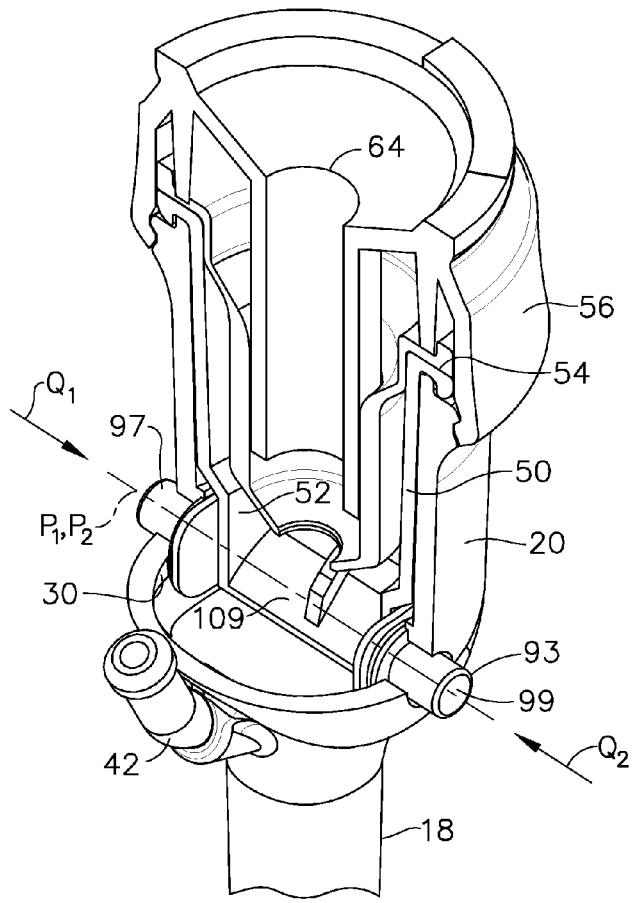
FIG. 21 is a front perspective view, in section, of a portion of a trocar sleeve assembly having an insufflation valve assembly in accordance with a eleventh aspect of the disclosure.
Figure 22:
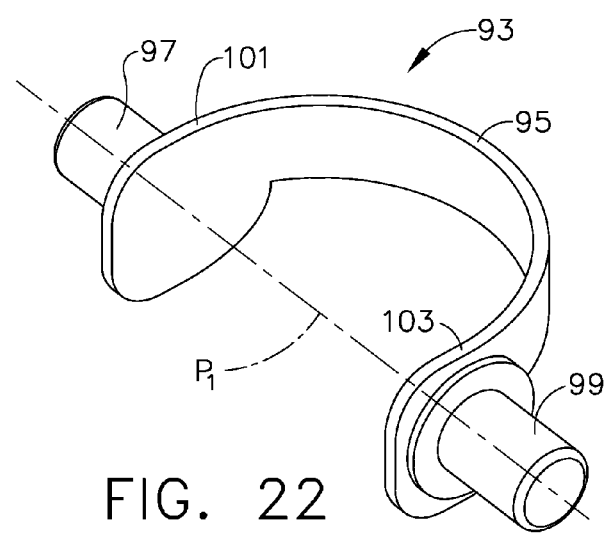
FIG. 22 is a front perspective view of the venting mechanism of the insufflation valve assembly shown in FIG. 21.

Referring back to FIGS. 1B and 2, in one particular aspect, the channel seal 50 may be a septum cum duckbill-type check. Optionally, as shown in FIGS. 21 and 22, a pinching member 93 may be received in the internal volume 30 of the housing 20. The pinching member 93 may include a spring-loaded, semi-circular body 95 having a first push tab 97 disposed at a first end 101 of the body 95 and a second push tab 99 disposed at a second end 103 of the body 95. The body 95 may bias the first push tab 97 radially outward through a first opening 105 in the housing 20 and the second push tab 99 radially outward through a second opening 107 in the housing 20. A longitudinal axis $P_1$ of the push tabs 97, 99 may be coaxially aligned with the longitudinal axis $P_2$ of the duckbill portion 109 of the channel seal 50. Therefore, when a force (arrows $Q_1$, $Q_2$) is applied to the push tabs 97, 99, such as a manual force applied between the thumb and forefinger, the push tabs 97, 99 compress the duckbill portion 109 of the channel seal 50, thereby partially opening the channel seal 50 to allow insufflation fluid to vent therethrough.

Figure 63:
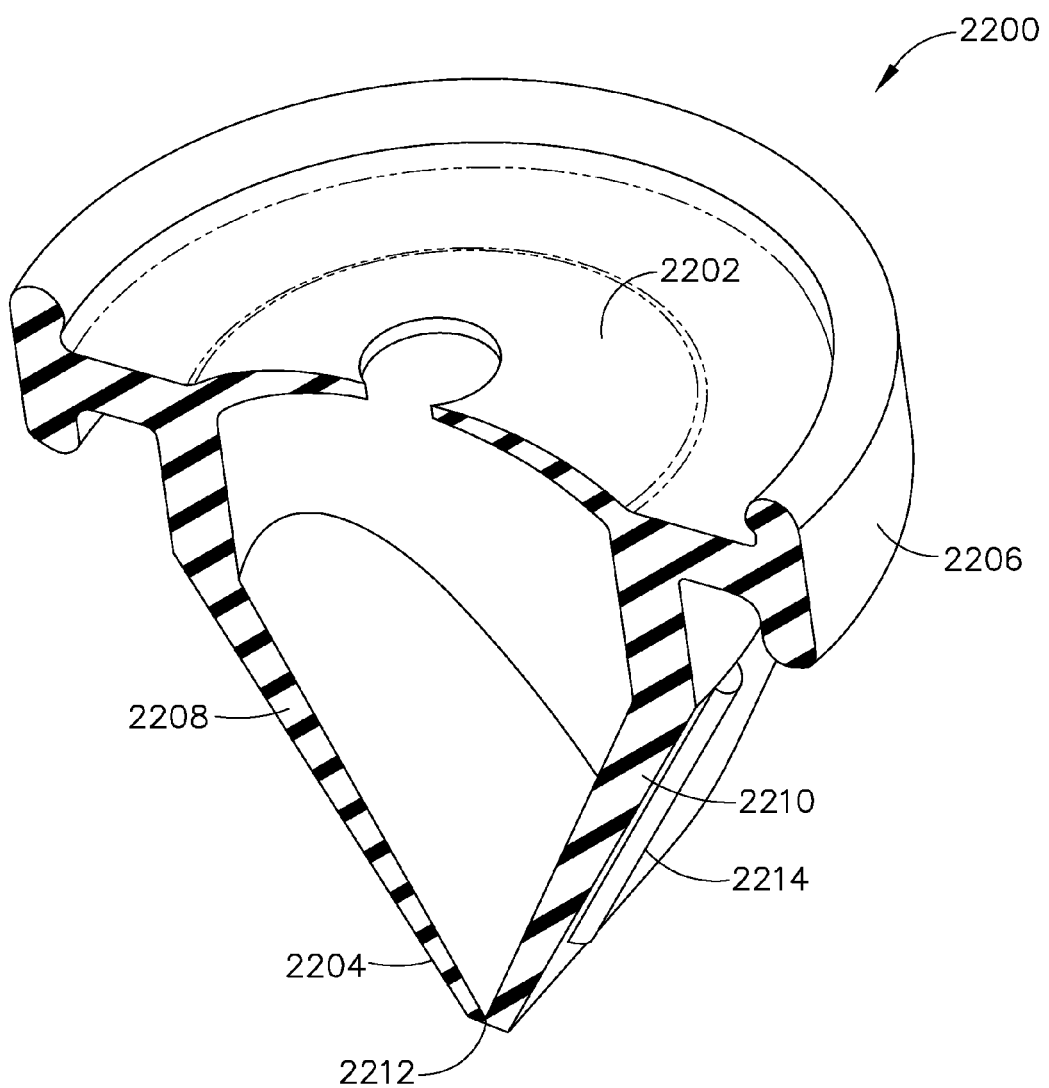
FIG. 63 is a front perspective view, in section, of a channel seal in accordance with one particular aspect of the disclosure.
Figure 64:
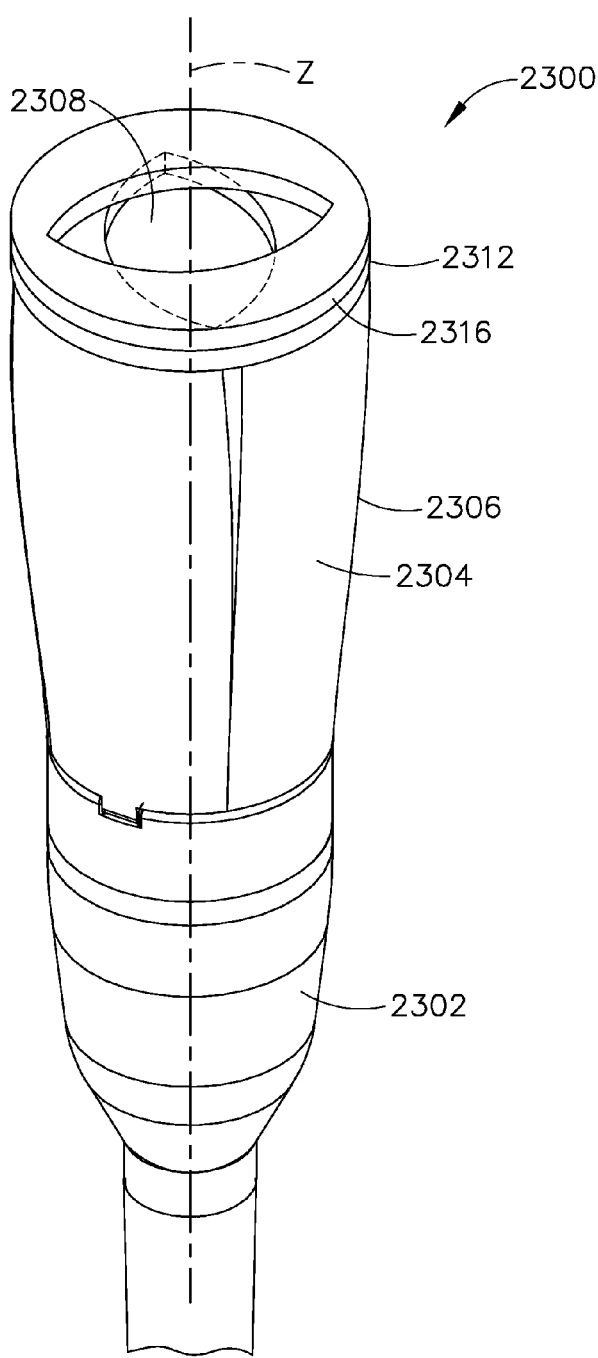
FIG. 64 is a front perspective view of a trocar assembly having a scope supporting mechanism in accordance with yet another aspect of the disclosure.
Figure 65:
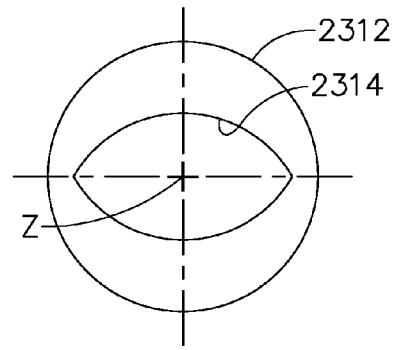
FIG. 65 is a top plan view of a first portion of the scope supporting mechanism of FIG. 64.
Figure 66:
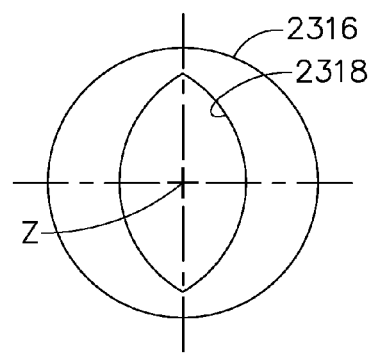
FIG. 66 is a top plan view of a second portion of the scope supporting mechanism of FIG. 64.
Figure 67:
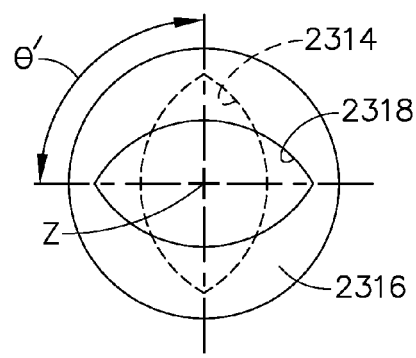
FIG. 67 is a top plan view of the trocar assembly of FIG. 64.

Referring back to FIG. 63, in another particular aspect, the channel seal 2200 may be a septum cum duckbill-type check valve that includes both a septum valve portion 2202 and a duckbill valve portion 2204. The channel seal 2200 may additionally include a flange 2206 for positioning the channel seal between a cap and a housing, as is discussed herein.

The duckbill valve portion 2204 may include a first duckbill portion 2208 and second duckbill portion 2210, wherein the first and second duckbill portions 2208, 2210 form a seal 2212. Each of the first and second duckbill portions 2208, 2210 may include a reinforcing rib 2214 that maintains the shape of the associated duckbill portion and, ultimately, maintains the integrity of the seal 2212.

Figure 29:
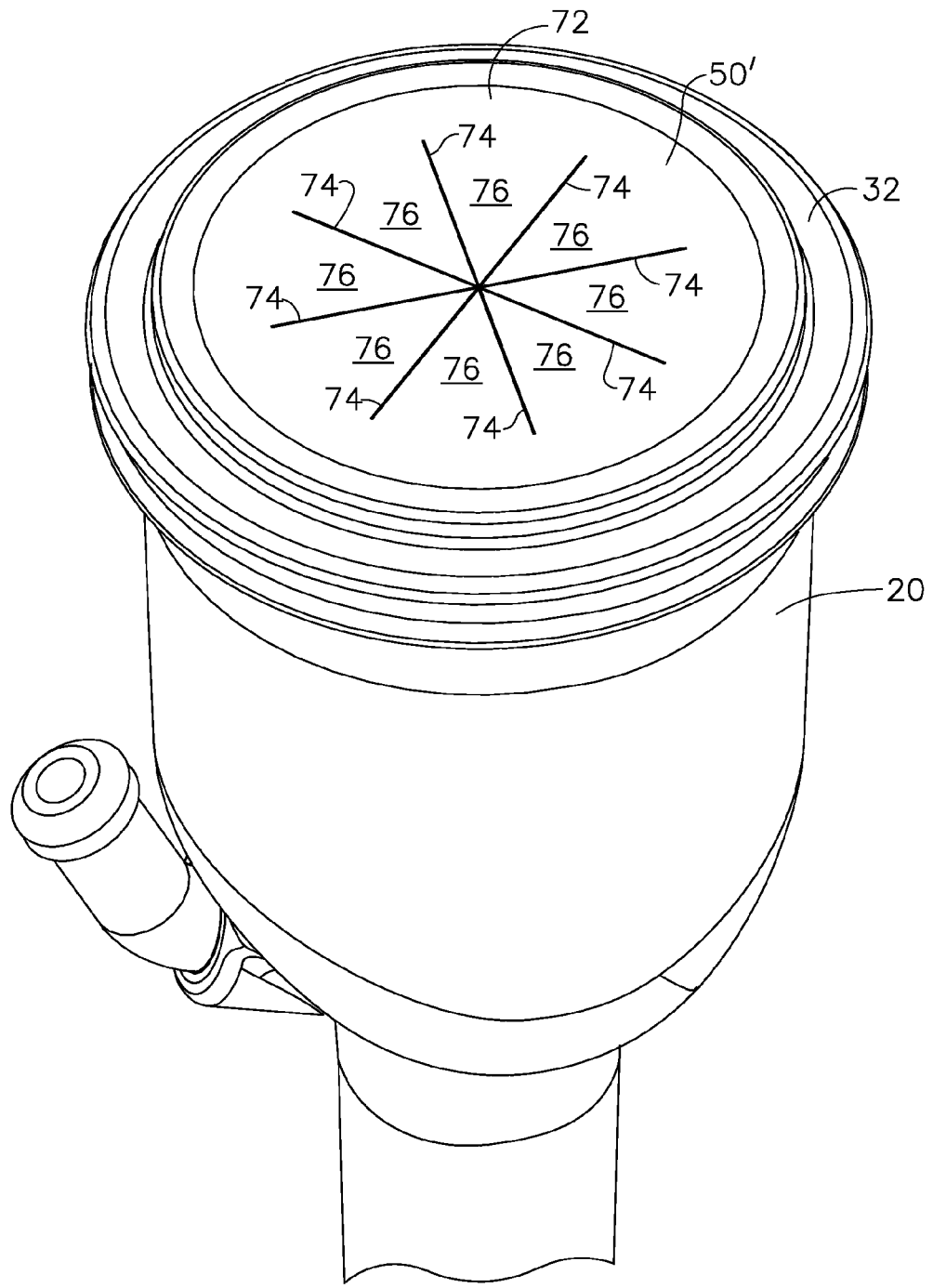
FIG. 29 is a top perspective view of the valve housing of the sleeve assembly of the trocar assembly, shown with the cap removed, in accordance with a second alternative aspect of the disclosure.

Alternatively, as shown in FIG. 29, the channel seal 50' may be a segmented valve having a deformable body 72 having a plurality of radially oriented slits 74 extending axially therethrough to define a plurality of pie-shaped segments 76. In the relaxed configuration (shown in FIG. 29), each pie-shaped segment 76 may be aligned with the adjacent segments 76 to enclose the open, proximal end 32 of the housing 20 and seal the working channel 36 (FIG. 2). However, when a medical instrument (not shown) is introduced, the instrument may pass through one or more of the slits 74 and into the working channel 36 by displacing a portion of one or more of the pie-shaped segments 76 axially inward (i.e., distally) and out of alignment with adjacent segments 76.

Figure 30:
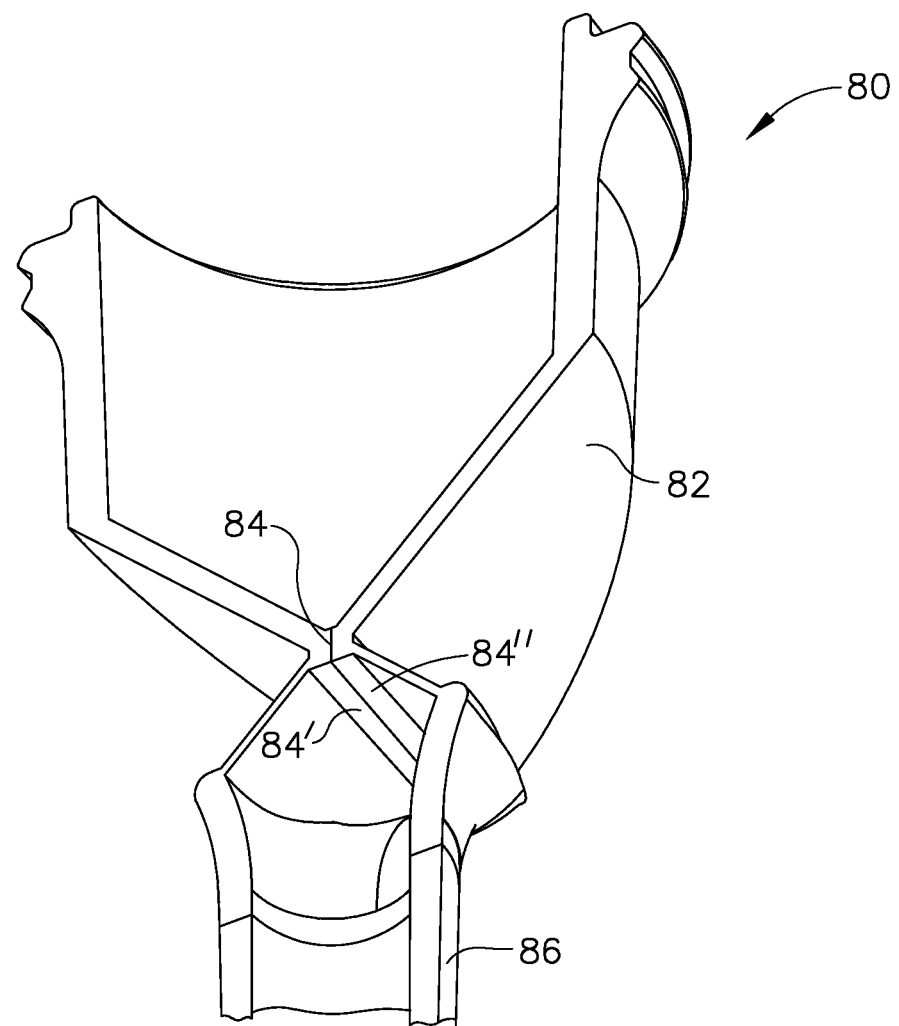
FIG. 30 is a front perspective view of a portion of a trocar sleeve assembly in accordance with another embodiment of the disclosed trocar assembly.

Referring to FIG. 30, in an alternative embodiment, the disclosed sleeve assembly, generally designated 80, may include a housing 82 having an integral, one-piece, seamless channel seal 84, such as a duckbill-type check valve. The housing 82 may be molded from a pliable polymeric material, such as polyisoprene, and may have sufficient rigidity such that the integral channel seal 84 is biased to a sealed configuration. In a first aspect of the alternative embodiment, the sleeve assembly 80 may include a separate cannula 86 connected to the housing 82. The cannula 86 may be formed from the same or different material than the housing 82, such as a more rigid material (e.g., polycarbonate). In a second aspect of the alternative embodiment (not shown), the sleeve assembly may include a cannula that is integral with housing, such that the housing, the channel seal and the cannula are formed as a single monolithic body.

In the relaxed configuration (shown in FIG. 30), the lips 84', 84" of the duckbill portion of the channel seal 84 may be aligned to close the channel seal 84 and seal the working channel 36 (FIG. 2). However, when a medical instrument (not shown) is introduced, the instrument may pass between the lips 84', 84" of the channel seal 84 and into the working channel 36. The lips 84', 84" may form a seal around the instrument.

Referring to FIG. 1B, the obturator assembly 14 may include an obturator 100 and a handle 102. The obturator 100 may include a tubular body 104 having an open proximal end 106 and an open distal end 108, with a penetrating tip 110 coupled to the open distal end 108 thereof. The tubular body 104 may be elongated along the longitudinal axis A and may define an elongated channel 112 extending between the open proximal end 106 and the open distal end 108.

Figure 32:
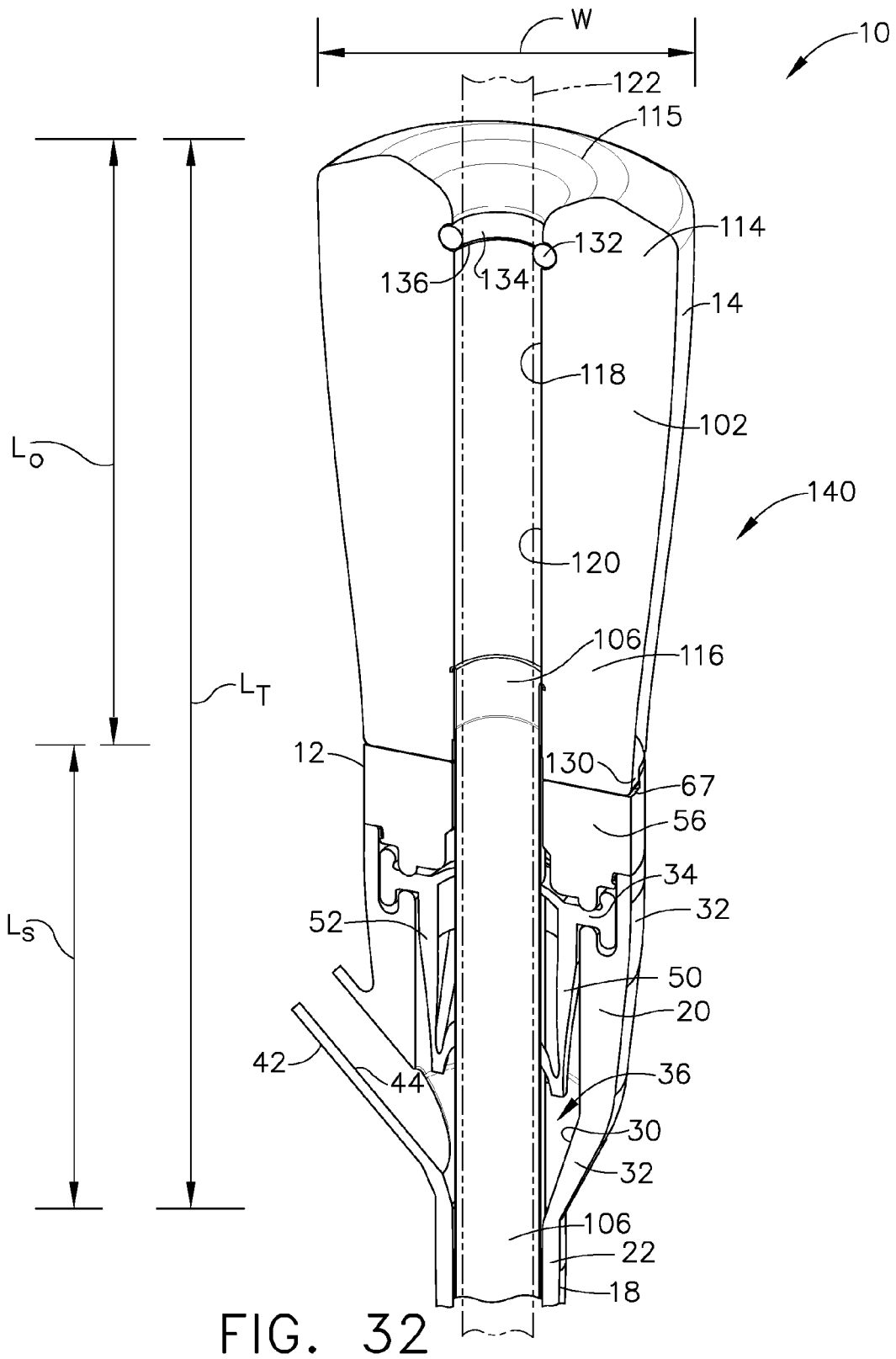
FIG. 32 is a front perspective view, in section, of a portion of a trocar assembly having a scope supporting mechanism in accordance with a second aspect of the disclosure.

Referring to FIGS. 1B and 32, the handle 102 may include an open proximal end 114 and an open distal end 116, and may define a channel 118 extending between the open proximal end 114 and the open distal end 116. The open proximal end 106 of the obturator 100 may be connected to the open distal end 116 of the handle 102 to couple the channel 118 of the handle 102 with the channel 112 of the obturator 100, thereby defining an elongated working channel 120 through the obturator assembly 14. The working channel 120 of the obturator assembly 14 may be sized to receive a scoping device 122 (FIG. 32) therein.

The proximal end 114 of the handle 102 may define a beveled guide surface 115 configured to direct medical instruments (e.g., scoping device 122 in FIG. 32) to the channel 118 in the handle 102 and, ultimately, to the working channel 120 of the obturator assembly 14.

In one particular aspect, the penetrating tip 110 of the obturator 100 may be an optical penetrating tip to allow a scoping device 122 (FIG. 32) to view through the penetrating tip 110 during a surgical procedure. For example, the penetrating tip 110 may be formed from a rigid, yet translucent polymeric material, such as optically clear polycarbonate.

Referring to FIG. 1C, the penetrating tip 110 may terminate at a distal point 124 (e.g., a sharp pointed tip) and may include two blades 126, 128 extending radially outward therefrom. The blades 126, 128 may be disposed about 180 degrees relative to each other and may define a cutting plane. In one aspect, when the obturator assembly 14 is inserted through the working channel 36 of the sleeve assembly 12, the obturator assembly 14 may be aligned relative to the sleeve assembly 12 such that the blades 126, 128 are at an angle $\theta_2$ relative to the tip 27 of the bevel 26 of the sleeve assembly 12 in end view. In one particular aspect, the obturator assembly 14 may be aligned relative to the sleeve assembly 12 such that the cutting plane defined by the blades 126, 128 is offset by at least about 60 degrees (e.g., about 90 degrees) relative to the tip 27 of the bevel 26 of the sleeve assembly 12.

Referring to FIGS. 1A, 1B and 32, the distal end 116 of the handle 102 may include a protrusion 130, such as a tongue, that extends axially forward (i.e., distally) therefrom and radially outward from the channel 118. The protrusion 130 may be sized and shaped to be received within the groove 67 formed in the cap 56 of the sleeve assembly 12 to align the obturator assembly 14 relative to the sleeve assembly 12. For example, as discussed above, the protrusion 130 of the obturator assembly 14 and the groove 67 in the sleeve assembly 12 may facilitate precise alignment of the blades 126, 128 of the penetrating tip 110 of the obturator assembly 14 relative to the tip 27 of the bevel 26 of the sleeve assembly 12, as shown in FIG. 1C and discussed above.

Furthermore, the protrusion 130 and the groove 67 may be sized to achieve an interference fit such that the obturator assembly 14 may be secured to the sleeve assembly 12 when the protrusion 130 is urged into the groove 67. Those skilled in the art will appreciate that the extent of the interference fit between the protrusion 130 and the groove 67 may determine the amount of force that will be required to disconnect the obturator assembly 14 from the sleeve assembly 12 when the protrusion 130 is received in the groove 67.

Those skilled in the art will appreciate that various alternative techniques and mechanisms may be used to connect the obturator assembly 14 to the sleeve assembly 12, while maintaining desired circumferential alignment of the obturator assembly 14 relative to the sleeve assembly 12, some of which are described below.

Figure 42:
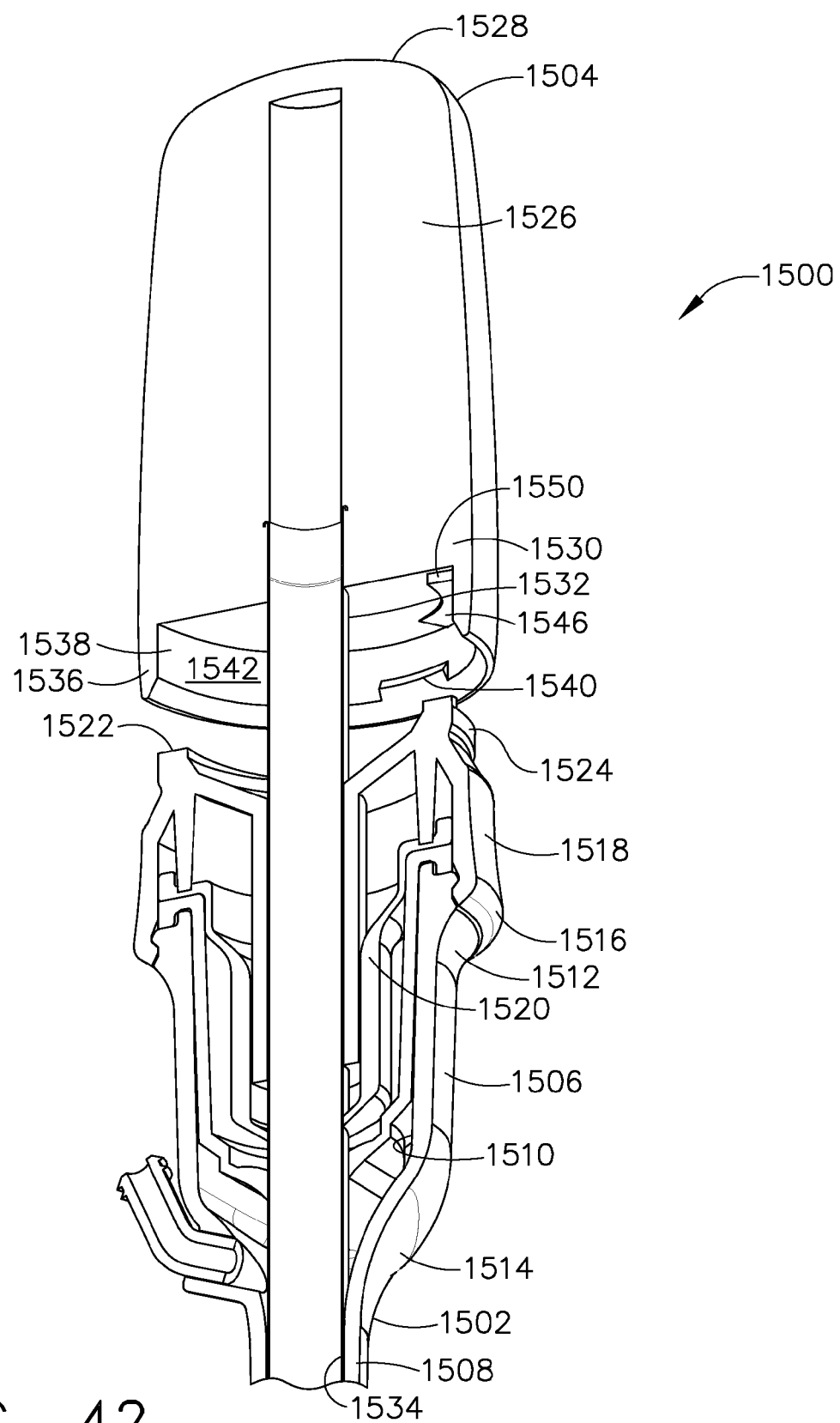
FIG. 42 is a partially exploded, perspective view, in section, of a portion of yet another embodiment of the disclosed trocar assembly, wherein the trocar assembly includes an obturator-to-sleeve locking mechanism in accordance with a first alternative aspect of the disclosure.
Figure 43:
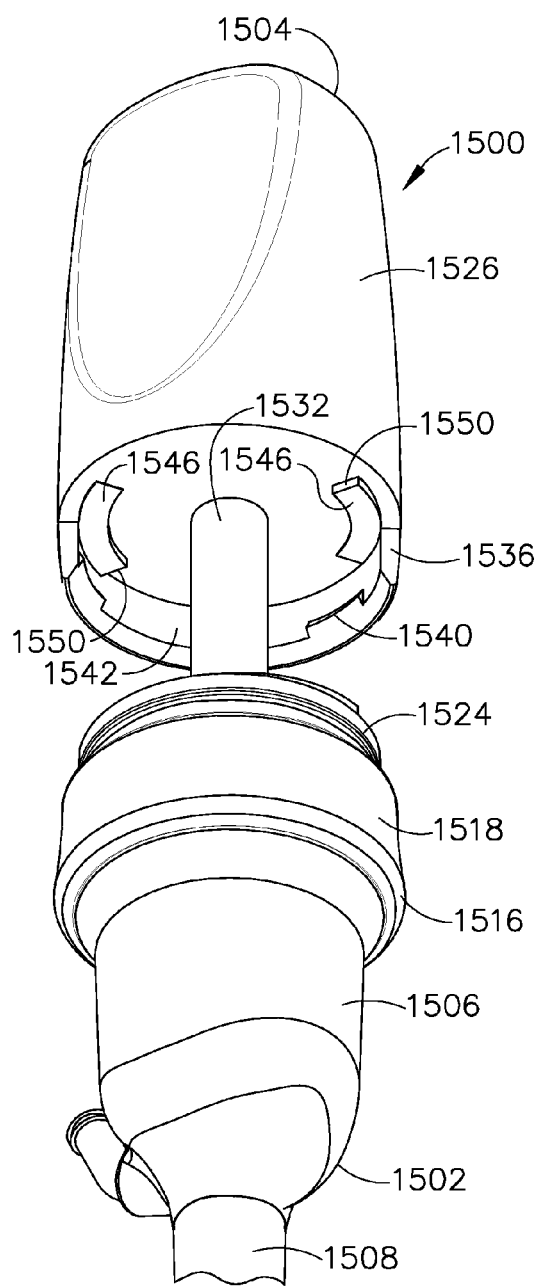
FIG. 43 is an upward looking perspective view of the trocar assembly of FIG. 42.
Figure 44:
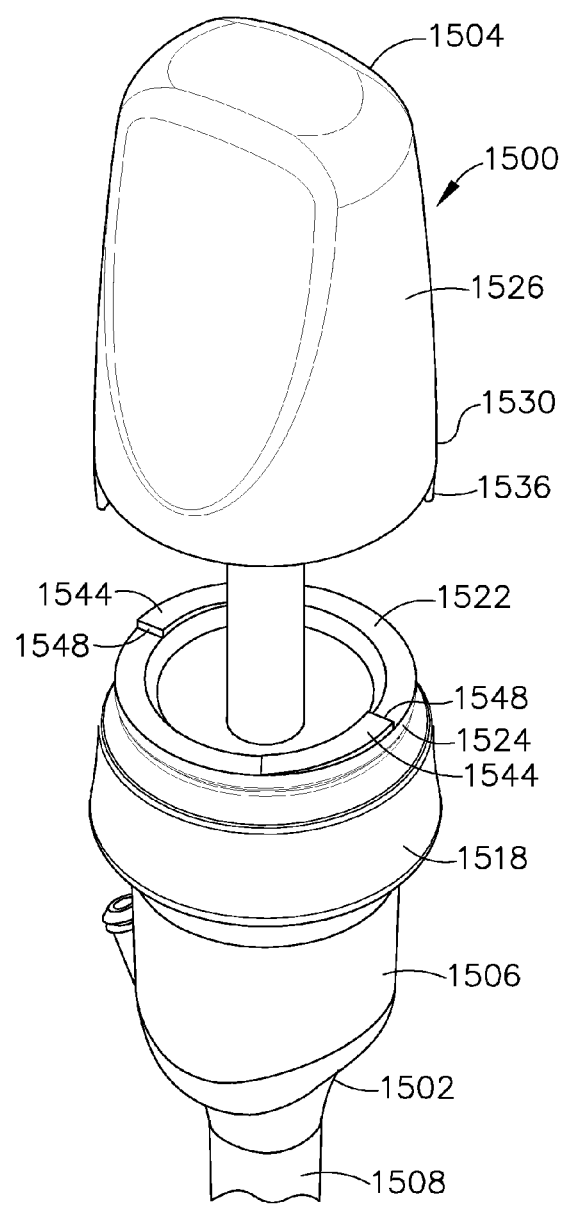
FIG. 44 is a downward looking perspective view of the trocar assembly of FIG. 42.

Referring to FIGS. 42-44, in a first alternative aspect, a trocar assembly, generally designated 1500, may include a sleeve assembly 1502 and an obturator assembly 1504. The obturator assembly 1504 may be axially connectable to the sleeve assembly 1502, while maintaining desired circumferential alignment of the obturator assembly 1504 relative to the sleeve assembly 1502.

The sleeve assembly 1502 may include a housing 1506 and a cannula 1508 fluidly coupled to the housing 1506. The housing 1506 may define an internal volume 1510 and may include a proximal end 1512 and a distal end 1514. A distal end 1516 of a cap 1518 may be connected to the proximal end 1512 of the housing 1506 to enclose a channel seal 1520 within the internal volume 1510 of the housing 1506. The proximal end 1522 of the cap 1518 may include a radially outward extending protrusion 1524.

The obturator assembly 1504 may include a handle 1526 having a proximal end 1528 and a distal end 1530, and an obturator 1532 connected to the handle 1526. The obturator 1532 may extend through a working channel 1534 of the sleeve assembly 1502. The distal end 1530 of the handle 1526 may include an annular extension 1536 that defines a recess 1538 that is sized and shaped to receive the proximal end 1522 of the cap 1518 therein. The annular extension 1536 may include a plurality of radially inward extending protrusions 1540 spaced circumferentially about the inner surface 1542 of the annular extension 1536.

Accordingly, the obturator assembly 1504 may be connected to the sleeve assembly 1502 by positioning the annular extension 1536 of the distal end 1530 of the handle 1526 over the proximal end 1522 of the cap 1518 such that the radially inward extending protrusions 1540 snap over the protrusion 1524 of the cap 1518, thereby resisting axial separation of the obturator assembly 1504 from the sleeve assembly 1502.

Additionally, the proximal end 1522 of the cap 1518 may include partially circumferential, distally-tapering ramps 1544. The distal end 1530 of the handle 1526 may include partially circumferential, proximally-tapering ramps 1546. When the obturator assembly 1504 is inserted into, and locked onto, the sleeve assembly 1502, as described above, the obturator assembly 1504 may be circumferentially rotated relative to the sleeve assembly 1502 until the ends 1548 of the ramps 1544 on the sleeve assembly 1502 abut the ends 1550 of the ramps 1546 on the obturator assembly 1504, thereby preventing further rotation and circumferentially aligning the obturator assembly 1504 relative to the sleeve assembly 1502.

Figure 45:
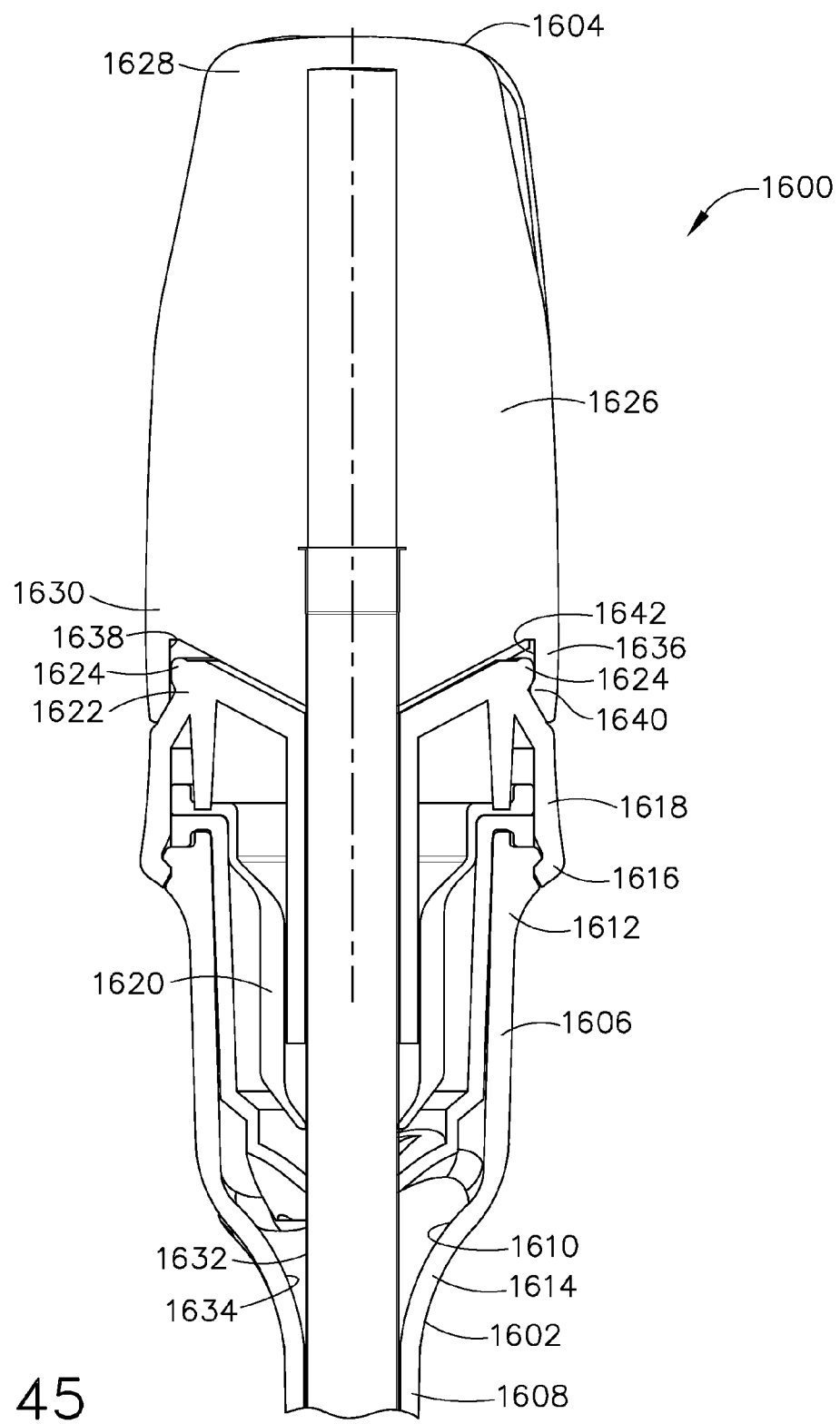
FIG. 45 is a front perspective view of a portion of a trocar assembly having an obturator-to-sleeve locking mechanism in accordance with a second alternative aspect of the disclosure.
Figure 46:
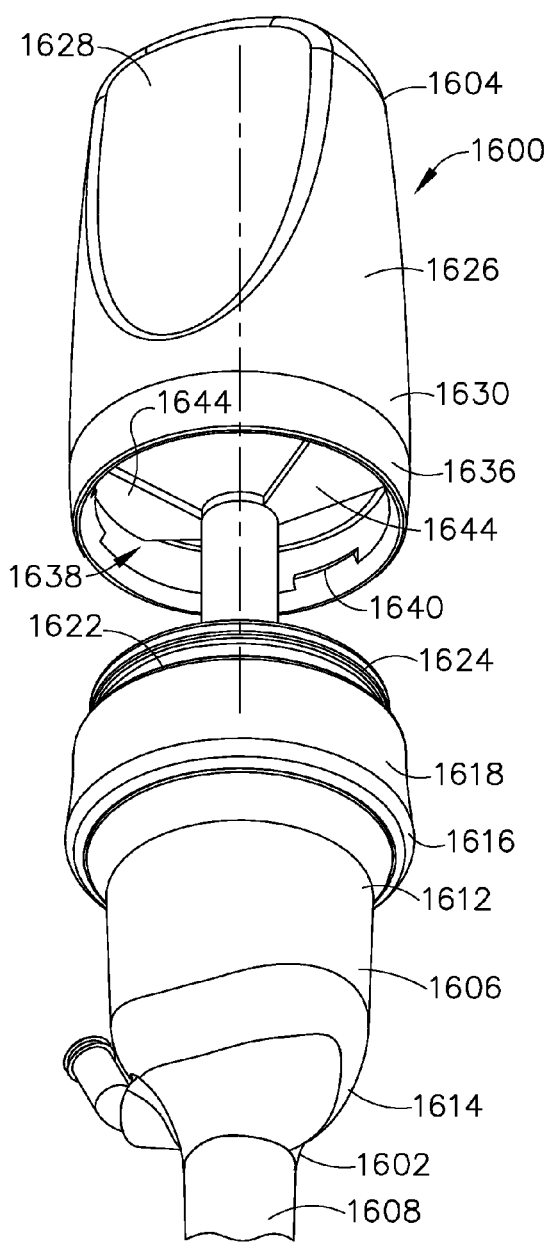
FIG. 46 is an upward looking, partially exploded, perspective view of the trocar assembly of FIG. 45.
Figure 47:
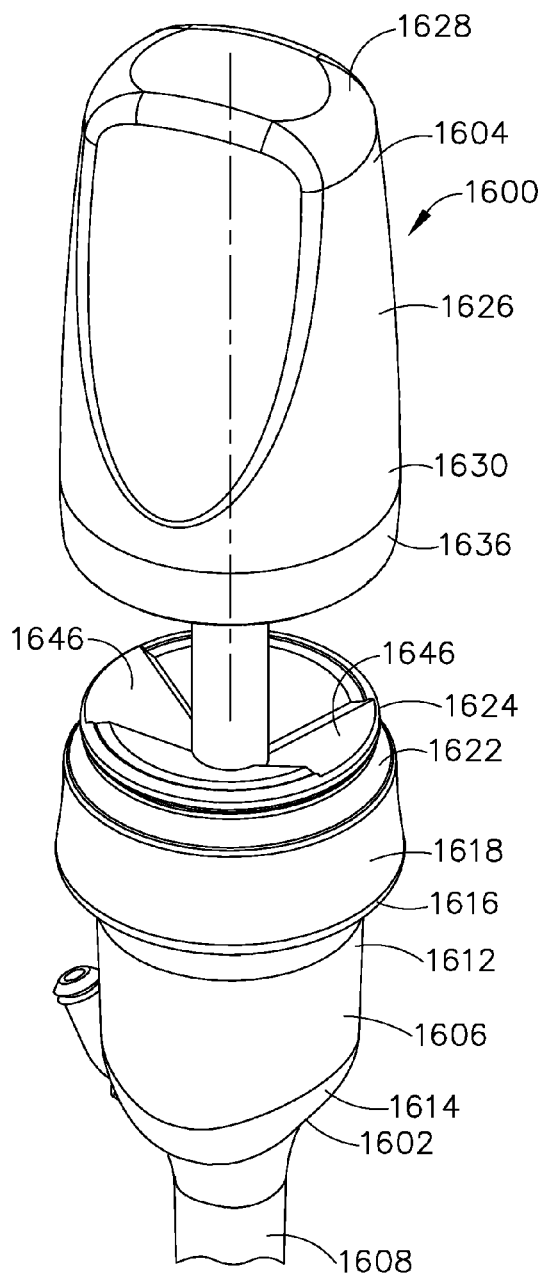
FIG. 47 is a downward looking, partially exploded, perspective view of the trocar assembly of FIG. 45.

Referring to FIGS. 45-47, in a second alternative aspect, a trocar assembly, generally designated 1600, may include a sleeve assembly 1602 and an obturator assembly 1604. The obturator assembly 1604 may be axially connectable to the sleeve assembly 1602, while maintaining desired circumferential alignment of the obturator assembly 1604 relative to the sleeve assembly 1602.

The sleeve assembly 1602 may include a housing 1606 and a cannula 1608 fluidly coupled to the housing 1606. The housing 1606 may define an internal volume 1610 and may include a proximal end 1612 and a distal end 1614. A distal end 1616 of a cap 1618 may be connected to the proximal end 1612 of the housing 1606 to enclose a channel seal 1620 within the internal volume 1610 of the housing 1606. The proximal end 1622 of the cap 1618 may include a radially outward extending protrusion 1624.

The obturator assembly 1604 may include a handle 1626 having a proximal end 1628 and a distal end 1630, and an obturator 1632 connected to the handle 1626. The obturator 1632 may extend through a working channel 1634 of the sleeve assembly 1602. The distal end 1630 of the handle 1626 may include an annular extension 1636 that defines a recess 1638 that is sized and shaped to receive the proximal end 1622 of the cap 1618 therein. The annular extension 1636 may include a plurality of radially inward extending protrusions 1640 spaced circumferentially about the inner surface 1642 of the annular extension 1636.

Accordingly, the obturator assembly 1604 may be connected to the sleeve assembly 1602 by positioning the annular extension 1636 over the proximal end 1622 of the cap 1618 such that the radially inward extending protrusions 1640 snap over the protrusion 1624 of the cap 1618, thereby resisting axial separation of the obturator assembly 1604 from the sleeve assembly 1602. The protrusions 1640 and the protrusion 1624 may be sized such that a sufficient manual pulling force can separate the obturator assembly 1604 from the sleeve assembly 1602.

Additionally, the distal end 1630 of the handle 1626 may include raised, distally tapering surfaces 1644. The surfaces 1644 may be pie-shaped radial segments. The proximal end 1622 of the cap 1618 may include distally tapering recesses 1646 that are sized and shaped to closely receive the surfaces 1644 of the handle 1626. The obturator assembly 1604 may be inserted into, and locked onto, the sleeve assembly 1602, as described above, and the surfaces 1644 may be received in the recess 1646, thereby circumferentially aligning the obturator assembly 1604 relative to the sleeve assembly 1602 in the desired configuration.

Figure 48:
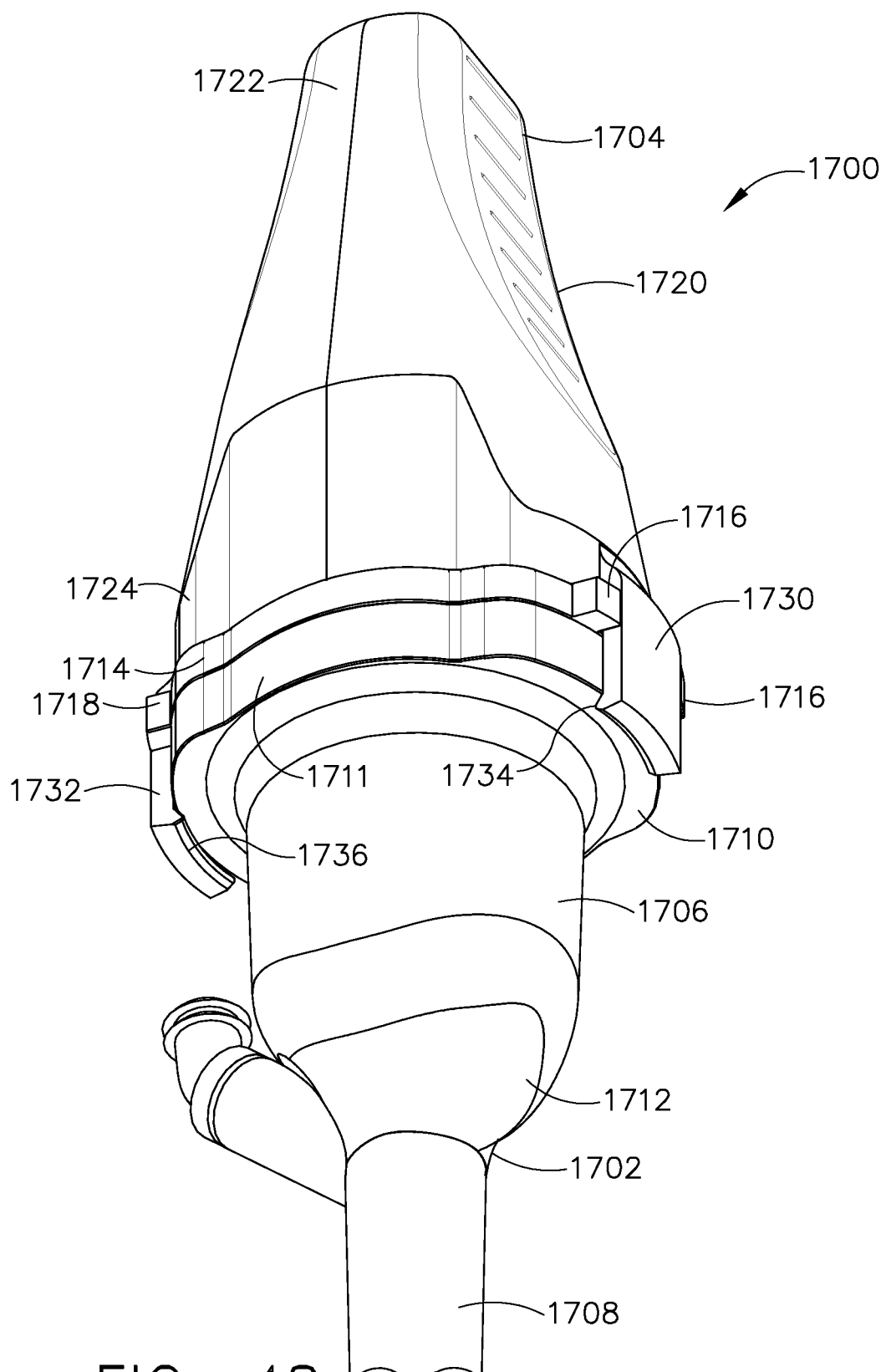
FIG. 48 is a front elevational view, in section, of a portion of a trocar assembly having an obturator-to-sleeve locking mechanism in accordance with a third alternative aspect of the disclosure.

Referring to FIGS. 48-50, in a third alternative aspect, a trocar assembly, generally designated 1700, may include a sleeve assembly 1702 and an obturator assembly 1704. The obturator assembly 1704 may be axially connectable to the sleeve assembly 1702, while maintaining desired circumferential alignment of the obturator assembly 1704 relative to the sleeve assembly 1702.

The sleeve assembly 1702 may include a housing 1706 and a cannula 1708 fluidly coupled to a distal end 1712 of the housing 1706. A proximal end 1710 of the housing 1706 may include a flanged portion 1711 that extends radially outward from the housing 1706, and may include a cap 1714 connected thereto. The cap 1714 may include a first set of guide protrusions 1716 and a second set of guide protrusions 1718.

The obturator assembly 1704 may include a handle 1720 having a proximal end 1722 and a distal end 1724, and an obturator 1726 connected to the handle 1720. The obturator 1726 may extend through an opening 1728 to the working channel of the sleeve assembly 1702. The distal end 1724 of the handle 1720 may include tabs 1730, 1732 extending axially therefrom. The first tab 1730 may be size to fit between the first set of guide protrusions 1716 and the second tab 1732 may be size to fit between the second set of guide protrusions 1718, thereby circumferentially aligning the obturator assembly 1704 relative to the sleeve assembly 1702.

Each tab 1730, 1732 may include a radially inward extending protrusion 1734 extending from an inner surface 1736 thereof. The inward extending protrusions 1734 may snap over the flanged portion 1711 of the proximal end 1710 of the housing 1706, thereby resisting axial separation of the obturator assembly 1704 from the sleeve assembly 1702.

Figure 51:
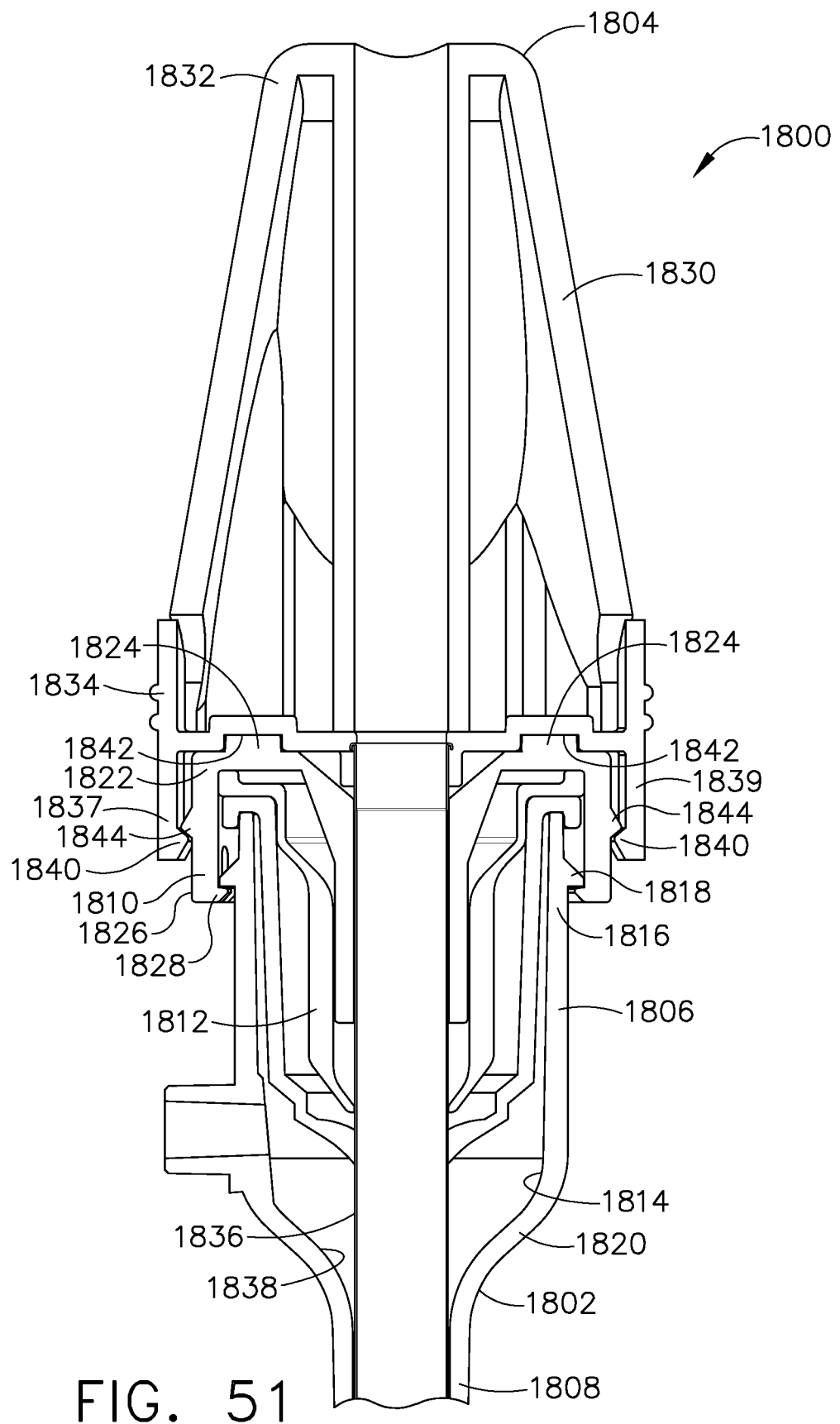
FIG. 51 is a front elevational view, in section, of a portion of a trocar assembly having an obturator-to-sleeve locking mechanism in accordance with a fourth alternative aspect of the disclosure.
Figure 52:
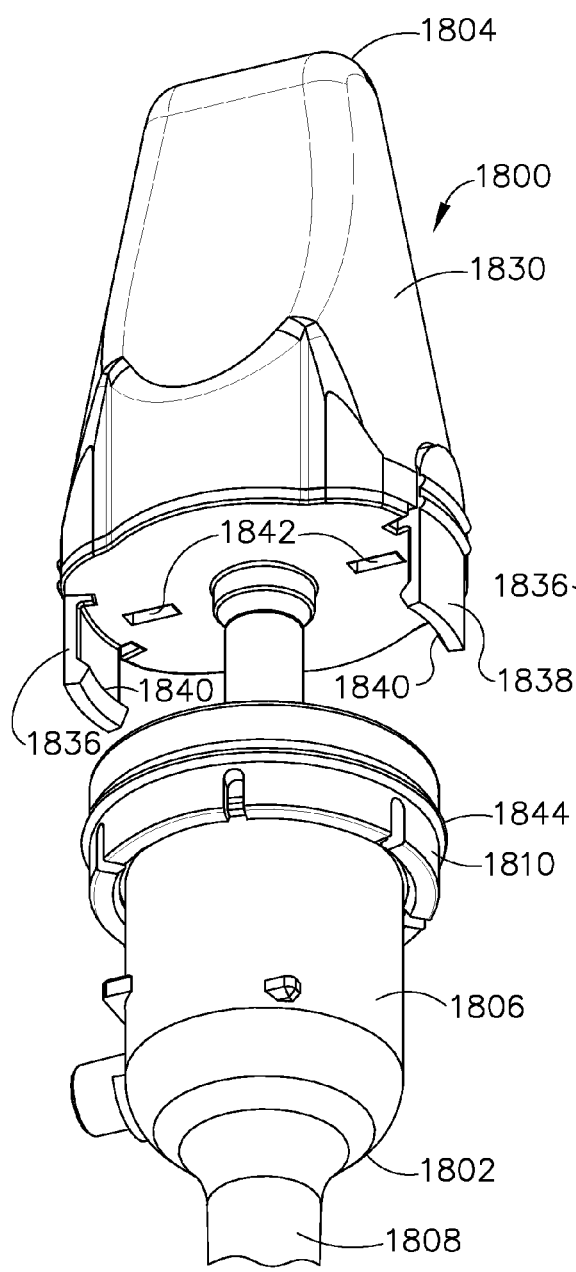
FIG. 52 is an upward looking, partially exploded, perspective view of the trocar assembly of FIG. 51.
Figure 53:
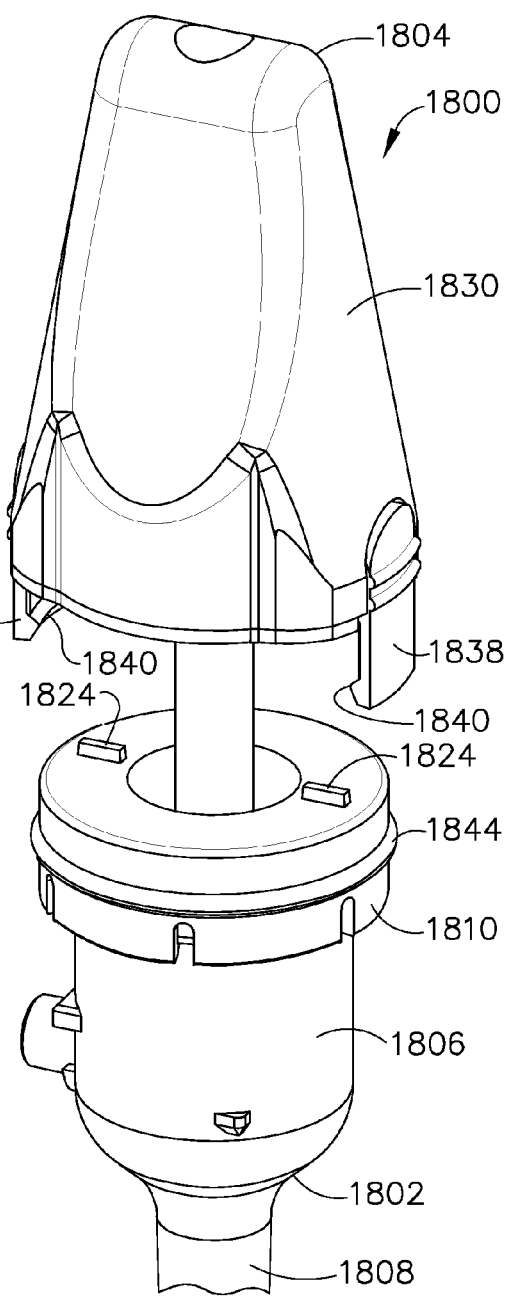
FIG. 53 is a downward looking, partially exploded, perspective view of the trocar assembly of FIG. 51.

Referring to FIGS. 51-53, in a fourth alternative aspect, a trocar assembly, generally designated 1800, may include a sleeve assembly 1802 and an obturator assembly 1804. The obturator assembly 1804 may be axially connectable to the sleeve assembly 1802, while maintaining desired circumferential alignment of the obturator assembly 1804 relative to the sleeve assembly 1802.

The sleeve assembly 1802 may include a housing 1806, a cannula 1808, a cap 1810 and a channel seal 1812. The housing 1806 may define an internal volume 1814 and may include a proximal end 1816 having a circumferential, proximally tapering protrusion 1818 and a distal end 1820 connected to the cannula 1808. The cap 1810 may include a proximal end 1822 having axial protrusions or detents 1824 extending upward in the proximal direction, a distal end 1826 having a partially circumferential, radially inward extending protrusion 1828, and a circumferential, distally and proximally tapering protrusion 1844 extending radially outward between the proximal and distal ends 1822, 1826.

The cap 1810 may be connected to the housing 1806 by coaxially positioning the cap 1810 over the housing 1806 such that the inward extending protrusion 1828 snaps over the proximally tapering protrusion 1818 of the housing 1806, thereby securing the channel seal 1812 within the internal volume 1814.

The obturator assembly 1804 may include a handle 1830 having a proximal end 1832 and a distal end 1834, and an obturator 1836 connected to the handle 1830. The obturator 1836 may extend through the working channel 1838 of the sleeve assembly 1802. The distal end 1834 of the handle 1830 may include tabs 1837, 1839 extending axially therefrom, wherein each tab 1837, 1839 may include a radially inward extending protrusion 1840. Recesses 1842 may be formed in the distal end 1834 of the handle 1830 and may be sized and shaped to closely receive the detents 1824 therein.

The obturator assembly 1804 may be axially coupled to the sleeve assembly 1802 by advancing the radially inward extending protrusions 1840 of the tabs 1836, 1838 distally beyond the protrusion 1844 of the cap 1810 such that the protrusions 1840 of the tab 1836, 1838 snap onto the protrusion 1844 of the cap 1810. Precise circumferential alignment of the obturator assembly 1804 relative to the sleeve assembly 1802 may be achieved when the detents 1824 extending from the cap 1810 are received in the recesses 1842 in the handle 1830. The protrusions 1840 on the obturator assembly 1804 and the protrusion 1844 on the sleeve assembly 1802 may be sized such that a sufficient manual pulling force can separate the obturator assembly 1804 from the sleeve assembly 1802.

Figures 54, 55:
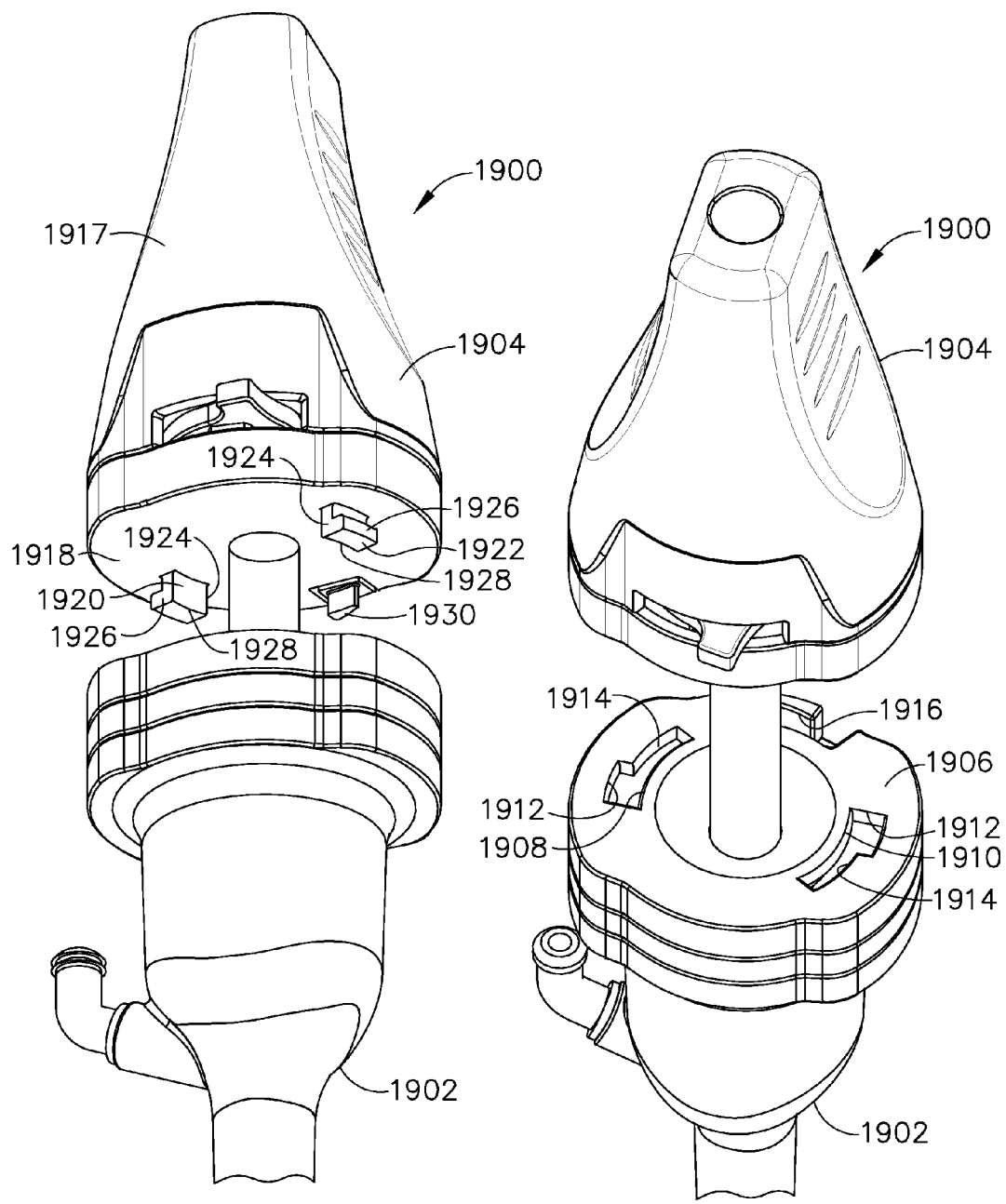
FIG. 54 is an upward looking, partially exploded, perspective view of a portion of a trocar assembly having an obturator-to-sleeve locking mechanism in accordance with a fifth alternative aspect of the disclosure.
FIG. 55 is a downward looking, partially exploded, perspective view of the trocar assembly of FIG. 54.

Referring to FIGS. 54 and 55, in a fifth alternative aspect, a trocar assembly, generally designated 1900, may include a sleeve assembly 1902 and an obturator assembly 1904. The obturator assembly 1904 may be axially connectable to the sleeve assembly 1902, while maintaining desired circumferential alignment of the obturator assembly 1904 relative to the sleeve assembly 1902.

As shown in FIG. 55, the sleeve assembly 1902 may include a proximal end 1906 that defines a first locking groove 1908 and a second, circumferentially opposed locking groove 1910. Each locking groove 1908, 1910 may include an opening 1912 and a narrower, undercut, partially circumferential groove 1914 adjacent to and extending away from the associated opening 1912. Additionally, the proximal end 1906 of the sleeve assembly 1902 may define a third, open, partially circumferential groove 1916 with similar characteristics as locking grooves 1908, 1910.

As shown in FIG. 54, the obturator assembly 1904 may include a handle 1917 having a distal end 1918. First and second circumferentially opposed L-shaped projections 1920, 1922 may extend from the distal end 1918 of the handle 1917. Each L-shaped projection 1920, 1922 may include an axial portion 1924 extending distally from the distal end 1918 of the handle 1917 and a radial portion 1926 that extends radially outward from the distal end 1928 of the axial portion 1924. Additionally, a third, generally flat, tapered projection 1930 may extend from the distal end 1918 of the handle 1917.

The obturator assembly 1904 may be axially coupled to, and circumferentially aligned with, the sleeve assembly 1902 by positioning the L-shaped projections 1920, 1922 into the openings 1912 of the corresponding locking grooves 1908, 1910 and the third projection 1930 into the corresponding third groove 1916. Then, the obturator assembly 1904 may be circumferentially rotated relative to the sleeve assembly 1902 such that the axial portion 1924 of each L-shaped projection 1920, 1922 extends into the undercut, partially circumferential groove 1914 of the corresponding locking groove 1908, 1910, thereby positioning a portion of the proximal end 1906 of the sleeve assembly 1902 between the radial portions 1926 of the L-shaped projections 1920, 1922 and the distal end 1918 of the handle 1917 of the obturator assembly 1904.

Figure 56:
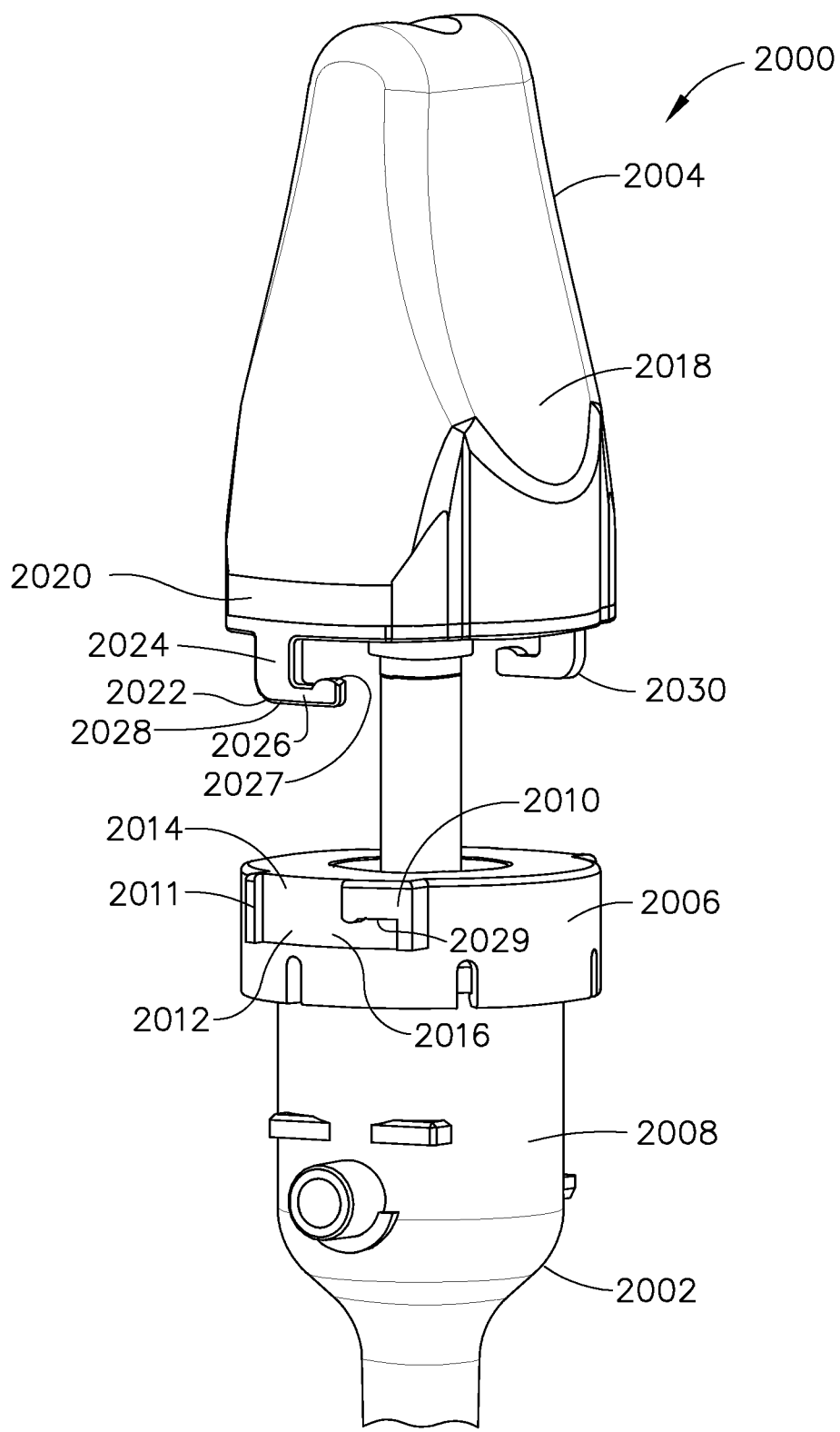
FIG. 56 is a partially exploded, front perspective view of a portion of a trocar assembly having an obturator-to-sleeve locking mechanism in accordance with a sixth alternative aspect of the disclosure.

Referring to FIG. 56, in a sixth alternative aspect, a trocar assembly, generally designated 2000, may include a sleeve assembly 2002 and an obturator assembly 2004. The obturator assembly 2004 may be axially connectable to the sleeve assembly 2002, while maintaining desired circumferential alignment of the obturator assembly 2004 relative to the sleeve assembly 2002.

The sleeve assembly 2002 may include a cap 2006 connected to a housing 2008 to enclose a channel seal (not shown) therein. The cap 2006 may include a radially-outward extending, partially circumferential projection 2010 and an end tab 2011 that together define a recess 2012 having an axial portion 2014 and a circumferential portion 2016

The obturator assembly 2004 may include a handle 2018 having a distal end 2020. A hook 2022 may be connected to the distal end 2020 of the handle 2018 and may include an axial portion 2024 and a circumferential portion 2026 that extends from distal end 2028 of the axial portion 2024. The circumferential portion 2026 of the hook 2022 may include a nub 2027 sized and shaped to engage a corresponding recess 2029 in the projection 2010 of the cap 2006.

The obturator assembly 2004 may be connected to the sleeve assembly 2002 by extending the hook 2022 through the axial portion 2014 of the recess 2012 defined in the projection 2010 of the sleeve assembly 2002, and then circumferentially rotating the obturator assembly 2004 relative to the sleeve assembly 2002 such that the circumferential portion 2026 of the hook 2022 extends into the circumferential portion 2016 of the recess 2012, thereby positioning a portion of the projection 2010 between the hook 2022 and the distal end 2020 of the handle 2018 to lock the handle 2018 of the obturator assembly 2004 to the sleeve assembly 2002.

A second hook 2030 (or more) may similarly engage the sleeve assembly 2002 on an opposite side from the first hook 2022.

Referring to FIG. 32, the handle 102 may include a support mechanism 132 for supporting the scoping device 122 within the working channel 120 of the obturator assembly 14. The support mechanism 132 may be configured to resist axial, radial and/or circumferential movement of the scoping device 122 relative to the working channel 120 of the obturator assembly 14, thereby allowing a practitioner to place a scoping device 122 into the working channel 120 as desired, while the support mechanism 132 maintains the desired position of the scoping device 122 without the need for constant manual manipulation of the scoping device 122.

In one particular aspect, the support mechanism 132 may include an O-ring 134 received in an annular groove 136 defined in the channel 118 of the handle 102. The O-ring 134 may be formed from a resilient material (e.g., rubber) and may have an inner diameter that is less than the outer diameter of the scoping device 122 (e.g., about 5 to about 15 percent smaller in one embodiment) such that the O-ring forms a seal around the scoping device 122 when the scoping device is inserted into the channel 118 defined by the handle 102, thereby securing the scoping device 122 relative to the handle 102.

Those skilled in the art will appreciate that various alternative support mechanisms may be used to support a medical instrument within the working channel 120 of the obturator assembly 14 to resist axial, radial and/or circumferential movement of the medical device relative to the obturator assembly 14, as will be described below.

Figure 31:
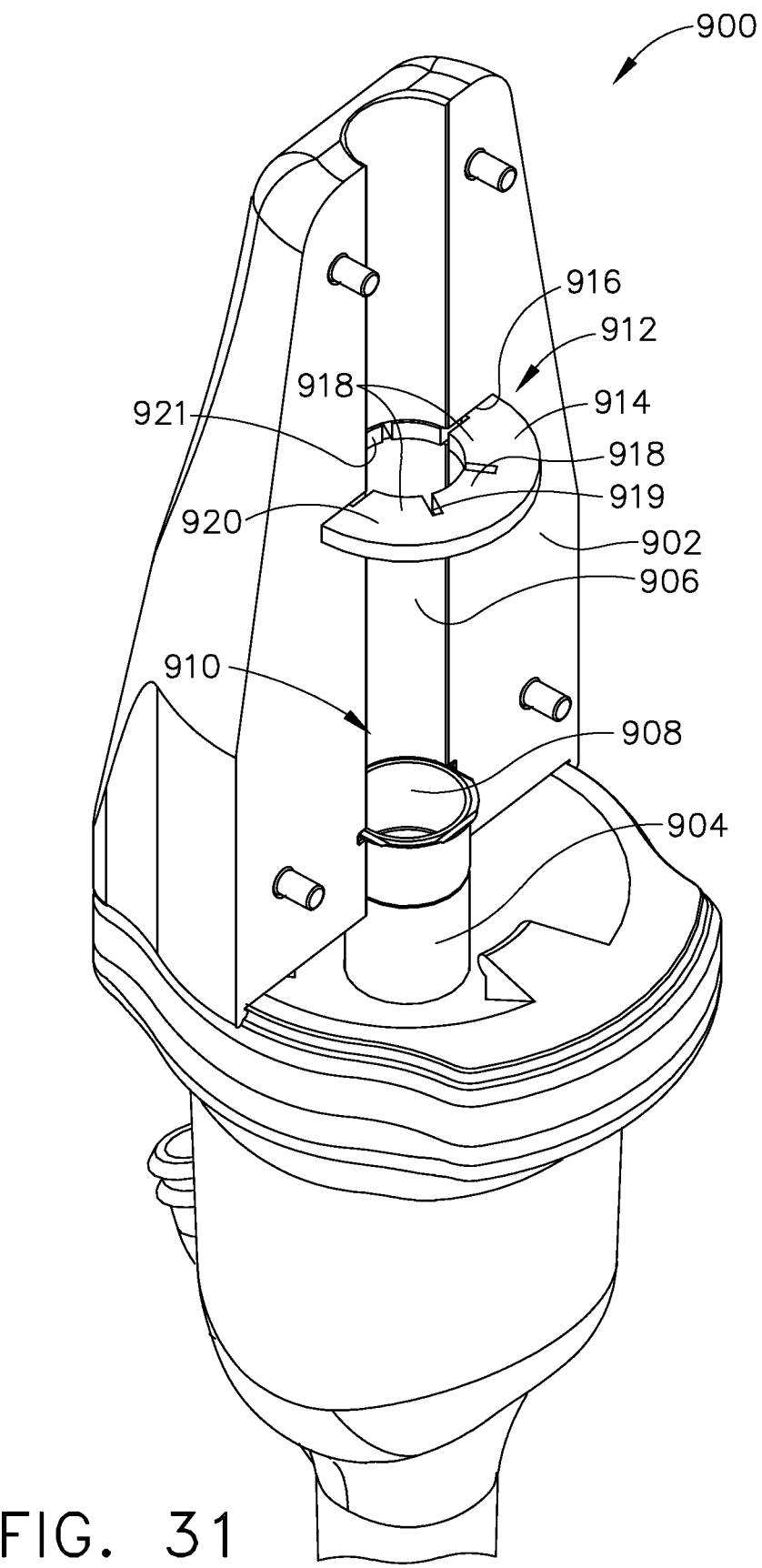
FIG. 31 is a front perspective view, partially in section, of a portion of another embodiment of the disclosed trocar assembly, wherein the trocar assembly includes a scope supporting mechanism in accordance with a first aspect of the disclosure.

Referring to FIG. 31, in a first alternative aspect, an obturator assembly, generally designated 900, may include a handle 902 connected to an obturator 904, wherein the handle 902 includes a channel 906 extending therethrough and coupled to a channel 908 extending through the obturator 904 to define a working channel 910 of the obturator assembly 900. A support mechanism 912 may be received in the channel 906 of the handle 902 to engage a medical instrument (not shown) inserting into the working channel 910.

The support mechanism 912 may include a resilient (e.g., rubber) grommet 914 received in an annular groove 916 in the handle 902. The grommet 914 may include a plurality of segments 918 extending radially inward into the channel 906 from a body portion 920 of the grommet 914. In an exemplary aspect, the segments 918 may be separated by gaps 919 and may define a central opening 921.

In the relaxed configuration, shown in FIG. 31, the segments 918 may extend radially inward toward the central opening 921. However, when a medical instrument, such as a scoping device, is inserted through the channel 906, the medical instrument may pass through the central opening and may deflect the segments 918 in the distal direction such that the resiliency of the grommet 914 urges the segments 918 in the proximal direction and into engagement with the medical instrument, thereby supporting the medical instrument in the channel 906.

Figure 33:
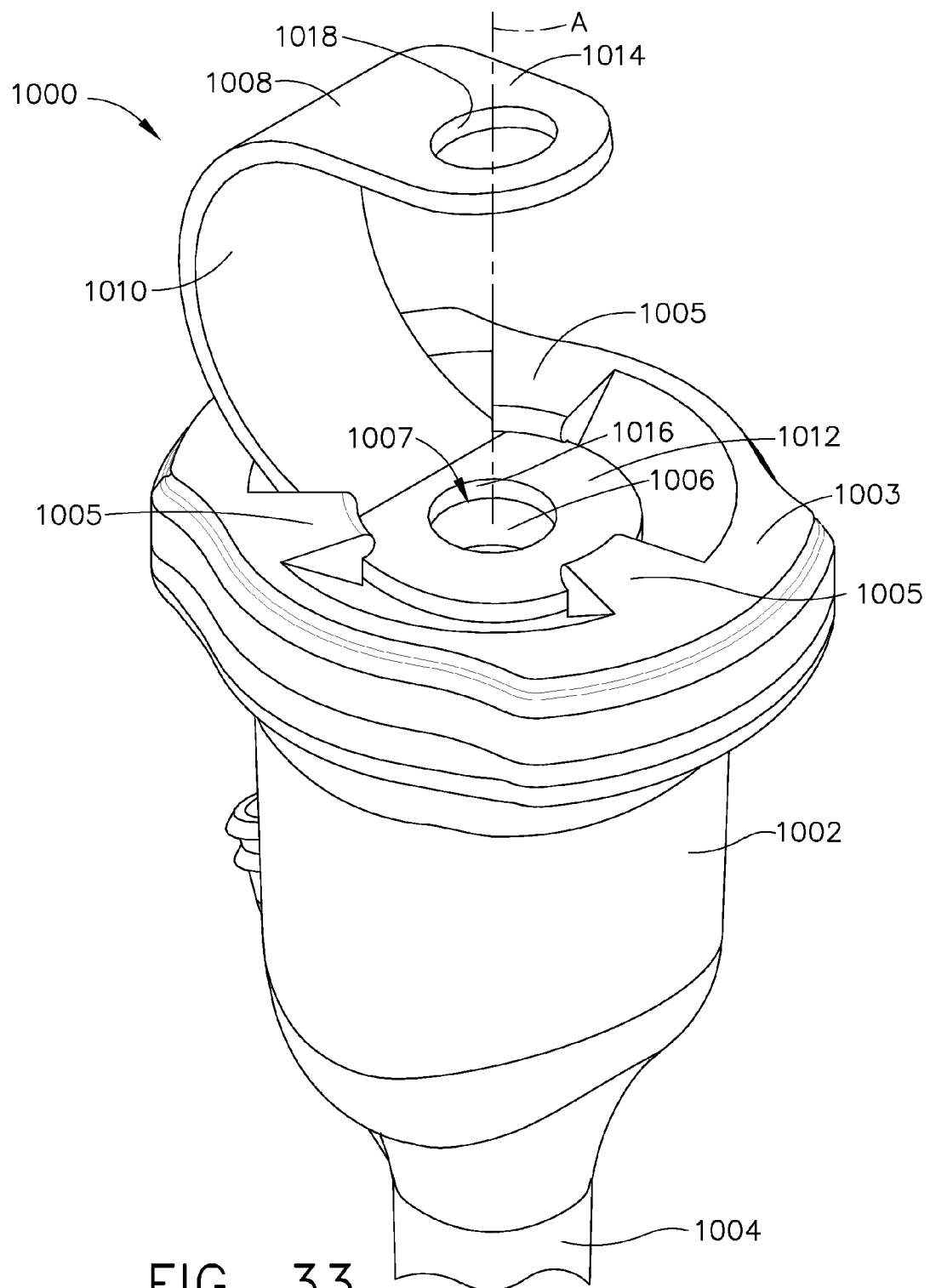
FIG. 33 is a front perspective view of a portion of a trocar assembly having a scope supporting mechanism in accordance with a third aspect of the disclosure.

Referring to FIG. 33, in a second alternative aspect, an obturator assembly, generally designated 1000, may include a handle 1002 connected to an obturator 1004, wherein the handle 1002 includes a channel 1006 extending therethrough and coupled to a channel (not shown) extending through the obturator 1004 to define a working channel 1007 in the obturator assembly 1000. A support mechanism 1008 may be connected to the handle 1002 of the obturator assembly 1000 to engage a medical instrument (not shown) inserting into the working channel.

The support mechanism 1008 may include a band 1010 having a first end portion 1012 and a second end portion 1014. The first end portion 1012 of the band 1010 may define a first opening 1016 therein and the second end portion 1014 may define a second opening 1018 therein. The first end portion 1012 of the band 1010 may be connected to the proximal end 1003 of the handle 1002 such that the first and second openings 1016, 1018 may be coaxially aligned with the longitudinal axis A of the obturator assembly 1000. For example, the first end portion 1012 of the band 1010 may be retained against the proximal end 1003 of the handle 1002 by tabs 1005 formed in the proximal end 1003 of the handle 1002 and positioned over the end portion 1012 of the band 1010.

In one aspect, the band 1010 may act as a dawl to engage a medical instrument inserted into the working channel 1007. In another aspect, the first and second openings 1016, 1018 may have an inner diameter that is slightly smaller than the outer diameter of the medical instrument to be inserted into the working channel 1007 such that the band 1010 engages the medical instrument to support the medical instrument in a desired axial, circumferential and/or radial position in the working channel 1007. For example, the band 1010 may be formed from a slightly rigid, yet resiliently deformable material, such as polyurethane.

Figures 34, 35:
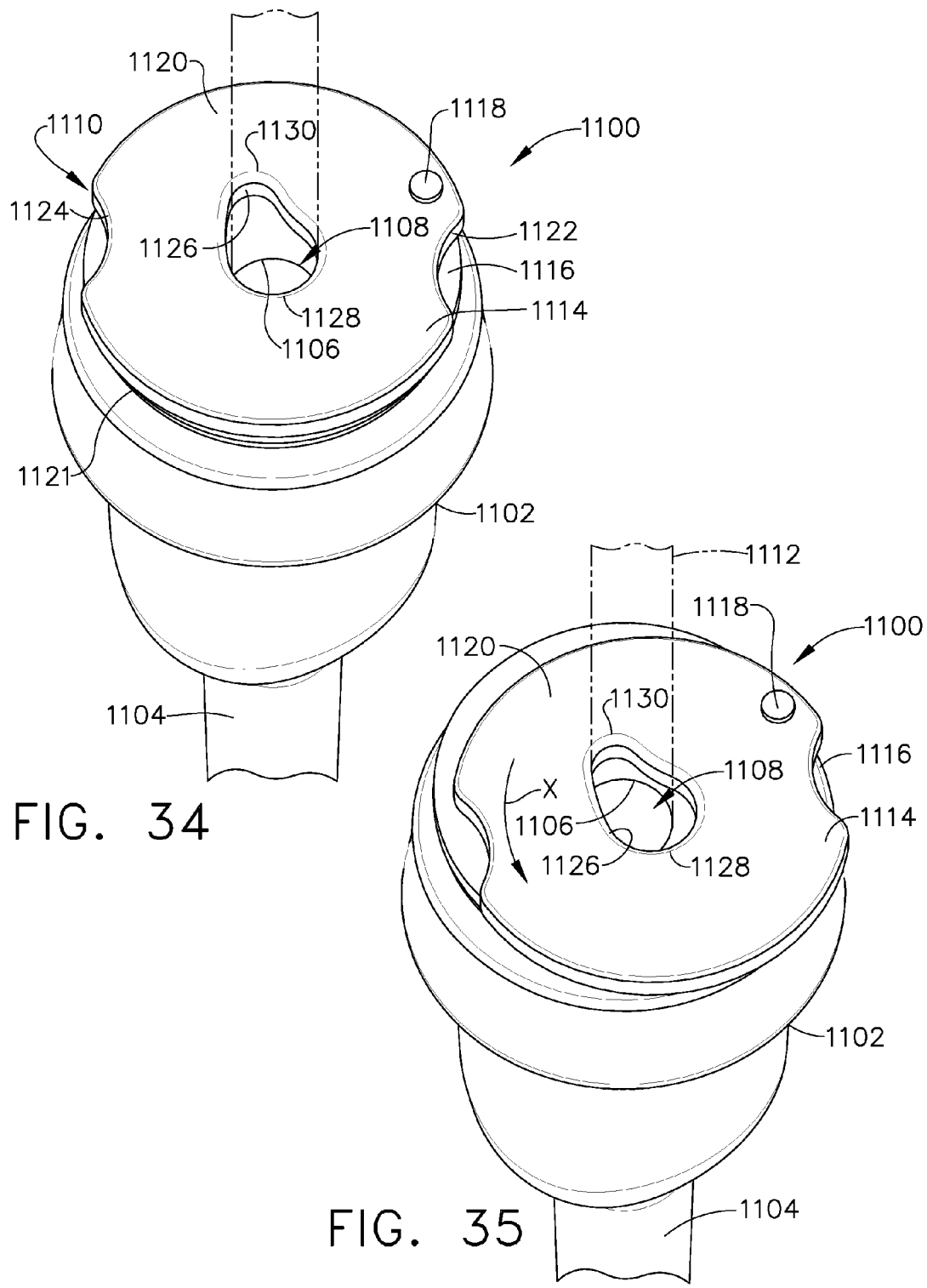
FIG. 34 is a top perspective view of a portion of a trocar assembly having a scope supporting mechanism in accordance with a fourth aspect of the disclosure.
FIG. 35 is a top perspective view of the portion of the trocar assembly of FIG. 34 shown supporting a scoping device.

Referring to FIGS. 34 and 35, in a third alternative aspect, an obturator assembly, generally designated 1100, may include a handle 1102 connected to an obturator 1104, wherein the handle 1102 includes a channel 1106 extending therethrough and coupled to a channel (not shown) extending through the obturator 1004 to define a working channel 1108 in the obturator assembly 1000. A support mechanism 1110 may be connected to the handle 1102 of the obturator assembly 1000 to engage a medical instrument 1112 (FIG. 35) inserting into the working channel 1108.

The support mechanism 1110 may include a plate 1114 pivotally connected to the proximal end 1116 of the handle 1102 at a pivot point 1118. The plate 1114 may include a proximal end 1120 and a distal end 1121 that slides along the proximal end 1116 of the housing 1102. Indented gripping portions 1122, 1124 may be formed in the plate 1114 to facilitate manipulation of the plate 1114 relative to the handle 1102.

The plate 1114 may define a tear drop-shaped opening 1126 that extends from the proximal end 1120 to the distal end 1121 of the plate 1114. The opening 1126 may include a wide end portion 1128 and a narrow end portion 1130. As shown in FIG. 34, the wide end 1128 of the opening 1126 may be aligned with the channel 1106 in the handle 1102 when the plate is in a first position to allow a medical instrument 1112 to be inserted through the plate 1114 and into the working channel 1108 of the obturator assembly 1110. Then, as shown in FIG. 35, the plate 1114 may pivot relative to the handle 1102 in the direction shown by arrow X such that the wide end portion 1128 of the opening 1126 is misaligned with the channel 1106 in the handle 1102 and the narrow end portion 1130 of the opening 1126 engages the medical instrument 1112. Therefore, those skilled in the art will appreciate that the wide end portion 1128 of the opening 1126 may be larger than the outer diameter of the medical instrument 1112, while the narrow end portion 1120 may be smaller than the outer diameter of the medical instrument 1112.

Optionally, while not shown, a biasing element, such as a leaf spring may act on the plate 1114 to bias the plate in the direction shown by arrow X (i.e., an engagement position).

Figure 36:
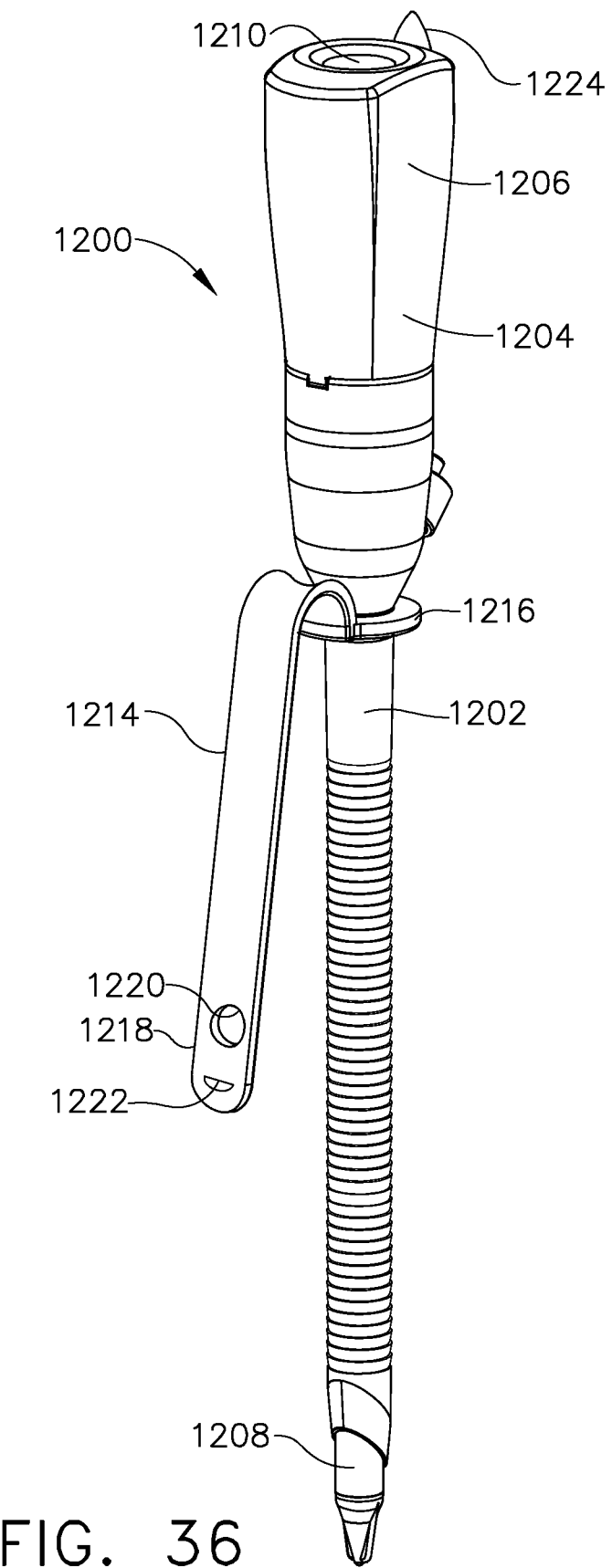
FIG. 36 is a front perspective view of a trocar assembly having a scope supporting mechanism in accordance with a fifth aspect of the disclosure.
Figure 37:
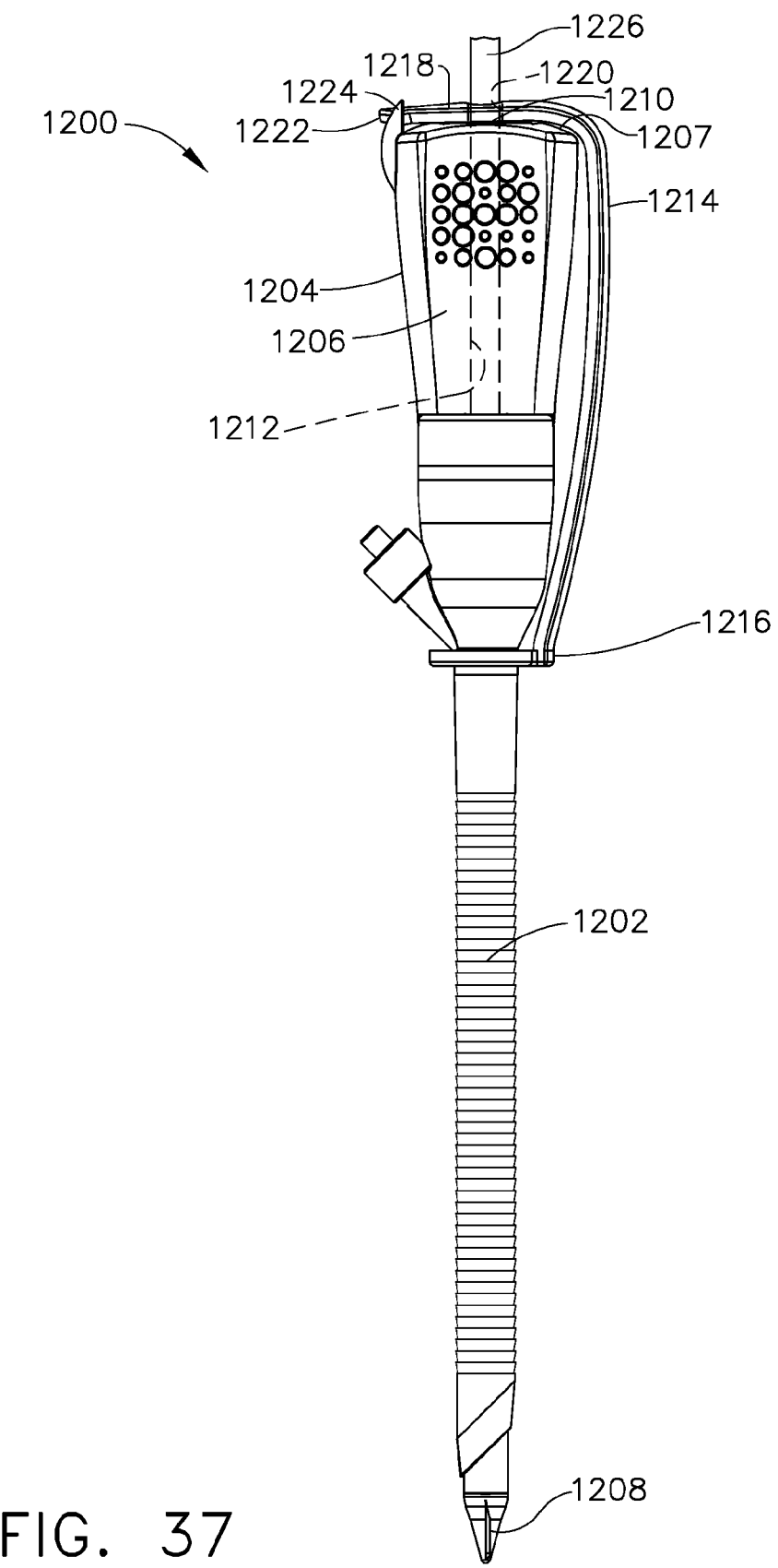
FIG. 37 is a front perspective view of the trocar assembly of FIG. 36 shown supporting a scoping device.

Referring to FIGS. 36 and 37, in a fourth alternative aspect, a trocar assembly, generally designated 1200, may include a sleeve assembly 1202, an obturator assembly 1204 and support mechanism 1206. The obturator assembly 1204 may include a handle 1206 connected to an obturator 1208, wherein the handle 1206 defines an opening 1210 into a working channel 1212 of the obturator assembly 1204.

The support mechanism 1206 may include a flexible strap 1214 having a first end portion 1216 and a second end portion 1218. The first end portion 1216 of the strap 1214 may be connected to the sleeve portion 1202. Alternatively, the first end portion 1216 of the strap 1214 may be connected to some other portion of the trocar assembly 1200, such as the handle 1206 of the obturator assembly 1204. The second end portion 1218 of the strap 1214 may define a first opening 1220 therein and, optionally, a second opening 1222 therein.

As shown in FIG. 37, the strap 1214 may be extendable from the sleeve 1202 over the proximal end 1207 of the handle 1206 such that the first opening 1220 in the strap 1214 may be coaxially aligned with the opening 1210 in the handle 1206 and the working channel 1212 of the obturator assembly 1204. A projection 1224 extending from the handle 1206 may be received through the second opening 1222 in the strap 1214 to secure the strap 1214 to the handle 1206, thereby also securing the obturator assembly 1204 to the sleeve assembly 1202.

Accordingly, as shown in FIG. 37, a medical instrument 1226 may pass through the first opening 1220 in the strap 1214 before passing through the working channel 1212 of the obturator assembly 1204. In one particular aspect, the first opening 1220 in the strap 1214 may have an inner diameter that is slightly smaller than the outer diameter of the medical instrument 1226 such that the strap 1214 engages the medical instrument 1226 to support the medical instrument 1226 in a desired axial, circumferential and/or radial position in the working channel 1212.

Figure 38:
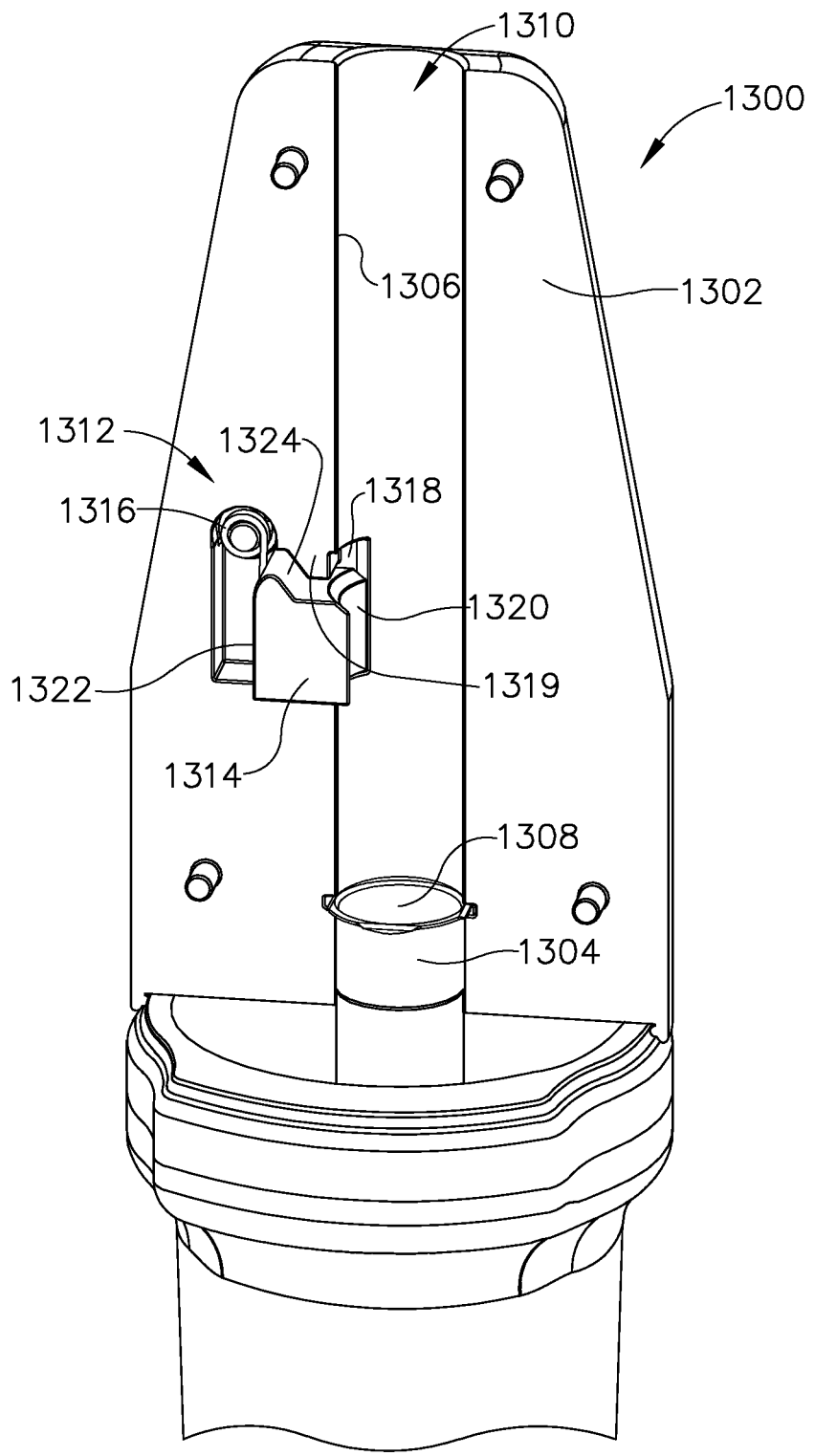
FIG. 38 is a front perspective view, partially in section, of a portion of a trocar assembly having a scope supporting mechanism in accordance with a sixth aspect of the disclosure.

Referring to FIG. 38, in a fifth alternative aspect, an obturator assembly, generally designated 1300, may include a handle 1302 connected to an obturator 1304, wherein the handle 1302 includes a channel 1306 extending therethrough and coupled to a channel 1308 extending through the obturator 1304 to define a working channel 1310 of the obturator assembly 1300. A support mechanism 1312 may be received in the channel 1306 of the handle 1302 to engage a medical instrument (not shown) inserting into the working channel 1310.

The support mechanism 1312 may include an engagement member 1314 and a biasing element 1316 received in a bore 1318 that extends into the handle 1302 from the channel 1306. The engagement member 1314 may include a first, inner end 1320, a second, outer end 1322 and a stop 1324. The first end 1320 may be shaped (e.g., curved) to correspond with the shape of the working channel 1310 and/or the medical instrument (not shown) to be inserted into the working channel 1310.

The biasing element 1316 (e.g., a leaf spring) may be disposed between the bore 1318 and the second end 1322 of the engagement member 1314 to bias the engagement member 1314 radially inward into the channel 1306 such that the first end 1320 of the engagement member 1314 may apply a radial force to a medical instrument (not shown) received in the channel 1306. The stop 1324 may be positioned to engage a flange 1319 defined by the bore 1318 to limit radially inward movement of the engagement member 1314 by a predetermined distance.

Figure 39:
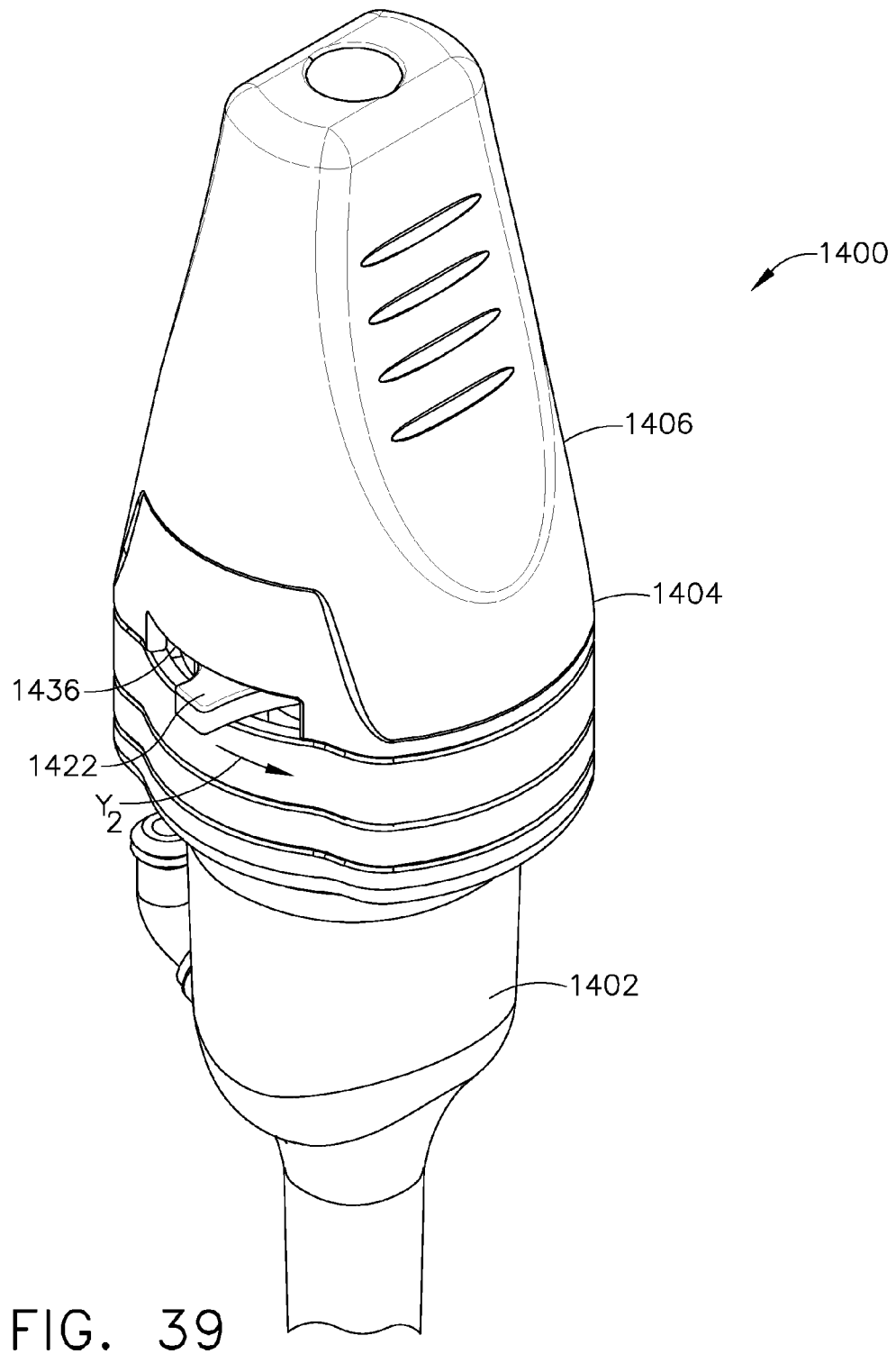
FIG. 39 is a front perspective view of a portion of a trocar assembly having a scope supporting mechanism in accordance with a seventh aspect of the disclosure.
Figure 40:
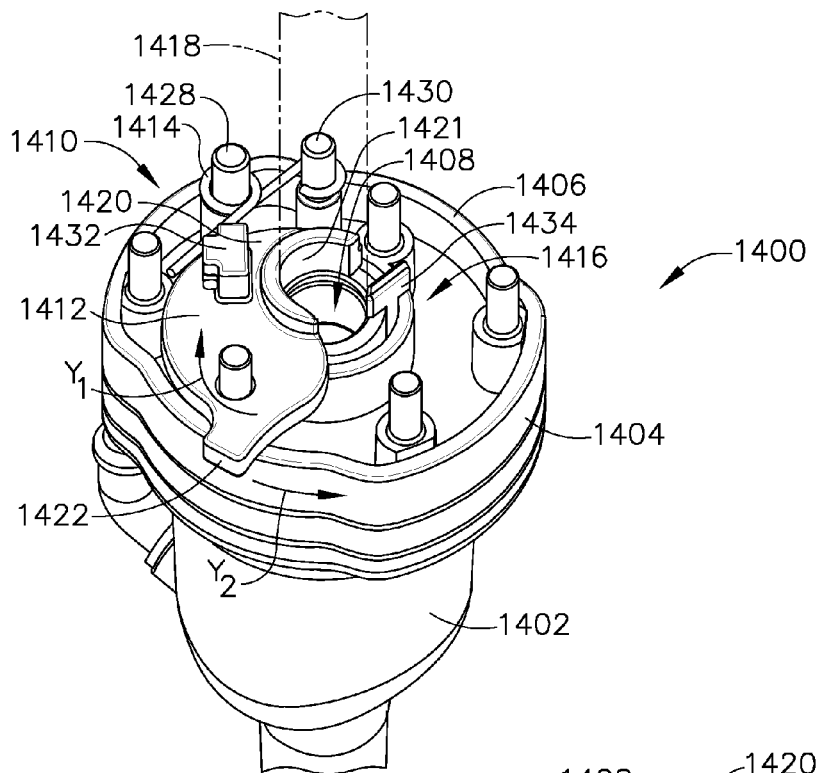
FIG. 40 is a front perspective view of the trocar assembly of FIG. 39 shown supporting a scoping device, wherein a portion of the obturator handle has been removed to shown underlying structure.
Figure 41:
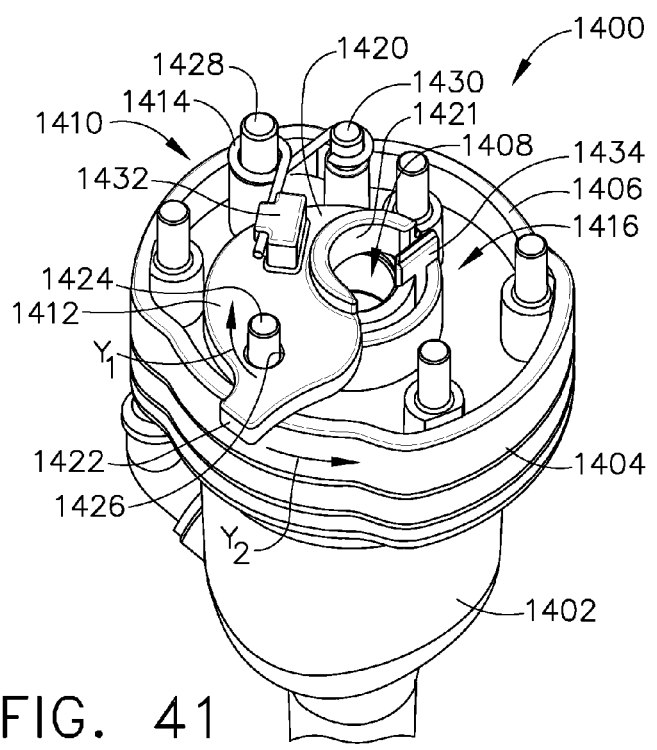
FIG. 41 is a front perspective view of the trocar assembly of FIG. 40, shown with the scoping device removed.

Referring to FIGS. 39-41, in a sixth alternative aspect, a trocar assembly, generally designated 1400, may include a sleeve assembly 1402 and an obturator assembly 1404. The obturator assembly 1404 may define a working channel 1408 extending therethrough, and may include a handle 1406 connected to an obturator (not shown) that extends through the sleeve assembly 1402.

The handle 1406 of the obturator assembly 1404 may include a support mechanism 1410 for engaging a medical instrument 1418 (FIG. 40) received in the working channel 1408. The support mechanism 1410 may include an engagement member 1412 and a biasing element 1414 received in a chamber 1416 defined by the handle 1406. The engagement member 1412 may include a first end 1420 and a second end 1422, and may be pivotally connected to the handle 1406. For example, a pivot post 1424 connected to the handle 1406 may extend through a pivot hole 1426 in the engagement member 1412 such that the engagement member 1412 may pivot relative to the handle 1406, as shown by arrow $Y_1$.

The first end 1420 of the engagement member 1412 may include an engagement surface 1421 shaped to correspond to the shape of the medical instrument 1418 received in the working channel 1408. For example, the engagement surface 1421 may be semi-cylindrical to mate with a generally cylindrical medical instrument 1418.

The biasing element 1414 may be a spring and may be mounted on posts 1428, 1430 connected to the handle 1406. The biasing element 1414 may act on the engagement member 1412 to bias the engagement member 1412 radially inward into the working channel 1408. For example, the biasing element 1414 may apply a biasing force to a protrusion 1432 of the engagement member 1412 to urge the engagement surface 1421 radially inward into the working channel 1408 to engage a medical instrument 1418 received in the working channel 1408. A stop 1434 connected to the handle 1406 may limit travel of the engagement member 1412 in the direction of arrow $Y_1$ when the medical instrument 1418 is not received in the working channel 1408.

As shown in FIG. 39, the second end 1422 of the engagement member 1412 may extend through an opening 1436 the handle 1406 and may be manipulated by the practitioner. A force (arrow $Y_2$) may be manually applied by the user to the second end 1422 of the engagement member 1412 to overcome the biasing force of the biasing element 1414 and pivot the engagement surface 1421 radially outward and away from the working channel 1408, thereby disengaging the engagement surface 1421 from the medical instrument 1418 received in the working channel 1408, allowing the medical instrument 1418 to be freely moved.

Referring to FIGS. 64-67, in a seventh alternative aspect, a trocar assembly, generally designated 2300, may include a sleeve assembly 2302 and an obturator assembly 2304. The obturator assembly 2304 may include a handle 2306 connected to an obturator (not shown), and may define a working channel 2308 extending through the handle 2306 and the obturator.

A scope supporting mechanism 2310 may be connected to the handle 2306 to engage a scoping device (not shown) inserted into the working channel 2308. The scope supporting mechanism 2310 may include a first portion 2312 having a first biconvex lens-shaped opening 2314 therein and a second portion 2316 having a second biconvex lens-shaped opening 2318 therein, wherein the second portion 2316 is proximal to and rotatable about longitudinal axis Z relative to the first portion 2312. Specifically, the second portion 2316 may rotate relative to the first portion 2312 between at least a first configuration, wherein the second biconvex lens-shaped opening 2318 is aligned with the first biconvex lens-shaped opening 2314, and a second configuration (FIG. 67), wherein the second biconvex lens-shaped opening 2318 is disposed at an angle θ' relative to the first biconvex lens-shaped opening 2314.

Thus, a scoping device may freely pass through the openings 2314, 2318 of the first and second portions 2312, 2316 and into the working channel 2308 of the obturator assembly 2304, when the second portion 2316 is in the first configuration. However, in the second configuration, the second portion 2316 may interfere with the first opening 2314 in the first portion 2312, thereby forming a smaller net opening 2320 that engages a scoping device inserted therethrough.

Referring again to FIG. 32, the handle 102 of the obturator assembly 114 and the housing 20 (including the cap 56) of the sleeve assembly 12 may define a gripping portion 140 of the trocar assembly 10. The gripping portion 140 may have an overall axial length $L_T$, which may be comprised of the axial length $L_O$ of the obturator handle 102 and the axial length $L_S$ of housing 20, and a maximum width W in the radial direction, which may be the greatest width of either the handle 102 of the obturator assembly 114 or the housing 20 of the sleeve assembly 12. To provide the trocar assembly 10 with a low profile that does not overly crowd the surgical site, but still has a gripping portion that can easily be manipulated by the user, similar to the grip of a screwdriver handle, the ratio of the axial length $L_T$ to the maximum width W may be at least 2, such as about 2.5 to about 3.5. For example, in one embodiment, the trocar assembly 10 may have an axial length $L_T$ of about 5.25 inches and a maximum width W of about 1.875 inches, which provides a length-to-width ratio of about 2.8.

In one particular aspect, it may be desirable that the axial length $L_O$) of the obturator handle 102 provides the greatest contribution to the overall axial length $L_T$ of the gripping portion 140, thereby allowing the overall size, including the axial length $L_S$, of the housing 20 of the sleeve assembly 12 to be minimized to allow for stacking multiple trocar sleeve assemblies, which may have different heights, in a tight surgical site.

Figure 58:
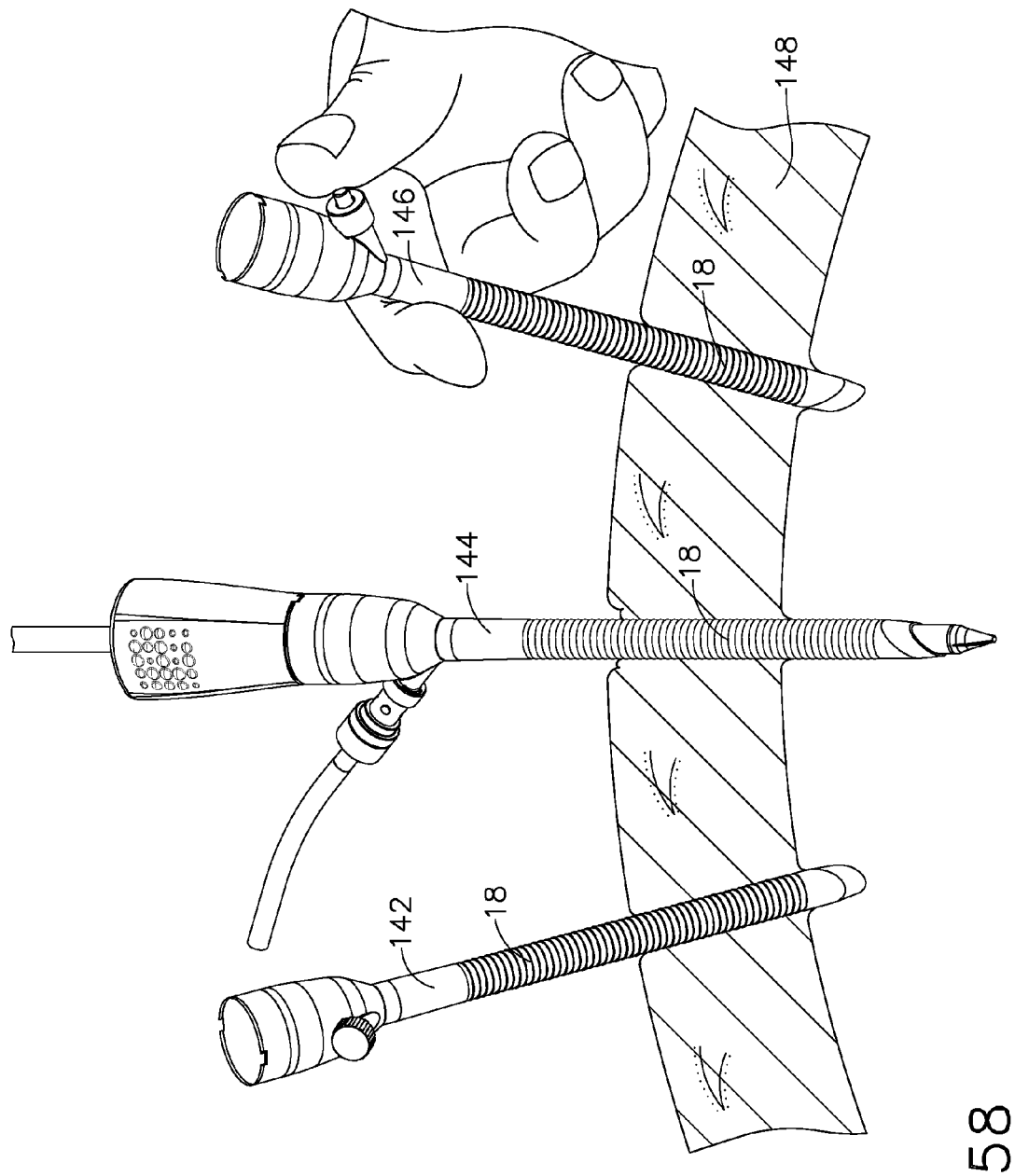
FIG. 58 is a perspective view of multiple trocars inserted through the abdominal wall of a patient.

Those skilled in the art will appreciate that two or more trocar assemblies 10 may be used during a surgical procedure. For example, FIG. 58 shows one trocar assembly 144 and two trocar sleeve assemblies 142, 146 inserted through the abdominal wall 148 of a patient during a surgical procedure. Depending on the location of the surgical procedure, trocar sleeve assemblies having cannulas 18 of different lengths (e.g., 65 mm, 75 mm, 110 mm or 125 mm) may be required. Therefore, the disclosed trocar assemblies 10 may be packaged into kits comprising two or more trocar assemblies each. As one example, a kit may include a trocar assembly 10 having a 75 mm cannula and a trocar assembly 10 having a 125 mm cannula. As another example, a kit may include a trocar assembly 10 having one 65 mm cannula and two trocar sleeve assemblies 12 having 110 mm cannulas. Also in the kit, one of the trocars may have an insufflation port, others may have a venting port, a still others may have a plugged port or no port at all. Various other kit combinations will be readily apparent to those having ordinary skill in the art upon reading the present disclosure.

At this point, those skilled in the art will appreciate that kits containing trocars of various heights present various advantages. One such example includes the ability to use multiple trocars in close proximity since the housings of the different trocars are less likely to interfere. Another example is the ability to use only one trocar sleeve assembly of the kit for venting, while the insufflation ports of the other trocar sleeve assemblies may be plugged.

Referring to FIGS. 2 and 3, an insufflation valve assembly 16 may be coupled to the insufflation port 42 of the sleeve assembly 12 to facilitate control over the supply and/or venting of insufflation fluid.

In accordance with a first aspect, the disclosed insufflation valve assembly 16 may include a housing 150, a valve member 152, a biasing element 154, a first sealing member 156 and a second sealing member 158. The valve member 152 may be a generally tubular member and may include an inlet port 160 that defines an inlet channel 162, an outlet port 164 that defines an outlet channel 166, a bulkhead 168 that separates the inlet channel 162 from the outlet channel 166, and a flange 170 extending radially outward from the inlet port 160. The outlet channel may be in fluid communication with the working channel 36 of the sleeve assembly 12 by way of the channel 44 of the insufflation port 42.

The first sealing member 156 may be an O-ring and may be connected to the housing 150 and may be disposed between the valve member 152 and the housing 150 to define a pressurized chamber 157 and a venting chamber 159 within the housing 150. The second sealing member 152 may be an O-ring and may be received in an annular groove 153 formed in the outlet port 164 of the valve member 152 and may engage a valve seat 161 defined by, or otherwise connected to, the housing 150.

A first set of openings 172 may extend radially through the inlet port 160 and into the inlet channel 162 between the flange 170 and the bulkhead 168 to provide fluid communication between the inlet channel 162 and the pressurized chamber 157. A second set of openings 174 may extend radially through the outlet port 164 and into the outlet channel 166 to provide fluid communication between the outlet channel 166 and either the pressurized chamber 157 or the venting chamber 159 depending on the axial position of the valve member 152 relative to the housing 150. A third set of openings 180 may extend through the housing 150 to provide fluid communication between the venting chamber 159 and the atmosphere. Optionally, the third set of openings 180 may extend through the housing 150 at an angle to direct venting gasses downward or otherwise away from the practitioner.

The biasing element 154 may be a coil spring or the like and may be coaxially received over the valve member 152 to apply a biasing force (arrow $F_1$) against the flange 170 to urge the valve member 152 outward through an opening 178 in the housing 150 and to urge the second sealing member 158 against the seat 161, as shown in FIG. 2. Stops 176 or the like may extend inward from the housing 150 to counteract the biasing force of the biasing element 154.

In the configuration shown in FIG. 2 (i.e., the insufflating configuration), both the first and second sets of openings 172, 174 may be in fluid communication with the pressurized chamber 157. Therefore, in the insufflating configuration, an insufflation fluid supplied to the inlet port 160 may flow through the inlet channel 162, through the first set of openings 172 and into the pressurized chamber 157 of the housing 150, then from the pressurized chamber 157 through the second set of openings 174 and into the outlet channel 166 of the outlet port 164, as shown by arrows $E_1$, $E_2$, and, ultimately, to the working channel 36 of the sleeve assembly 12. Furthermore, in the insufflating configuration, the seating of the second sealing member 158 against the seat 161 may fluidly decouple the venting chamber 159 from the outlet channel 166 and the channel 44 of the insufflation port 42.

Referring to FIG. 3, when a sufficient force (arrow $F_2$) is applied to the valve member 152 to overcome the biasing force of the biasing element 154 (i.e., the venting configuration), which may be achieved by a user manually pressing the valve member 152, the second sealing member 158 may disengage the seat 161 and the second set of openings 174 may be shifted into the venting chamber 159, thereby precluding insufflation fluid in the pressurized chamber 157 from passing into the outlet channel 166, while allowing insufflation fluid to pass from the working channel 36, through the channel 44 of the insufflation port 42, to the outlet channel 166 and, ultimately, through the third set of openings 180 in the housing 150 and out to the atmosphere, as shown by arrows $G_1$, $G_2$, $G_3$.

At this point, those skilled in the art will appreciate that the insufflation valve assembly 16 allows for quick and easy venting of insufflation fluid from the abdominal cavity of a patient by presenting a push button that can be manipulated by one hand. The insufflation valve assembly 16 also eliminates the need to disconnect the insufflation fluid supply from the insufflation port 42 to achieve venting.

Figure 5:
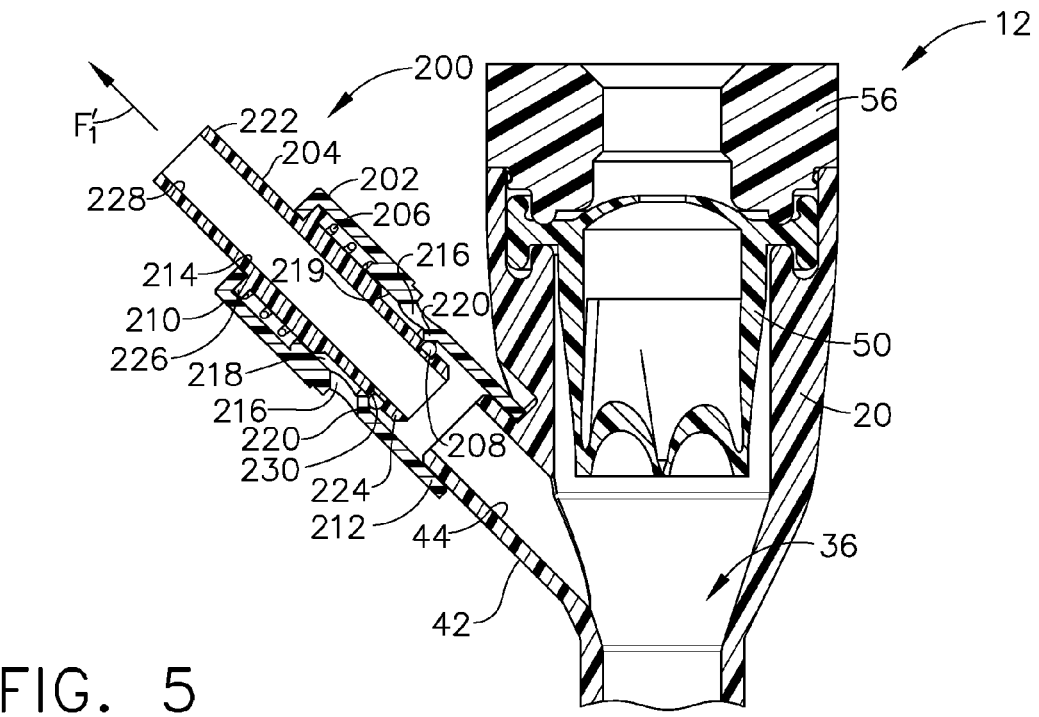
FIG. 5 is a front elevational view, in section, of a portion of a trocar sleeve assembly having an insufflation valve assembly coupled thereto in accordance with a third aspect of the disclosure, wherein the insufflation valve assembly is shown in an insufflating configuration.
Figure 6:
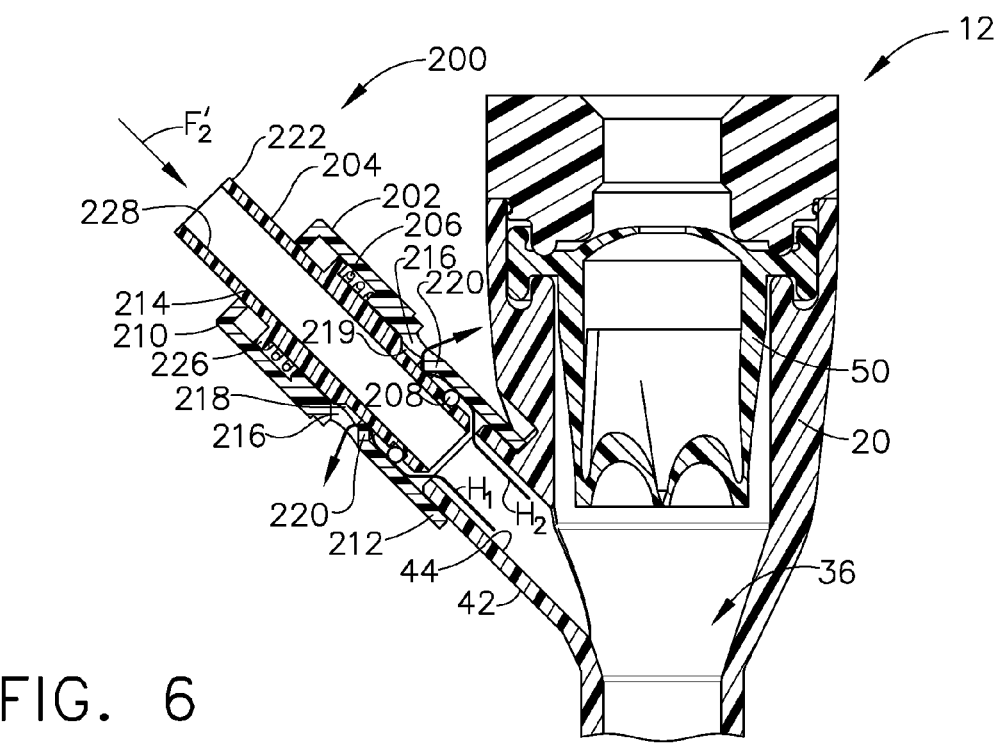
FIG. 6 is a front elevational view, in section, of the sleeve assembly of FIG. 5, wherein the insufflation valve assembly is shown in a venting configuration.

Referring to FIGS. 5 and 6, in accordance with a second aspect, the disclosed insufflation valve assembly 200 may include a housing 202, a valve member 204, a biasing element 206 and a sealing member 208. The housing 202 may be a generally tubular body having a proximal end 210 defining an opening 214 therein and a distal end 212 fluidly coupled to the insufflation port 42 of a trocar sleeve assembly 12. One or more vent holes 216 may extend through the housing 202 to provide fluid communication between the atmosphere and the annular space 218 between the housing 202 and the valve member 204 (i.e., the venting chamber 219). A valve seat 220 may be defined by the housing 202 distal to the vent holes 216.

The valve member 204 may be a generally tubular body received in the housing 202, and may include an open proximal end 222, an open distal end 224, a flange 226 and an elongated channel 228 extending between the open proximal and distal ends 222, 224. The proximal end 222 of the valve member 204 may extend through the opening 214 in the housing 202 and may be fluidly coupled to an insufflation fluid supply (not shown), such that insufflation fluid may flow through the channel 228, into the channel 44 of the insufflation port 42 and, ultimately, into the working channel 36 of the sleeve assembly 12. The distal end 224 of the valve member 204 may include an annular groove 230, and the sealing member 208 (e.g., an O-ring) may be received in the annular groove 230.

As shown in FIG. 5, the biasing element 206 (e.g., a coil spring) may be disposed between the housing 202 and the flange 226 of the valve member 204 to urge the valve member 204 in the proximal direction, as shown by arrow $F_1'$, thereby urging the sealing member 208 against the valve seat 220. With the sealing member 208 seated against the valve seat 220, the venting chamber 219 may be fluidly decoupled from the channel 228 of the valve member 204 and the channel 44 defined by the insufflation port 42.

Referring to FIG. 6, when a sufficient force (arrow $F_2'$) is applied to the valve member 204 to overcome the biasing force of the biasing element 206, the sealing member 208 may disengage the valve seat 220, thereby fluidly coupling the venting chamber 219 with the channel 44 defined by the insufflation port 42 to allow insufflation fluid to vent from the working channel 36, as shown by arrows $H_1$, $H_2$.

Figure 7:
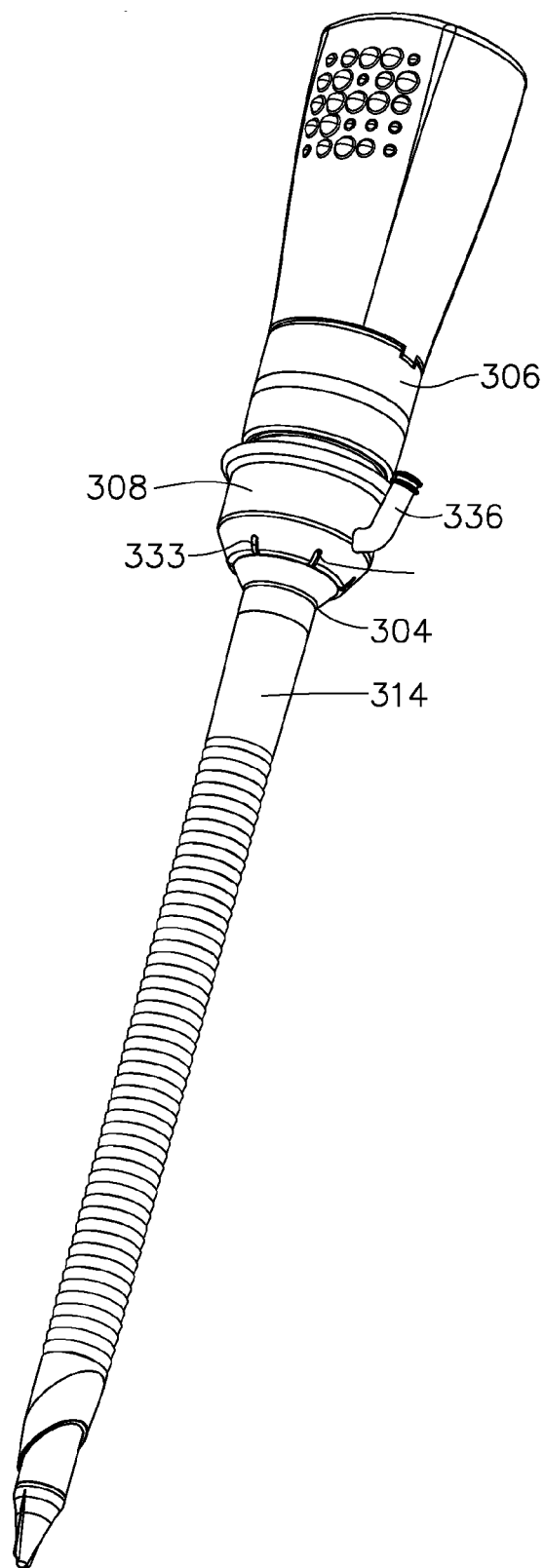
FIG. 7 is a front perspective view of an alternative embodiment of the disclosed trocar assembly, wherein an insufflation valve assembly is housed within a sleeve assembly of the trocar assembly in accordance with a fourth aspect of the disclosure.
Figure 8:
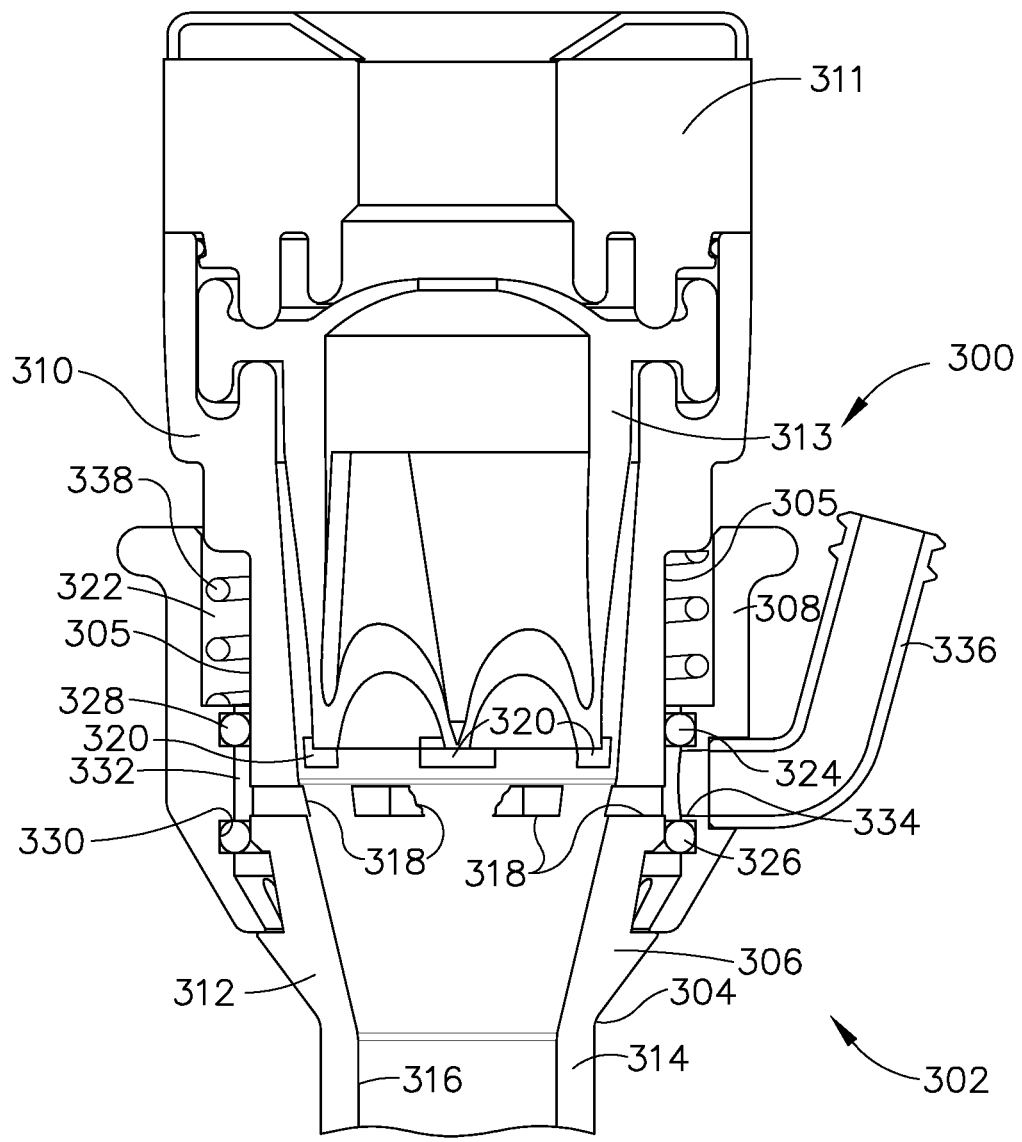
FIG. 8 is a front elevational view, in section, of a portion of the sleeve assembly of the trocar assembly of FIG. 7, wherein the insufflation valve assembly is shown in an insufflating configuration.
Figure 9:
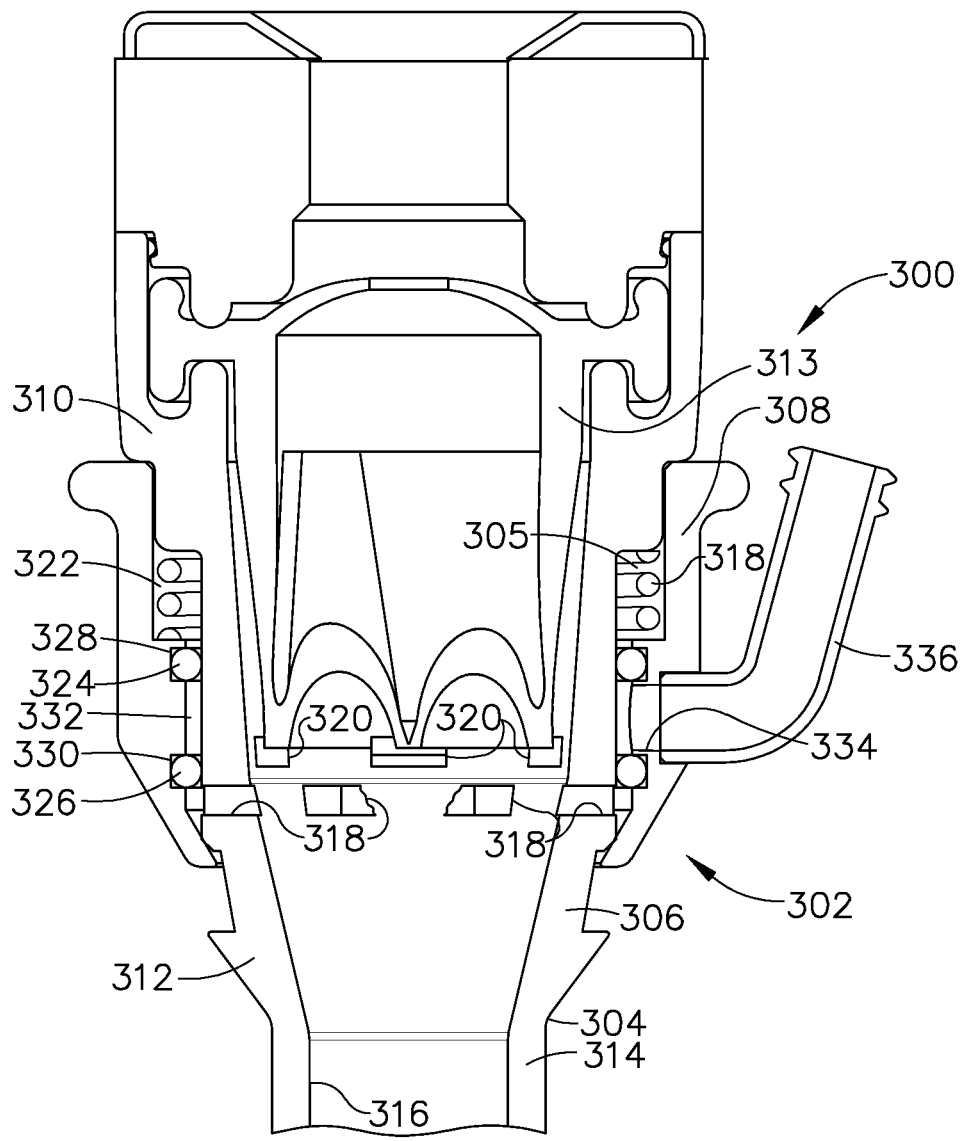
FIG. 9 is a front elevational view, in section, of the sleeve assembly of FIG. 8, wherein the insufflation valve assembly is shown in a venting configuration.

Referring to FIGS. 7-9, in accordance with a third aspect, an insufflation valve assembly, generally designated 300, may be integrated into the housing assembly 302 of a trocar sleeve assembly 304.

As shown in FIGS. 8 and 9, the housing assembly 302 may include a housing 306, a sleeve 308, a first sealing member 324 and a second sealing member 326. The first and second sealing members 324, 326 may be O-rings. Alternatively, the first and second sealing members 324, 326 may be gaskets or the like.

The housing 306 may include a proximal end 310 and a distal end 312. The proximal end 310 of the housing 306 may be connected to a cap 311 to secure a channel seal 313 within the housing 306, as described above. The distal end 312 of the housing 306 may be coupled to a cannula 314 to define a working channel 316, as described above. A first, distal set of openings 318 may extend through the housing 306. A second, proximal set of openings 320 may also extend through the housing 306 proximal to the first, distal set of openings 318.

The sleeve 308 may be slidably and coaxially received over the housing 306 to define an annular region 322 therebetween. The sleeve 308 may define a first groove 328 that receives the first sealing member 324 therein and a second groove 330 that receives the second sealing member 326 therein, such that the first and second sealing members 324, 326 form a seal between the sleeve 308 and the outer wall 305 of the housing 306, thereby defining a sealed pressure chamber 332 within the annular region 322, wherein the pressure chamber 332 is bounded by the housing 306, the sleeve 308, the first sealing member 324 and the second sealing member 326. The portion of the annular region 322 outside of the pressure chamber 332 may be in fluid communication with the atmosphere. Optional vents 333 (FIG. 7) formed in the sleeve 308 may facilitate fluid communication between the annular region 322 (except the pressure chamber 322) and the atmosphere.

A channel 334 may be formed in the sleeve 308 and an insufflation port 336 may be fluidly coupled to the channel 334 such that the insufflation port 336 is in fluid communication with the pressure chamber 332. The insufflation port 336 may be fluidly coupled to a insufflation fluid supply (not shown) to supply the pressure chamber 332 with an insufflation fluid.

As shown in FIG. 8, when the sleeve 308 is in the distal position, the working channel 316 may be in fluid communication with the pressure chamber 332 by way of both the first, distal set of openings 318 and the second, proximal set of openings 320 such that an insufflation fluid may be supplied to the working channel 316. Optionally, a biasing element 338, such as a coil spring, may bias the sleeve 308 to the distal position.

Referring to FIG. 9, when the biasing force of the biasing element 338 is overcome and the sleeve 308 is urged in the proximal direction, the first, distal set of openings 318 are fluidly decoupled from the pressure chamber 332 and, instead, fluidly coupled to atmosphere such that insufflation fluid can vent through the first, distal set of openings 318. However, the second, proximal set of openings 320 may still be in fluid communication with the pressure chamber 332. Therefore, insufflation fluid may pass through the second, proximal set of openings 320 and may immediate exit through the first, distal set of openings 318, thereby creating a partial vacuum (i.e., venturi effect) that draws insufflation fluid from the working channel 316 and out through the first, distal set of openings 318. At this point, those skilled in the art will appreciate that the second, proximal set of openings 320 is optional, and that sufficient venting may be achieved with only the first, distal set of openings 318.

Figure 10:
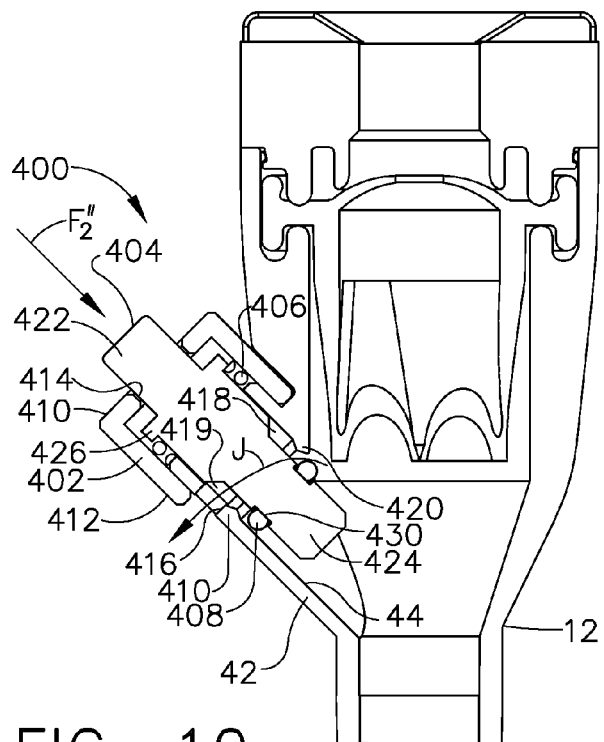
FIG. 10 is a front elevational view, in section, of a portion of a trocar sleeve assembly having an insufflation valve assembly coupled thereto in accordance with a fifth aspect of the disclosure, wherein the insufflation valve assembly is shown in a venting configuration.
Figure 11:
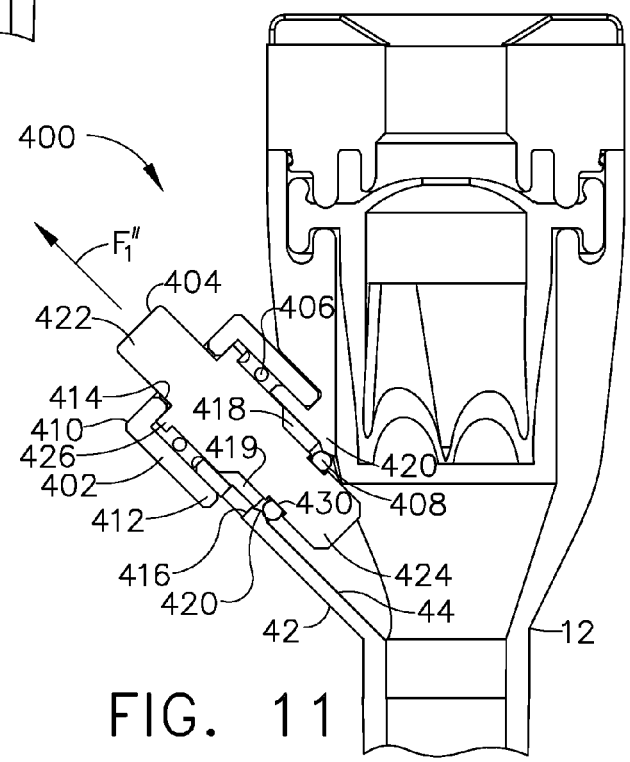
FIG. 11 is a front elevational view, in section, of the sleeve assembly of FIG. 10, wherein the insufflation valve assembly is shown in a sealed configuration.

Referring to FIGS. 10 and 11, in accordance with a fourth aspect, the disclosed insufflation valve assembly 400 may be a venting apparatus and may include a housing 402, a valve member 404, a biasing element 406 and a sealing member 408. The housing 402 may be a generally tubular body having a proximal end 410 defining an opening 414 therein and a distal end 412 fluidly coupled to the insufflation port 42 of a trocar sleeve assembly 12. A vent hole 416 may extend through the housing 402 to provide fluid communication between the atmosphere and the annular space 418 between the housing 402 and the valve member 404 (i.e., the venting chamber 419). A valve seat 420 may be defined by the housing 402 distal to the vent holes 416.

The valve member 404 may be an elongated, solid body received in the housing 402, and may include a proximal end 422, an open distal end 424 and a radially extending flange 426. The proximal end 422 of the valve member 404 may extend through the opening 414 in the housing 402. The distal end 424 of the valve member 204 may include an annular groove 430, and the sealing member 408 (e.g., an O-ring) may be received in the annular groove 430.

As shown in FIG. 11, the biasing element 406 (e.g., a coil spring) may be coaxially received over the valve member 404 and may apply a biasing force to the flange 426 of the valve member 404 to urge the valve member 204 in the proximal direction, as shown by arrow $F_1''$, thereby urging the sealing member 408 against the valve seat 420. With the sealing member 408 seated against the valve seat 420, the venting chamber 419 may be fluidly decoupled from the channel 44 defined by the insufflation port 42.

As shown in FIG. 10, when a sufficient force (arrow $F_2''$) is applied to the proximal end 422 of the valve member 404 to overcome the biasing force of the biasing element 406, the sealing member 408 may disengage the valve seat 420, thereby fluidly coupling the venting chamber 419 with the channel 44 defined by the insufflation port 42 to allow insufflation fluid to vent through the vent hole 416, as shown by arrow J.

Figure 12:
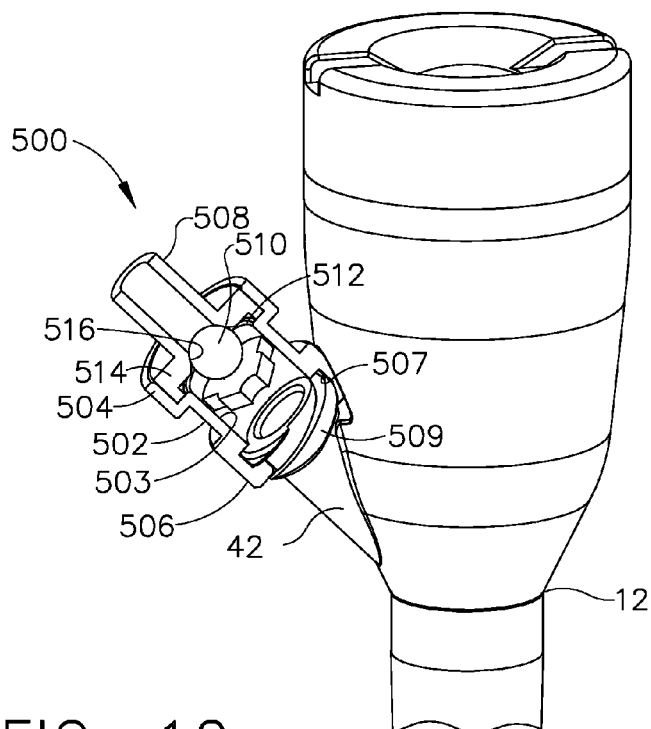
FIG. 12 is a front perspective view, partially in section, of a portion of a trocar sleeve assembly having an insufflation valve assembly coupled thereto in accordance with a sixth aspect of the disclosure, wherein the insufflation valve assembly is shown in a sealed configuration.
Figure 13:
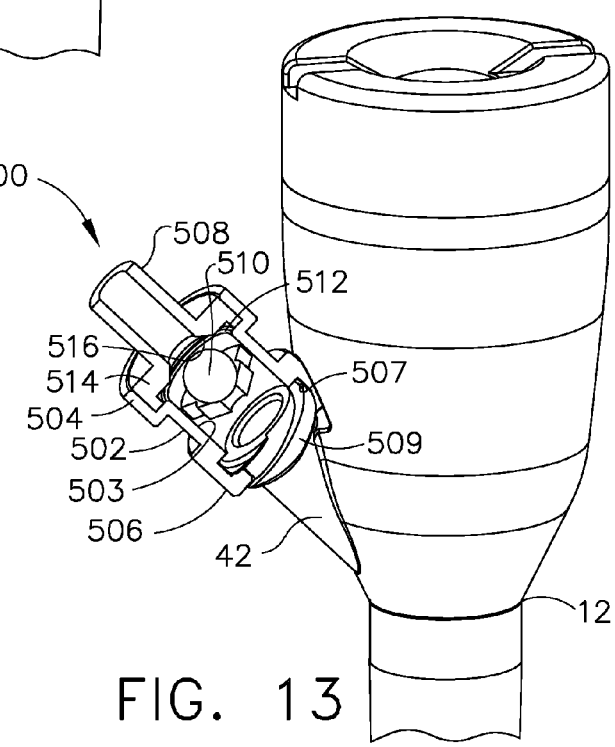
FIG. 13 is a front perspective view, partially in section, of the sleeve assembly of FIG. 12, wherein the insufflation valve assembly is shown in an open, insufflating configuration.

Referring to FIGS. 12 and 13, in accordance with a fifth aspect, the disclosed insufflation valve assembly 500 may include a housing 502 defining an internal volume 503 and having a proximal end 504 and a distal end 506, an inlet port 508, a ball 510 and a biasing element 512. The distal end 506 of the housing 502 may be releasably, fluidly coupled to the insufflation port 42 of a trocar sleeve assembly 12. For example, the distal end 506 of the housing 502 may include threads 507 that engage corresponding threads 509 on the insufflation port 42.

The inlet port 508 may be connected to the proximal end 504 of the housing 502 and may include a distal end 514 that defines valve seat 516, which may be angled or chamfered, and that opens into the internal volume 503 of the housing 502. The ball 510 be received in the internal volume 503 of the housing 502, and may be sized and shaped to engage the valve seat 516 to seal the inlet port 508.

As shown in FIG. 13, the biasing element 512 (e.g., a coil spring) may be positioned between the inlet port 508 and the ball 510 to bias the ball 510 away from the valve seat 516, thereby opening the insufflation valve assembly 500 to allow flow of insufflation fluid from the inlet port, through the internal volume 503 of the housing 502 and, ultimately, through the insufflation port 42 of the trocar sleeve assembly 12.

As shown in FIG. 12, when the pressure within the internal volume 503 of the housing 502 increases to a point sufficient to overcome the biasing force of the biasing element 512, the ball 510 is urged against the valve seat 516 thereby sealing the inlet port 508 and preventing the introduction of additional insufflation fluid. Those skilled in the art will appreciate that the biasing force of the biasing element 512 may be tuned to close the insufflation valve assembly 500 at a predetermined insufflation pressure. Therefore, insufflation valve assembly 500 may be used to prevent over insufflating the abdominal cavity of a patient.

Figure 14:
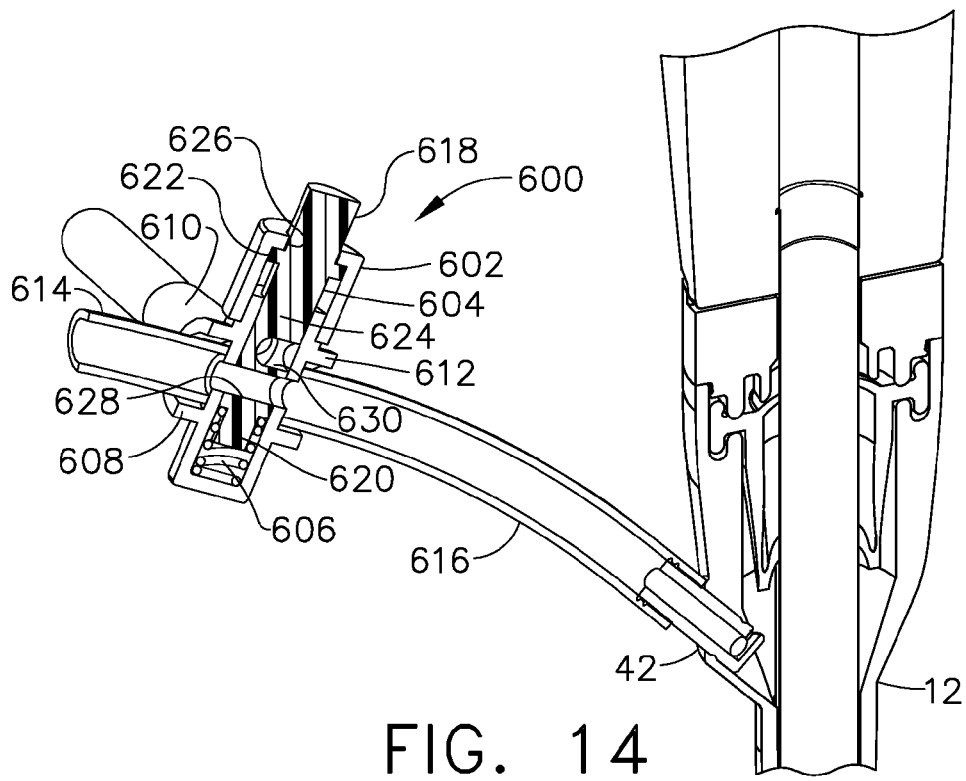
FIG. 14 is a front perspective view, in section, of a portion of a trocar assembly having an insufflation valve assembly coupled thereto in accordance with a seventh aspect of the disclosure, wherein the insufflation valve assembly is shown in a closed configuration.
Figure 15:
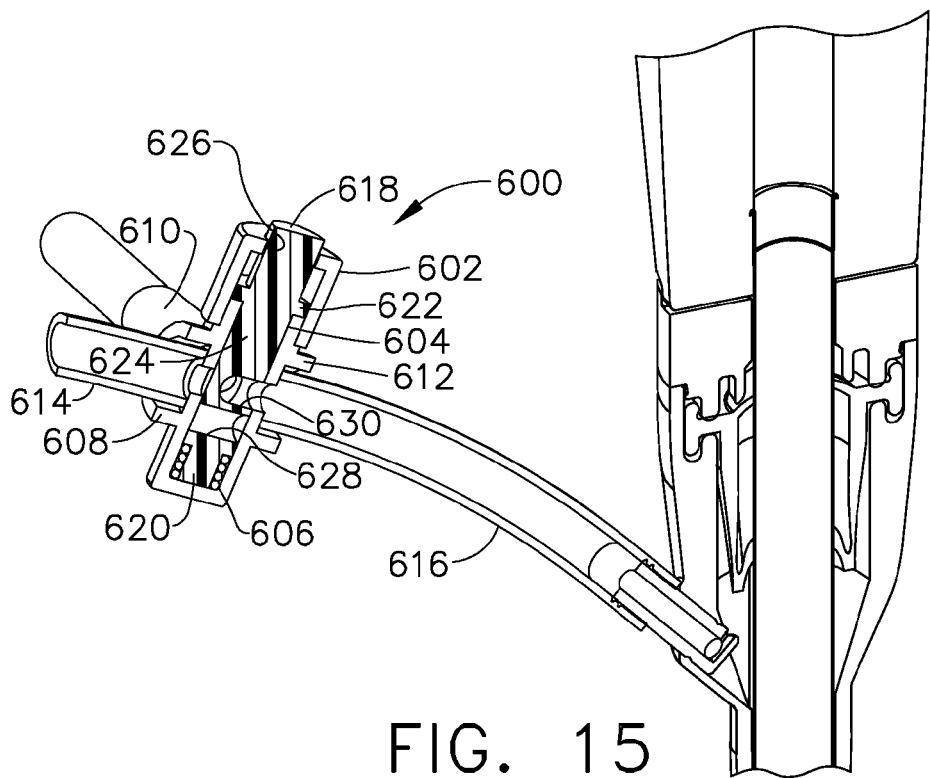
FIG. 15 is a front perspective view, in section, of the trocar assembly of FIG. 14, wherein the insufflation valve assembly is shown in an open, venting configuration.

Referring to FIGS. 14 and 15, in accordance with a sixth aspect, the disclosed insufflation valve assembly, generally designated 600, may be a diverter valve assembly and may include a housing 602, a valve member 604 received in the housing 602, and a biasing element 606. The housing 602 may include a first port 608, a second port 610 and a third port 612. The first port 608 may be fluidly coupled to a supply of insufflation fluid (not shown) by way of a pliable (e.g., rubber) hose 614 or the like. The second port 610 may be open to the atmosphere. The third port 612 may be fluidly coupled to the insufflation port 42 of a trocar sleeve assembly 12 by way of a pliable hose 616 or the like.

The valve member 604 may include body 624 having a proximal end 618 and a distal end 620, and flange 622 extending radially outward from the body 624. The biasing element 606 may apply a biasing force to the distal end 620 of the valve member 604 such that the proximal end 618 of the valve member 604 extends through an opening 626 in the housing 602. The flange 622 may limit movement of the valve member 604 relative to the housing 602 in the proximal direction.

The body 624 of the valve member 604 may define a first fluid channel 628 configured to fluidly couple the first port 608 with the third port 612 and a second fluid channel 630 configured to fluidly couple the second port 610 with the third port 612, depending on the relative axial position of the valve member 604 relative to the housing 602. In the configuration shown in FIG. 14, the biasing element 606 urges the flange 622 proximally against the housing 602, thereby aligning the first fluid channel 628 with the first and third ports 608, 612 to fluidly couple the insufflation port 42 with the insufflation fluid supply. As shown in FIG. 15, when the biasing force of the biasing element 606 is overcome, the valve member 604 may be urged in the distal direction relative to the housing 602 to align the second fluid channel 630 with the second and third ports 610, 612 to fluidly couple the insufflation port 42 with the atmosphere for venting, while fluidly isolating the insufflation port 42 from the insufflation fluid supply.

In accordance with a seventh aspect, an insufflation valve assembly may be integrated into the insufflation port of a trocar sleeve assembly.

Figure 16:
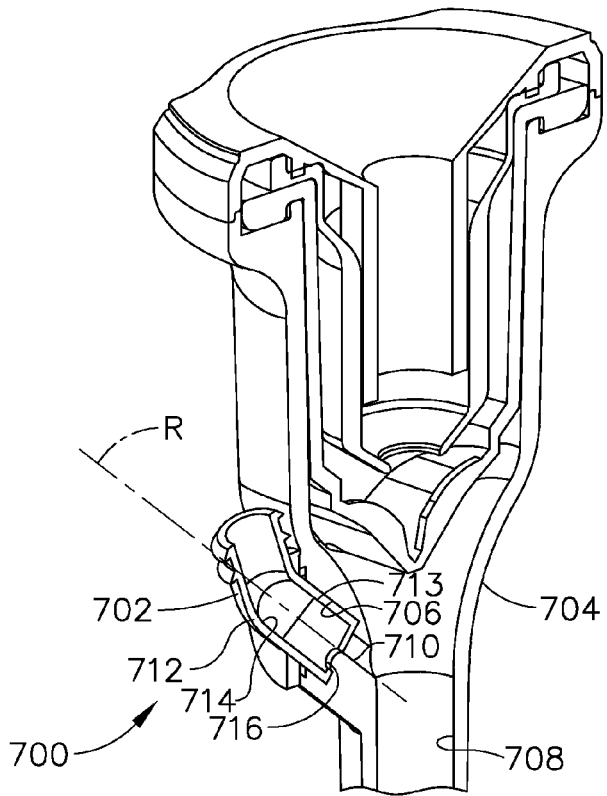
FIG. 16 is a front perspective view, in section, of a portion of a trocar sleeve assembly having an integral insufflation valve assembly in accordance with an eighth aspect of the disclosure, wherein the insufflation valve assembly is shown in a closed configuration.
Figure 17:
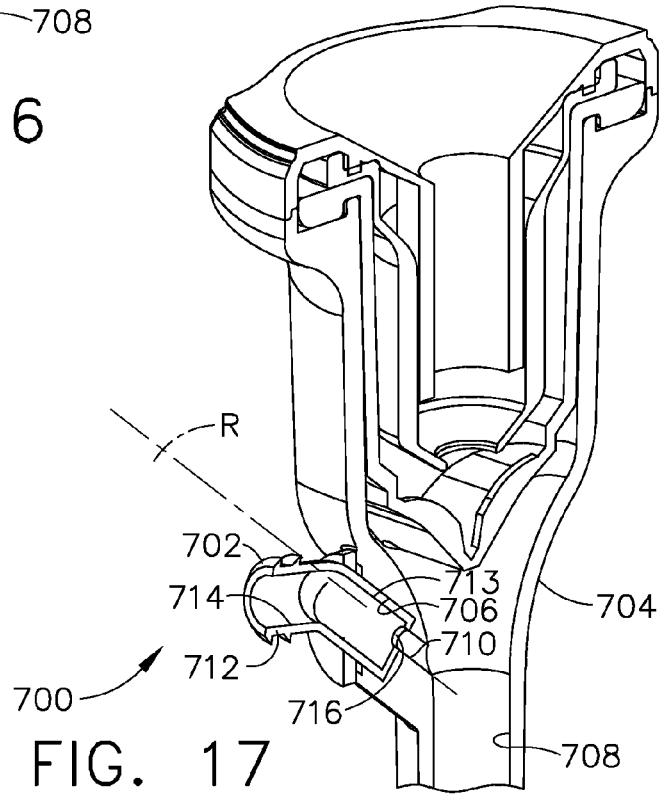
FIG. 17 is a front perspective view, in section, of the sleeve assembly of FIG. 16, wherein the insufflation valve assembly is shown in an open configuration.

As shown in FIGS. 16 and 17, in a first implementation of the seventh aspect, the insufflation valve assembly, generally designated 700, may include an insufflation port 702 and a trocar sleeve assembly 704. The trocar sleeve assembly 704 may define a bore 706 that is in fluid communication with the working channel 708 of the sleeve assembly 704 by way of a connecting channel 710. The insufflation port 702 may include a tubular body 712 that defines a channel 714 and includes a opening 716 into the channel 714. A distal portion 713 of the tubular body 712 may be received within the bore 706 and the insufflation port 702 may be rotatable in the bore 706 about an axis R of rotation relative to the sleeve assembly 704. Axis R may extend at an angle relative to the central axis of the trocar sleeve assembly 704.

As shown in FIG. 17, the insufflation port 702 may be rotated relative to the sleeve assembly 704 about axis R such that the opening 716 in the tubular body 712 of the insufflation port 702 is aligned with the connecting channel 710 of the sleeve assembly 704, thereby fluidly coupling the channel 714 of the insufflation port 702 with the working channel 708 of the sleeve assembly 704.

As shown in FIG. 16, the insufflation port 702 may also be rotated relative to the sleeve assembly 704 about axis R such that the opening 716 in the tubular body 712 of the insufflation port 702 is offset from the connecting channel 710 of the sleeve assembly 704, thereby fluidly decoupling the channel 714 of the insufflation port 702 from the working channel 708 of the sleeve assembly 704. Thus, in this embodiment, instead of using a push button or the like to fluidly isolate the insufflation port from the working channel of the sleeve assembly, a rotating insufflation port 702 may be used.

Figure 18:
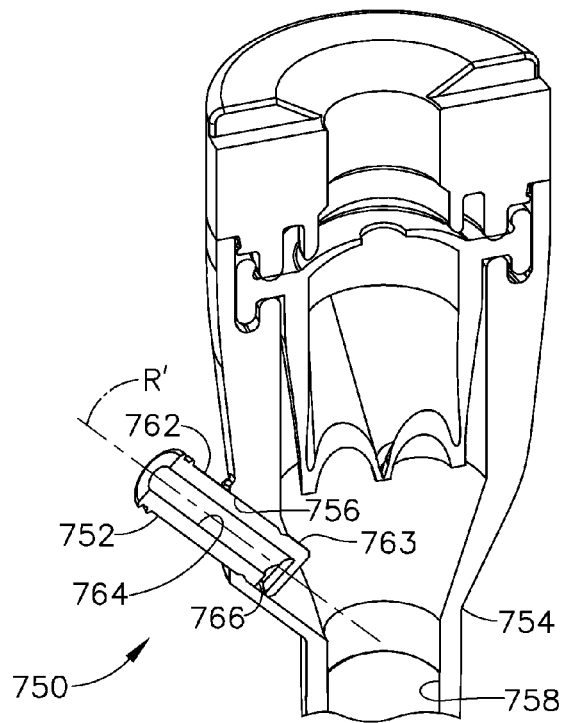
FIG. 18 is a front perspective view, in section, of a portion of a trocar sleeve assembly having an integral insufflation valve assembly in accordance with a ninth aspect of the disclosure, wherein the insufflation valve assembly is shown in a closed configuration.
Figure 19:
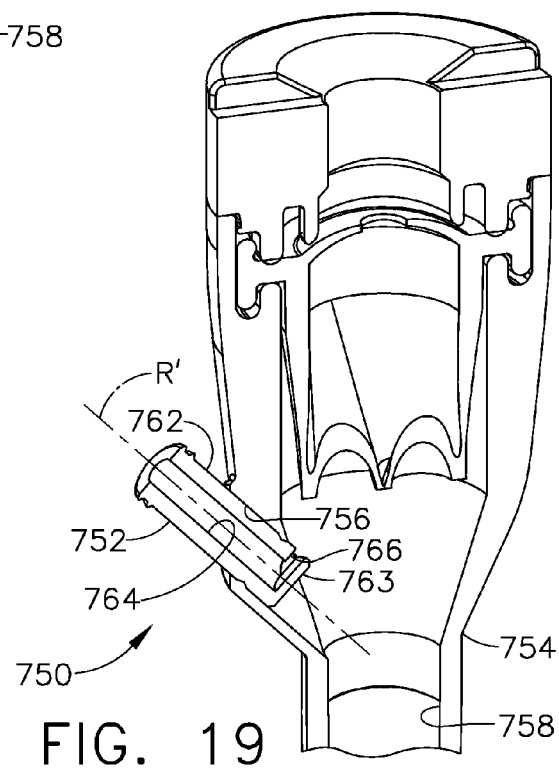
FIG. 19 is a front perspective view, in section, of the sleeve assembly of FIG. 18, wherein the insufflation valve assembly is shown in an open configuration.

As shown in FIGS. 18 and 19, in a second implementation of the seventh aspect, the insufflation valve assembly, generally designated 750, may include an insufflation port 752 and a trocar sleeve assembly 754. The trocar sleeve assembly 754 may define a bore 756 that is in direct fluid communication with the working channel 758 of the sleeve assembly 754. The insufflation port 752 may include a tubular body 762 that defines a channel 764 and includes a opening 766 into the channel 764. A distal portion 763 of the tubular body 762 may be received within the bore 756 and the insufflation port 752 may be rotatable in the bore 756 about an axis R' of rotation relative to the sleeve assembly 754.

As shown in FIG. 19, the insufflation port 752 may be rotated relative to the sleeve assembly 744 such that the opening 766 in the tubular body 762 of the insufflation port 752 is in direct fluid communication with the working channel 758 of the sleeve assembly 754.

As shown in FIG. 18, the insufflation port 752 may also be rotated relative to the sleeve assembly 754 such that the opening 766 in the tubular body 762 of the insufflation port 752 is sealed by the bore 756, thereby fluidly decoupling the channel 764 of the insufflation port 752 from the working channel 758 of the sleeve assembly 754.

Figure 20:
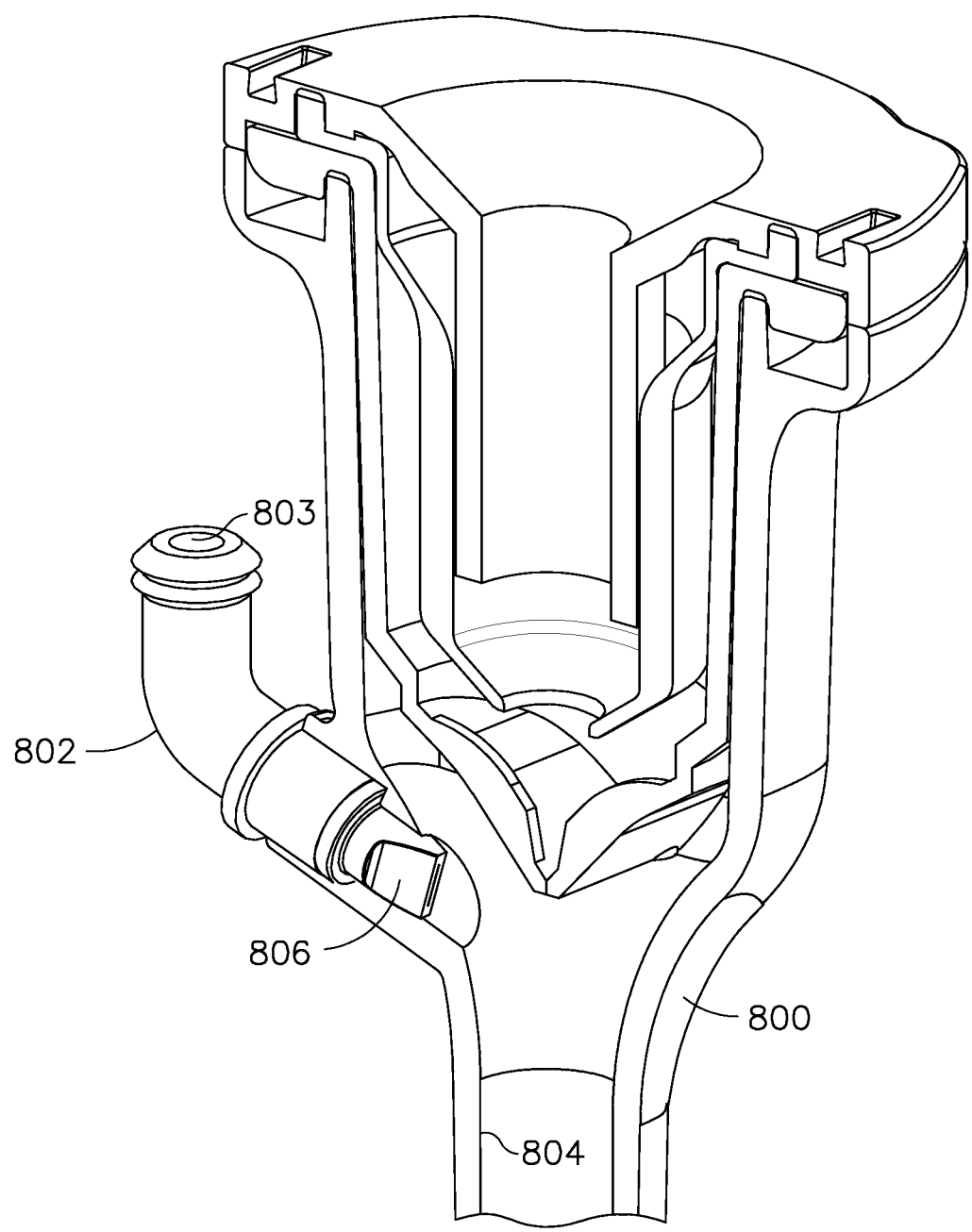
FIG. 20 is a front perspective view, partially in section, of a portion of a trocar sleeve assembly including an insufflation valve in accordance with a tenth aspect of the disclosure.

Referring to FIG. 20, in accordance with an eighth aspect, a trocar sleeve assembly 800 may include an insufflation port 802 that defines an internal channel 803 that is in fluid communication with the working channel 804 of the sleeve assembly 800. A check valve 806, such as a duckbill-type check valve, may be disposed between the internal channel 803 of the insufflation port 802 and the working channel 804 of the sleeve assembly 800. The check valve 806 may permit insufflation fluid to flow from the internal channel 803 of the insufflation port 802 to the working channel 804, but may substantially prevent insufflation fluid from flowing from the working channel 804 to the internal channel 803 of the insufflation port 802.

The various components of the disclosed trocar assembly, include the various channel seals, may be provided with an anti-microbial coating to limit cross-contamination and various surgical procedures are performed.

Although various embodiments and aspects of the disclosed trocar assembly have been shown and described, modifications may occur to those skilled in the art upon reading the specification. The present application includes such modifications and is limited only by the scope of the claims.

What is claimed is:

1. A trocar assembly comprising:
   a sleeve assembly defining a working channel extending axially therethrough and including an open proximal end adapted to receive a proximally-inserted medical instrument, an open distal end for protrusion of the proximally-inserted medical instrument from said working channel beyond said distal end, and an insufflation port, separate from and interposed between said proximal and distal ends, in fluid communication with said working channel; and
   an insufflation valve assembly fluidly coupled to said insufflation port, said insufflation valve assembly including a valve member retained within a housing, wherein said valve member defines an inlet channel and is biased relative to said housing to a first position in which said inlet channel is in fluid communication with said working channel, wherein said housing defines at least one vent opening for fluid discharge to the surrounding atmosphere, and wherein said valve member is moveable relative to said housing from said first position to a second position in which said working channel is in fluid communication with said vent opening so as to release insufflation fluid from the trocar assembly.

2. The trocar assembly of claim 1 wherein said inlet channel is fluidly decoupled from said working channel when said valve member is in said second position.

3. The trocar assembly of claim 1 wherein said valve member includes a sealing member and said housing defines a valve seat, wherein in said first position said sealing member is seated against said valve seat, and wherein in said first position said valve member, said housing, and said sealing member define a venting chamber which is in fluid communication with said vent opening yet fluidly decoupled from said working channel.

4. The trocar assembly of claim 3 wherein in said second position said sealing member is separated from contact with said valve seat so as to fluidly couple said working channel to said venting chamber.

5. The trocar assembly of claim 1 wherein said housing defines an opening, and wherein said defined inlet channel of said valve member projects outward through said opening such that said valve member is manually movable to said second position.

6. The trocar assembly of claim 2 wherein said valve member further defines an outlet channel in fluid communication with said working channel, wherein said inlet channel and said outlet channel are coaxially aligned yet separated by a bulkhead, and wherein said outlet channel is fluidly coupled with said inlet channel when said valve member is in said first position but fluidly decoupled from said inlet channel when said valve member is in said second position.

7. The trocar assembly of claim 6 further comprising a sealing member disposed between said valve member and said housing, wherein said sealing member fluidly isolates said outlet channel from said inlet channel when said valve member is in said second position.

8. The trocar assembly of claim 7 wherein said outlet channel includes a set of openings, with said openings being disposed on an inlet-channel-facing side of said sealing member in said first position but on an opposite-facing side of said sealing member in said second position.

9. A trocar assembly comprising:
   a sleeve assembly defining a working channel extending axially therethrough and including an open proximal end adapted to receive a proximally-inserted trocar, an open distal end for protrusion of the proximally-inserted medical trocar from said working channel beyond said distal end, and an insufflation port, separate from and interposed between said proximal and distal ends, in fluid communication with said working channel; and
   an insufflation valve assembly fluidly coupled to said insufflation port, said insufflation valve assembly including a housing having a proximal opening and a distal end fluidly coupled to the insufflation port, a valve member retained within said housing, and a sealing member disposed therebetween, wherein said housing includes a valve seat and defines at least one vent opening disposed proximally from said valve seat, and wherein said valve member defines an inlet channel and is biased relative to said housing to a proximal position in which said inlet channel is fluidly coupled with said working channel and in which said working channel is fluidly decoupled from said vent opening by engagement of said sealing member with said valve seat, and wherein said valve member is moveable relative to said housing from said proximal position to a distal position in which said working channel is fluidly coupled with said vent opening by disengagement of said sealing member from said valve seat.

10. The trocar assembly of claim 9 wherein said housing defines said valve seat, and wherein said valve member includes a groove carrying said sealing member for movement relative to said valve seat.

11. The trocar assembly of claim 10 wherein said sealing member is an O-ring, said groove is an annular groove about said valve member, and said valve seat is an annular projection of said housing.

12. The trocar assembly of claim 9 wherein a portion of said valve member extends through said proximal opening such that said valve member is manually movable to said distal position.

13. The trocar assembly of claim 9 wherein said valve member further defines an outlet channel in fluid communication with said working channel, wherein said inlet channel and said outlet channel are coaxially aligned yet separated by a bulkhead, and wherein said outlet channel is fluidly coupled with said inlet channel when said valve member is in said proximal position but fluidly decoupled from said inlet channel when said valve member is in said distal position.

14. The trocar assembly of claim 13 further comprising another sealing member disposed between said valve member and said housing, wherein said another sealing member fluidly isolates said outlet channel from said inlet channel when said valve member is in said distal position.

15. The trocar assembly of claim 1 further comprising a working channel seal interposed between the open distal end and the insufflation port.

16. The trocar assembly of claim 8 wherein said inlet channel includes another set of openings disposed on said inlet-channel-facing side of said sealing member.

17. The trocar assembly of claim 9 further comprising a working channel seal interposed between the open distal end and the insufflation port.

18. The trocar assembly of claim 14 wherein said outlet channel includes a set of openings, with said openings being disposed on an a proximal side of said another sealing member in said proximal position but on a distal side of said sealing member in said distal position.

19. The trocar assembly of claim 18 wherein said inlet channel includes another set of openings, with said another set of openings being disposed on said proximal side of said another sealing member.

* * * * *